United States Patent
Zhang et al.

(10) Patent No.: US 9,663,791 B2
(45) Date of Patent: May 30, 2017

(54) GREEN PROCESS FOR PRODUCING POLYHYDROXYALKANOATES AND CHEMICALS USING A RENEWABLE FEEDSTOCK

(75) Inventors: Zhigang Zhang, Watertown, MA (US); Christopher W. J. McChalicher, Wakefield, MA (US); Johan van Walsem, Acton, MA (US); Oliver P. Peoples, Arlington, MA (US); Richard P. Eno, Winchester, MA (US); Thomas Martin Ramseier, Newton, MA (US)

(73) Assignee: CJ Research Center LLC, Woburn, MA (US)

( * ) Notice: Subject to any disclaimer, the term of this patent is extended or adjusted under 35 U.S.C. 154(b) by 163 days.

(21) Appl. No.: 14/114,723

(22) PCT Filed: Apr. 26, 2012

(86) PCT No.: PCT/US2012/035217
§ 371 (c)(1),
(2), (4) Date: Mar. 27, 2014

(87) PCT Pub. No.: WO2012/149162
PCT Pub. Date: Nov. 1, 2012

(65) Prior Publication Data
US 2014/0234944 A1  Aug. 21, 2014

Related U.S. Application Data

(60) Provisional application No. 61/480,870, filed on Apr. 29, 2011.

(51) Int. Cl.
C12N 15/63 (2006.01)
C12N 1/20 (2006.01)
(Continued)

(52) U.S. Cl.
CPC .............. *C12N 15/63* (2013.01); *C12N 1/20* (2013.01); *C12N 15/52* (2013.01); *C12P 7/04* (2013.01);
(Continued)

(58) Field of Classification Search
CPC .......... C12N 15/63; C12N 1/20; C12N 15/52; C12P 7/18; C12P 7/04; C12P 7/45; C12P 7/62
See application file for complete search history.

(56) References Cited

U.S. PATENT DOCUMENTS 6,448,061 B1    9/2002  Pan et al.
8,546,125 B2 *  10/2013 Chen .................. C12N 9/88
                                               435/135
(Continued)

FOREIGN PATENT DOCUMENTS

WO    WO 99/14313 A2    3/1999

OTHER PUBLICATIONS

Choi et al., High-Level Production of Poly(3-Hydroxybutyrate-co-3-Hydroxyvalerate) by Fed-Batch Culture of Recombinant *Escherichia coli*., Appl. Environ. Microbiol. (Oct. 1999), vol. 65, No. 10, pp. 4363-4368.*
(Continued)

*Primary Examiner* — Alexander Kim
(74) *Attorney, Agent, or Firm* — Foley Hoag LLP

(57) ABSTRACT

Disclosed are organisms genetically engineered to make useful products when grown on ethanol as a carbon source. The organisms are genetically engineered to produce various useful products such as polyhydroxyalkanoates, diols, diacids, higher alcohols, and other useful chemicals.

6 Claims, 7 Drawing Sheets

(51) Int. Cl.
    C12N 15/52    (2006.01)
    C12P 7/18     (2006.01)
    C12P 7/04     (2006.01)
    C12P 7/46     (2006.01)
    C12P 7/62     (2006.01)
    C12P 7/24     (2006.01)
(52) U.S. Cl.
    CPC    *C12P 7/18* (2013.01); *C12P 7/24* (2013.01);
           *C12P 7/46* (2013.01); *C12P 7/625* (2013.01)

(56) References Cited

U.S. PATENT DOCUMENTS

2002/0164729 A1* 11/2002 Skraly ................. C12P 7/625
                                                   435/135
2004/0106176 A1*  6/2004 Skraly ................. C12N 9/0008
                                                   435/135

OTHER PUBLICATIONS

P0A9Q7 (last viewed on Dec. 23, 2015).*
Megazyme alcohol dehydrogease from *E. coli* ((last viewed on Dec. 23, 2015).*
Choi et al., Cloning of the Alcaligenes latus Polyhydroxyalkanoate Biosynthesis Genes and Use of These Genes for Enhanced Production of Poly(3-hydroxybutyrate) in *Escherichia coli.*, Appl. Environ. Microbiol. (Dec. 1999), vol. 64, No. 12, pp. 4897-4903.*
Mortlock (1992), The Evolution of Metabolic Function., CRC Press, p. 106.*
International Search Report and Written Opinion, PCT/US2012/035217, "Green Process for Producing Polyhydroxyalkanoates and Chemicals Using a Renewable Feedstock," date of mailing Dec. 4, 2012.
Wang, Y., et al., "Construction of recombinant Bacillus subtilis for production of polyhydroxyalkanoates," *Applied Biochemistry and Biotechnology*, 129-132: 1015-1022 (Apr. 2006).
Wolf, M., et al., "Genes encoding xylan and β-glucan hydrolysing enzymes in bacillus subtilis: characterization, mapping and construction of strains deficient in lichenase, cellulase and xylanase," *Microbiology, Society for General Microbiology, Reading, GB*, 141(2): 281-290 (Jan. 1995).
Yves Dailly, et al., "Novel alcohol dehydrogenase activity in a mutant of salmonella able to use ethanol as sole carbon source," *FEMS Microbiology Letters*, 201(1): 41-45 (Jul. 2001).
International Preliminary Report on Patentability, PCT/US2012/035217, "Green Process for Producing Polyhydroxyalkanoates and Chemicals Using a Renewable Feedstock," date of issuance Oct. 29, 2013.
Reddy, C.S.K., et al., "Polyhydroxyalkanoates: and overview," Bioresource Technology, 87: 137-146 (2003).
Mahishi, L.H., et al., "Poly(3-hydroxybutyrate) (PHB) synthesis by recombinant *Escherichia coli* harbouring Streptomyces aureofaciens PHB biosynthesis genes: Effect of various carbon and nitrogen sources," Microbiol. Res., 158: 19-27 (2003).

* cited by examiner

US 9,663,791 B2

GREEN PROCESS FOR PRODUCING POLYHYDROXYALKANOATES AND CHEMICALS USING A RENEWABLE FEEDSTOCK

RELATED APPLICATION

This application is the U.S. National Stage of International Application No. PCT/US2012/035217, filed Apr. 26, 2012, which designates the U.S., published in English, and claims the benefit of U.S. Provisional Application No. 61/480,870, filed on Apr. 29, 2011, the entire teachings of which are incorporated herein by reference.

INCORPORATION BY REFERENCE OF MATERIAL IN ASCII TEXT FILE

This application incorporates by reference the Sequence Listing contained in the following ASCII text file:

a) File name: 46141002002sequencelisting.txt; created Oct. 10, 2013, 34 KB in size.

FIELD OF THE INVENTION

The invention is related to the production of polyhydroxyalkanoate polymers, copolymers, diols, and diacids in microbes that are genetically engineered to produce these products using ethanol as a carbon source.

BACKGROUND

With dwindling petroleum resources, increasing energy prices, and environmental concerns, development of energy efficient biorefinery processes to produce biobased chemicals and materials from renewable, low cost, carbon resources offers a unique solution to overcoming the increasing limitations of petroleum-based chemicals.

Fuels, plastics, and chemicals derived from agricultural feedstocks are receiving considerable attention as the world looks for solutions to dwindling non-renewable petroleum resources (Herrera, *Nature Biotechnol.* 24:755-760 (2006); Kamm et al., *Adv. Biochem. Eng. Biotechnol.* 105:175-204 (2007); Ragauskas et al., *Science* 311:484-489 (2006)). In the United States, efforts have primarily focused on biofuels such as ethanol produced from the starch in maize kernels. Efforts in other parts of the world like Brazil use sugar feedstocks from sugarcane. Currently there are extensive efforts to develop new sources of feedstocks for ethanol production including cellulose hydrolysate from biomass.

Polyhydroxyalkanoates (PHAs), a family of naturally renewable and biodegradable plastics, occur in nature as a storage reserve in some microbes faced with nutrient limitation (Madison et al., *Microbiol. Mol. Biol. Rev.* 63:21-53 (1999)) and possess properties enabling their use in a variety of applications currently served by petroleum-based polymers. PHAs can be extracted from microorganisms or genetically engineered crops and used in polymer form as PHA biobased plastics or can be chemically or thermally converted to a range of renewable chemicals. PHA biobased plastics can be produced via commercial large scale fermentations of microbial strains and the marketing of these plastics in a variety of applications is well under way (Bieles, *Plastics and Rubber Weekly*, February 17:1 (2006)). Since they are inherently biodegradable in soil, compost, and marine environments, they can decrease plastic waste disposal issues.

Existing fermentation methods for producing polyhydroxyalkanoates utilize wild-type or transgenic microorganisms cultured on specific substrates to produce the desired PHA polymer composition. In many cases the polymers of interest are copolymers of the (D)-isomer of 3-hydroxybutyrate copolymerized with one other 3, 4 or 5-hydroxyacids. These copolymers are produced as granular inclusions inside the cells and are random copolymers. Existing fermentation methods generally use clean sugars, fatty acids or vegetable oils as the primary feedstock for the microorganisms. Secondary feedstocks are usually supplied to enable the incorporation of the second monomer.

The availability and cost of corn or cane sugars as a feedstock can be prohibitively high especially when growing microbes on an industrial scale. Therefore there is a need to find lower cost carbon substrates for producing PHAs via microbial fermentation processes.

SUMMARY OF THE INVENTION

Disclosed herein are organisms for producing polyhydroxyalkanoates, diols, and diacids when grown on ethanol (or xylose) as a carbon source. The organisms described are genetically engineered to incorporate enzymes of metabolic pathways for utilizing ethanol as a carbon source to produce sufficient amounts of polyhydroxyalkanoates or copolymers that can be further converted to diols, higher alcohols or diacids. The yield achieved by such processes is an economically viable alternative due to increasing production or improved production of the desired products or by reducing side products.

In some embodiments, if the microbial organism is naturally capable of using ethanol as a carbon source (e.g., having a pathway comprising an aldehyde dehydrogenase and alcohol dehydrogenase for utilizing ethanol (e.g., acinetoCyc pathway), for example *A. baylyi* ADPI or *corynebacterium glutamicum* having Cg107 and Cg3098)), additional enzymes of the pathway for producing polyhydroxyalkanoates or copolymers can be incorporated by genetic modification of the organism.

Additionally, if the organism is not capable of utilizing ethanol as a carbon source then enzyme(s) for the metabolic pathway of converting ethanol to acetyl coA are introduced into the genome. For example, genes encoding aldehyde dehydrogenase and alcohol dehydrogenase enzymes are incorporated for producing a sufficient amount of enzymes for utilizing ethanol as the carbon source.

In one aspect, the invention discloses an organism homologously capable of converting ethanol to acetyl-CoA when grown on ethanol as a carbon source, where the organism is genetically engineered to produce a polyhydroxyalkanoate polymer. In these embodiments, the organism (e.g., microbe, bacteria) is genetically modified to incorporate the enzymes in a metabolic pathway for converting acetyl-CoA to a desired product(s), for example poly-3-hydroxybutyrate (e.g., see FIG. 3), poly-4-hydroxybutyrate (e.g., see FIG. 4), poly-3-hydroxypropionate (e.g., see FIG. 5), poly-5-hydroxyvalerate (e.g., see FIG. 6), poly-3-hydroxybutyrate-co-4-hydroxybutyrate copolymer (e.g., see FIG. 7), poly-3-hydroxybutyrate-co-5-hydroxyvalerate copolymer (e.g., see FIG. 8), 1,4-butanediol (e.g., see FIG. 9), isopropanol (e.g., see FIG. 10), 1-propanol (e.g., see FIG. 11), or adipate (e.g., see FIG. 12).

Also disclosed is an organism homologously capable of producing polyhydroxyalkanoate polymer, where the organism is genetically engineered to convert ethanol to acetyl-CoA when grown on ethanol as a carbon source. The appropriate enzymes in the metabolic pathway to convert ethanol to acetyl-CoA are incorporated into the organism (e.g., see FIG. 1).

In another aspect, the invention discloses an organism that is genetically engineered to convert ethanol to acetyl-CoA when grown on ethanol as a carbon source, and genetically engineered to produce polyhydroxyalkanoate polymer. In this aspect both pathways (ethanol to acetyl-CoA pathway) and the desired polyhydroxyalkanoate polymer pathway are incorporated into the genome of the organism.

Such organisms produce one or more polyhydroxyalkanoate polymers or copolymers when grown on ethanol as a carbon source. The polyhydroxyalkanoate polymer can be polyglycolic, acid (PGA), poly-3-hydroxybutyrate (P3HB), poly-3-hydroxypropionate (P3HP), poly-4-hydroxybutyrate (P4HB), poly-5-hydroxyvalerate (P5HV), poly-3-hydroxybutyrate-co-4-hydroxybutyrate (P(3HB-co-4HB)), poly-3-hydroxybutyrate-co-3-hydroxyvalerate (P(3HB-co-3HV)), or poly-3-hydroxybutyrate-co-5-hydroxyvalerate (P(3HB-co-5HV)) or combinations and copolymers of these.

In a further aspect, the invention discloses an organism homologously capable of converting ethanol to acetyl-CoA when grown on ethanol as a carbon source, where the organism is genetically engineered, for example, by genetically introducing non-naturally produced enzymes in a pathway to produce diol (e.g., 1,3-propanediol, 1,4-butanediol, 1,5-pentanediol, or 1,6-hexanediol and the like).

In another aspect, the invention discloses an organism homologously capable of producing diol, where the organism is genetically engineered to convert ethanol to acetyl-CoA when grown on ethanol as a carbon source.

An additional aspect of the invention discloses an organism that is genetically engineered to convert ethanol to acetyl-CoA when grown on ethanol as a carbon source, and genetically engineered to produce diol (e.g., 1,3-propanediol, 1,4-butanediol, 1,5-pentanediol, or 1,6-hexanediol and the like).

Also disclosed is an organism homologously capable of converting ethanol to acetyl-CoA when grown on ethanol as a carbon source, where the organism is genetically engineered to produce diacid (e.g., succinic acid, glutaric acid, or adipic acid).

A further disclosure reveals an organism homologously capable of producing diacid, where the organism is genetically engineered to convert ethanol to acetyl-CoA when grown on ethanol as a carbon source.

Also disclosed is an organism that is genetically engineered to convert ethanol to acetyl-CoA when grown on ethanol as a carbon source, and genetically engineered to produce diacid.

Such organisms can produce diacids when grown on ethanol as a carbon source. The diacid can be succinic acid, glutaric acid, or adipic acid.

Also disclosed is an organism homologously capable of converting ethanol to acetyl-CoA when grown on ethanol as a carbon source, where the organism is genetically engineered to produce higher alcohols (e.g., isopropanol, 1-propanol and the like).

A further disclosure reveals an organism homologously capable of producing higher alcohols, where the organism is genetically engineered to convert ethanol to acetyl-CoA when grown on ethanol as a carbon source.

Also disclosed is an organism that is genetically engineered to convert ethanol to acetyl-CoA when grown on ethanol as a carbon source, and genetically engineered to produce higher alcohols.

Such organisms can produce higher alcohols when grown on ethanol as a carbon source. The higher alcohols can be isopropanol or 1-propanol.

Also disclosed herein are processes for producing polyhydroxyalkanoates, diols, diacids, and higher alcohols from organisms grown on ethanol as a carbon source.

In one aspect, the invention discloses a process for producing polyhydroxyalkanoate, comprising: providing an organism capable of converting ethanol to acetyl-CoA when grown on ethanol as a carbon source; genetically engineering the organism to produce polyhydroxyalkanoate polymer, thereby producing an ethanol-utilizing organism genetically engineered to produce polyhydroxyalkanoate; and providing ethanol to the ethanol-utilizing organism genetically engineered to produce polyhydroxyalkanoate; thereby producing polyhydroxyalkanoate.

Also disclosed is a process for producing polyhydroxyalkanoate, comprising: providing an organism capable of producing polyhydroxyalkanoate polymer; genetically engineering the organism to convert ethanol to acetyl-CoA when grown on ethanol as a carbon source, thereby producing a polyhydroxyalkanoate-producing organism genetically engineered to utilize ethanol; and providing ethanol to the polyhydroxyalkanoate-producing organism genetically engineered to utilize ethanol; thereby producing polyhydroxyalkanoate.

In a further aspect, the invention discloses a process for producing polyhydroxyalkanoate, comprising: providing an organism; genetically engineering the organism to convert ethanol to acetyl-CoA when grown on ethanol as a carbon source, thereby producing an organism genetically engineered to utilize ethanol; genetically engineering the organism to produce polyhydroxyalkanoate polymer, thereby producing an organism genetically engineered to produce polyhydroxyalkanoate and utilize ethanol; and providing ethanol to the organism genetically engineered to produce polyhydroxyalkanoate and utilize ethanol; thereby producing polyhydroxyalkanoate.

In such processes, the polyhydroxyalkanoate polymer can be polyglycolic acid (PGA), poly-3-hydroxybutyrate (P3HB), poly-3-hydroxypropionate (P3HP), poly-4-hydroxybutryrate (P4HB), poly-5-hydroxyvalerate (P5HV), poly-3-hydroxybutyrate-co-4-hydroxybutyrate (P(3HB-co-4HB)), poly-3-hydroxybutyrate-co-3-hydroxyvalerate (P(3HB-co-3HV)), or poly-3-hydroxybutyrate-co-5-hydroxyvalerate (P(3HB-co-5HV)) and combinations and copolymers of these. In certain embodiments, the copolymers are a poly(3-hydroxybutyrate-co-4-hydroxybutyrate) with 2% to 50% 4-hydroxybutyrate content, a poly(3-hydroxybutyrate-co-3-hydroxyvalerate) with 2% to 50% 3-hydroxyvalerate content, a poly(3-hydroxybutyrate-co-5-hydroxyvalerate) with 2% to 50% 5-hydroxyvalerate content, a poly(3-hydroxybutyrate-co-4-hydroxybutyrate) with 5% to 15% 4-hydroxybutyrate content, a poly(3-hydroxybutyrate-co-3-hydroxyvalerate) with 5% to 40% 3-hydroxyvalerate content, a poly(3-hydroxybutyrate-co-5-hydroxyvalerate) with 5% to 40% 5-hydroxyvalerate content.

Also disclosed herein is a process for producing diol, comprising: providing an organism capable of converting ethanol to acetyl-CoA when grown on ethanol as a carbon source; genetically engineering the organism to produce diol, thereby producing an ethanol-utilizing organism genetically engineered to produce diol; and providing ethanol to the ethanol-utilizing organism genetically engineered to produce diol; thereby producing diol.

Another process is disclosed for producing diol, comprising: providing an organism capable of producing diol;

genetically engineering the organism to convert ethanol to acetyl-CoA when grown on ethanol as a carbon source, thereby producing a diol-producing organism genetically engineered to utilize ethanol; and providing ethanol to the diol-producing organism genetically engineered to utilize ethanol; thereby producing diol.

Also disclosed is a process for producing diol, comprising: providing an organism; genetically engineering the organism to convert ethanol to acetyl-CoA when grown on ethanol as a carbon source, thereby producing an organism genetically engineered to utilize ethanol; genetically engineering the organism to produce diol, thereby producing an organism genetically engineered to produce diol and utilize ethanol; and providing ethanol to the organism genetically engineered to produce diol and utilize ethanol; thereby producing diol.

In such processes, the diol can be 1,3-propanediol, 1,4-butanediol, 1,5-pentanediol, or 1,6-hexanediol.

Also disclosed herein is a process for producing diacid, comprising: providing an organism capable of converting ethanol to acetyl-CoA when grown on ethanol as a carbon source; genetically engineering the organism to produce diacid, thereby producing an ethanol-utilizing organism genetically engineered to produce diacid; and providing ethanol to the ethanol-utilizing organism genetically engineered to produce diacid; thereby producing diacid.

In an additional aspect, the invention discloses a process for producing diacid, comprising: providing an organism capable of producing diacid; genetically engineering the organism to convert ethanol to acetyl-CoA when grown on ethanol as a carbon source, thereby producing a diacid-producing organism genetically engineered to utilize ethanol; and providing ethanol to the diacid-producing organism genetically engineered to utilize ethanol; thereby producing diacid.

A further aspect discloses a process for producing diacid, comprising: providing an organism; genetically engineering the organism to convert ethanol to acetyl-CoA when grown on ethanol as a carbon source, thereby producing an organism genetically engineered to utilize ethanol; genetically engineering the organism to produce diacid, thereby producing an organism genetically engineered to produce diacid and utilize ethanol; and providing ethanol to the organism genetically engineered to produce diacid and utilize ethanol; thereby producing diacid.

In such processes, the diacid can be succinic acid, glutaric acid, and adipic acid.

Also disclosed herein is a process for producing higher alcohol, comprising: providing an organism capable of converting ethanol to acetyl-CoA when grown on ethanol as a carbon source; genetically engineering the organism to produce higher alcohol, thereby producing an ethanol-utilizing organism genetically engineered to produce higher alcohol; and providing ethanol to the ethanol-utilizing organism genetically engineered to produce higher alcohol; thereby producing higher alcohol.

In an additional aspect, the invention discloses a process for producing higher alcohol, comprising: providing an organism capable of producing higher alcohol; genetically engineering the organism to convert ethanol to acetyl-CoA when grown on ethanol as a carbon source, thereby producing a higher alcohol-producing organism genetically engineered to utilize ethanol; and providing ethanol to the higher alcohol-producing organism genetically engineered to utilize ethanol; thereby producing higher alcohol.

A further aspect discloses a process for producing higher alcohol, comprising: providing an organism; genetically engineering the organism to convert ethanol to acetyl-CoA when grown on ethanol as a carbon source, thereby producing an organism genetically engineered to utilize ethanol; genetically engineering the organism to produce higher alcohol, thereby producing an organism genetically engineered to produce higher alcohol and utilize ethanol; and providing ethanol to the organism genetically engineered to produce higher alcohol and utilize ethanol; thereby producing higher alcohol.

In such processes, the higher alcohol can be isopropanol or 1-propanol.

In one aspect, the invention discloses an organism homologously capable of converting xylose to acetyl-CoA when grown on xylose as a carbon source, where the organism is genetically engineered to produce polyhydroxyalkanoate polymer.

Also disclosed is an organism homologously capable of producing polyhydroxyalkanoate polymer, where the organism is genetically engineered to convert xylose to acetyl-CoA when grown on xylose as a carbon source.

In another aspect, the invention discloses an organism that is genetically engineered to convert xylose to acetyl-CoA when grown on xylose as a carbon source, and genetically engineered to produce polyhydroxyalkanoate polymer.

Such organisms can produce polyhydroxyalkanoate polymer when grown on xylose as a carbon source. The polyhydroxyalkanoate polymer can be polyglycolic acid (PGA), poly-3-hydroxybutyrate (P3HB), poly-3-hydroxypropionate (P3HP), poly-4-hydroxybutryrate (P4HB), poly-5-hydroxyvalerate (P5HV), poly-3-hydroxybutyrate-co-4-hydroxybutyrate (P(3HB-co-4HB)), poly-3-hydroxybutyrate-co-3-hydroxyvalerate (P(3HB-co-3HV)), or poly-3-hydroxybutyrate-co-5-hydroxyvalerate (P(3HB-co-5HV)).

In a further aspect, the invention discloses an organism homologously capable of converting xylose to acetyl-CoA when grown on xylose as a carbon source, where the organism is genetically engineered to produce diol.

In another aspect, the invention discloses an organism homologously capable of producing diol, where the organism is genetically engineered to convert xylose to acetyl-CoA when grown on xylose as a carbon source.

An additional aspect of the invention discloses an organism that is genetically engineered to convert xylose to acetyl-CoA when grown on xylose as a carbon source, and genetically engineered to produce diol.

Such organisms can produce diols when grown on xylose as a carbon source. The diol can be 1,3-propanediol, 1,4-butanediol, 1,5-pentanediol, or 1,6-hexanediol.

Also disclosed is an organism homologously capable of converting xylose to acetyl-CoA when grown on xylose as a carbon source, where the organism is genetically engineered to produce diacid.

A further disclosure reveals an organism homologously capable of producing diacid, where the organism is genetically engineered to convert xylose to acetyl-CoA when grown on xylose as a carbon source.

Also disclosed is an organism that is genetically engineered to convert xylose to acetyl-CoA when grown on xylose as a carbon source, and genetically engineered to produce diacid.

Such organisms can produce diacids when grown on xylose as a carbon source. The diacid can be succinic acid, glutaric acid, or adipic acid.

Also disclosed is an organism homologously capable of converting xylose to acetyl-CoA when grown on xylose as a carbon source, where the organism is genetically engineered to produce higher alcohol.

A further disclosure reveals an organism homologously capable of producing higher alcohol, where the organism is genetically engineered to convert xylose to acetyl-CoA when grown on xylose as a carbon source.

Also disclosed is an organism that is genetically engineered to convert xylose to acetyl-CoA when grown on xylose as a carbon source, and genetically engineered to produce higher alcohol.

Such organisms can produce higher alcohol when grown on xylose as a carbon source. The higher alcohol can be isopropanol or 1-propanol.

Also disclosed herein are processes for producing polyhydroxyalkanoates, diols, diacids, and higher alcohols from organisms grown on xylose as a carbon source.

In one aspect, the invention discloses a process for producing polyhydroxyalkanoate, comprising: providing an organism capable of converting xylose to acetyl-CoA when grown on xylose as a carbon source; genetically engineering the organism to produce polyhydroxyalkanoate polymer, thereby producing a xylose-utilizing organism genetically engineered to produce polyhydroxyalkanoate; and providing xylose to the xylose-utilizing organism genetically engineered to produce polyhydroxyalkanoate; thereby producing polyhydroxyalkanoate.

Also disclosed is a process for producing polyhydroxyalkanoate, comprising: providing an organism capable of producing polyhydroxyalkanoate polymer; genetically engineering the organism to convert xylose to acetyl-CoA when grown on xylose as a carbon source, thereby producing a polyhydroxyalkanoate-producing organism genetically engineered to utilize xylose; and providing xylose to the polyhydroxyalkanoate-producing organism genetically engineered to utilize xylose; thereby producing polyhydroxyalkanoate.

In a further aspect, the invention discloses a process for producing polyhydroxyalkanoate, comprising: providing an organism; genetically engineering the organism to convert xylose to acetyl-CoA when grown on xylose as a carbon source, thereby producing an organism genetically engineered to utilize xylose; genetically engineering the organism to produce polyhydroxyalkanoate polymer, thereby producing an organism genetically engineered to produce polyhydroxyalkanoate and utilize xylose; and providing xylose to the organism genetically engineered to produce polyhydroxyalkanoate and utilize xylose; thereby producing polyhydroxyalkanoate.

In such processes, the polyhydroxyalkanoate polymer can be polyglycolic acid (PGA), poly-3-hydroxybutyrate (P3HB), poly-3-hydroxypropionate (P3HP), poly-4-hydroxybutryrate (P4HB), poly-5-hydroxyvalerate (P5HV), poly-3-hydroxybutyrate-co-4-hydroxybutyrate (P(3HB-co-4HB)), poly-3-hydroxybutyrate-co-3-hydroxyvalerate (P(3HB-co-3HV)), or poly-3-hydroxybutyrate-co-5-hydroxyvalerate (P(3HB-co-5HV)), copolymers and mixtures of these polymers.

Also disclosed herein is a process for producing diol, comprising: providing an organism capable of converting xylose to acetyl-CoA when grown on xylose as a carbon source; genetically engineering the organism to produce diol, thereby producing an xylose-utilizing organism genetically engineered to produce diol; and providing xylose to the xylose-utilizing organism genetically engineered to produce diol; thereby producing diol.

Another process is disclosed for producing diol comprising: providing an organism capable of producing diol; genetically engineering the organism to convert xylose to acetyl-CoA when grown on xylose as a carbon source, thereby producing a diol-producing organism genetically engineered to utilize xylose; and providing xylose to the diol-producing organism genetically engineered to utilize xylose; thereby producing diol.

Also disclosed is a process for producing diol, comprising: providing an organism; genetically engineering the organism to convert xylose to acetyl-CoA when grown on xylose as a carbon source, thereby producing an organism genetically engineered to utilize xylose; genetically engineering the organism to produce diol, thereby producing an organism genetically engineered to produce diol and utilize xylose; and providing xylose to the organism genetically engineered to produce diol and utilize xylose; thereby producing diol.

In such processes, the diol can be 1,3-propanediol, 1,4-butanediol, 1,5-pentanediol, or 1,6-hexanediol.

Also disclosed herein is a process for producing diacid, comprising: providing an organism capable of converting xylose to acetyl-CoA when grown on xylose as a carbon source; genetically engineering the organism to produce diacid, thereby producing an xylose-utilizing organism genetically engineered to produce diacid; and providing xylose to the xylose-utilizing organism genetically engineered to produce diacid; thereby producing diacid.

In an additional aspect, the invention discloses a process for producing diacid, comprising: providing an organism capable of producing diacid; genetically engineering the organism to convert xylose to acetyl-CoA when grown on xylose as a carbon source, thereby producing a diacid-producing organism genetically engineered to utilize xylose; and providing xylose to the diacid-producing organism genetically engineered to utilize xylose; thereby producing diacid.

A further aspect discloses a process for producing diacid, comprising: providing an organism; genetically engineering the organism to convert xylose to acetyl-CoA when grown on xylose as a carbon source, thereby producing an organism genetically engineered to utilize xylose; genetically engineering the organism to produce diacid, thereby producing an organism genetically engineered to produce diacid and utilize xylose; and providing xylose to the organism genetically engineered to produce diacid and utilize xylose; thereby producing diacid.

In such processes, the diacid can be succinic acid, glutaric acid, and adipic acid.

Also disclosed herein is a process for producing higher alcohol, comprising: providing an organism capable of converting xylose to acetyl-CoA when grown on xylose as a carbon source; genetically engineering the organism to produce higher alcohol, thereby producing an xylose-utilizing organism genetically engineered to produce higher alcohol; and providing xylose to the xylose-utilizing organism genetically engineered to produce higher alcohol; thereby producing higher alcohol.

In an additional aspect, the invention discloses a process for producing higher alcohol, comprising: providing an organism capable of producing higher alcohol; genetically engineering the organism to convert xylose to acetyl-CoA when grown on xylose as a carbon source, thereby producing a higher alcohol-producing organism genetically engineered to utilize xylose; and providing xylose to the higher alcohol-producing organism genetically engineered to utilize xylose; thereby producing higher alcohol.

A further aspect discloses a process for producing higher alcohol, comprising: providing an organism; genetically engineering the organism to convert xylose to acetyl-CoA when grown on xylose as a carbon source, thereby producing an organism genetically engineered to utilize xylose; genetically engineering the organism to produce higher alcohol, thereby producing an organism genetically engineered to produce higher alcohol and utilize xylose; and providing xylose to the organism genetically engineered to produce higher alcohol and utilize xylose; thereby producing higher alcohol.

In such processes, the higher alcohol can be isopropanol or 1-propanol.

The organisms disclosed herein, and those used in the processes, can be *Escherichia coli, Ralstonia eutropha, Acinetobacter baumannii, Acinetobacter baylyi, Acinetobacter aceti, Acinetobacter* sp. DR1, *Acinetobacter calcoaceticus, Acinetobacter haemolyticus, Acinetobacter johnsonii, Acinetobacter junii, Acinetobacter lwoffii, Acinetobacter radioresistens, Acinetobacter venetianus, Acinetobacter* sp. DSM, *Zoogloea ramigera, Allochromatium vinosum, Rhodococcus ruber, Delftia acidovorans, Aeromonas caviae, Synechocystis* sp. PCC 6803, *Synechococcus elongatus* PCC 7942, *Thiocapsa pfenigii, Bacillus megaterium, Clostridium kluyveri, Methylobacterium extorquens, Nocardia corralina, Nocardia salmonicolor, Pseudomonas fluorescens, Pseudomonas oleovorans, Pseudomonas* sp. 6-19, *Pseudomonas* sp. 61-3 and *Pseudomonas putida, Rhodobacter sphaeroides, Alcaligenes latus, Klebsiella oxytoca, Anaerobiospirillum succiniciproducens, Actinobacillus succinogenes, Mannheimia succiniciproducens, Rhizobium etli, Bacillus subtilis, Corynebacterium glutamicum, Gluconobacter oxydans, Zymomonas mobilis, Lactococcus lactis, Lactobacillus plantarum, Streptomyces coelicolor, Clostridium acetobutylicum, Saccharomyces cerevisiae, Schizosaccharomyces pombe, Kluyveromyces lactis, Kluyveromyces marxianus, Aspergillus terreus, Aspergillus niger, Pichia pastoris, Chlorella* spp., *Chlorella minutissima, Chlorella emersonii, Chlorella sorokiniana, Chlorella ellipsoidea, Chlorella* sp., and *Chlorella prototheoides.*

It is understood that any of a number of genetic modifications, as disclosed herein, can be used alone or in various combinations of one or more of the genetic modifications in one or more pathways to utilize ethanol as a carbon source and produce polyhydroxyalkanoates, diols, diacids, higher alcohols and the like. It should be understood that this invention is not limited to the embodiments disclosed in this Summary, and it is intended to cover modifications that are within the spirit and scope of the invention, as defined by the claims.

DETAILED DESCRIPTION

Figure 1:
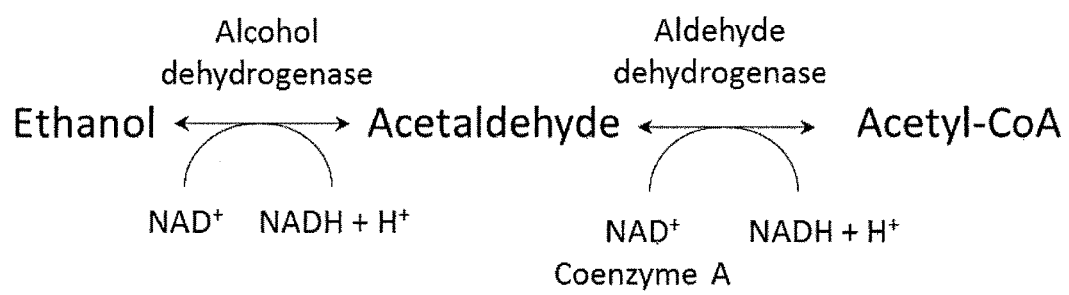
FIG. 1 is a diagram showing the pathway for converting ethanol to acetyl-CoA, and the enzymes involved.

Disclosed are organisms genetically engineered to make useful products when grown on ethanol as a carbon source. The organisms are genetically engineered to produce various useful products such as polyhydroxyalkanoates (including, but not limited to, polyglycolic acid (PGA), poly-3-hydroxybutyrate (P3HB), poly-3-hydroxypropionate (P3HP), poly-4-hydroxybutyrate (P4HB), poly-5-hydroxyvalerate (P5HV), poly-(3-hydroxybutyrate-co-4-hydroxybutyrate) (P3HB-co-4HB), poly-3-hydroxybutyrate-co-3-hydroxyvalerate (P(3HB-co-3HV)), poly-(3-hydroxybutyrate-co-5-hydroxyvalerate) (P3HB-co-5HV)), or copolymers and mixtures of these polymers, diols (including, but not limited to, 1,3-propanediol (1,3PD), 1,4-butanediol (1,4BD), 1,5-pentanediol (1,5PD), 1,6-hexanediol (1,6HD)), and other chemicals, such as higher alcohols (e.g., isopropanol, 1-propanol) and diacids (e.g., adipic acid, glutaric acid, and succinic acid). The organisms are engineered to efficiently utilize ethanol (or in some cases xylose) as the carbon source to produce a product with a yield that is cost effective. In certain embodiments, the yield of product from the ethanol carbon source is an increased yield that approaches the theoretic yield of the reaction. For example, the yield should be 20%, 30%, 40%, 50%, 60%, 70%, 80%, 90%, 95% or 100% of the theoretical yield. In certain aspects of the invention, the organism is modified to use ethanol as the energy source to product a desirable product without diverting energy to the conversion of undesirable products. Modification of the metabolic pathways or incorporation of metabolic pathways for grown on ethanol as the carbon source to increase production of polyhydroxyalkanoates or other end-products.

In one aspect, an organism that naturally produces such products can be engineered or selected to grow on ethanol as a carbon source. For instance, *Ralstonia eutropha* is a microbe known to produce polyhydroxyalkanoates. As shown herein, such organisms can be altered so that they grow on ethanol as a carbon source. The polymers produced can be the polyhydroxyalkanoate polymer can be polyglycolic acid (PGA), poly-3-hydroxybutyrate (P3HB), poly-3-hydroxypropionate (P3HP), poly-4-hydroxybutyrate (P4HB), poly-5-hydroxyvalerate (P5HV), poly-3-hydroxybutyrate-co-4-hydroxybutyrate (P(3HB-co-4HB)), poly-3-hydroxybutyrate-co-3-hydroxyvalerate (P(3HB-co-3HV)), or poly-3-hydroxybutyrate-co-5-hydroxyvalerate (P(3HB-co-5HV)), copolymers and mixtures of these polymers. The organism is genetically-engineered to use ethanol as a carbon source by introducing or altering enzymes in a pathway to convert ethanol to acetyl-coA.

In another aspect, organisms that are known to utilize ethanol as a carbon source (e.g., *Acinetobacter baylyi*) can be engineered to produce polyhydroxyalkanoates and other products as described above.

In still another aspect, organisms can be engineered to produce polyhydroxyalkanoates and other useful products, and also engineered to do so using ethanol as a carbon source (e.g., *Escherichia coli*).

Polyhydroxyalkanoates (PHAs) are biodegradable plastics which can be used to make, without limitation, films (e.g., packaging films, agricultural films, mulch film), golf tees, caps and closures, agricultural supports and stakes, paper and board coatings (e.g., for cups, plates, boxes, etc.), thermoformed products (e.g., trays, containers, yogurt pots, plant pots, noodle bowls, moldings, etc.), housings (e.g., for electronic items) bags (e.g., trash bags, grocery bags, food bags, compost bags, etc.), hygiene articles (e.g., diapers, feminine hygiene products, incontinence products, disposable wipes, etc.) and coatings including paints and varnishes as well as coatings for pelleted products (e.g., pelleted fertilizer, herbicides, pesticides, seeds, etc.).

PHAs have also been used to develop biomedical devices including sutures, repair devices, repair patches, slings, cardiovascular patches, orthopedic pins, adhesion barriers, stents, guided tissue repair/regeneration devices, articular cartilage repair devices, nerve guides, tendon repair devices, bone marrow scaffolds, and wound dressings.

Polyhydroxyalkanoates can be produced by a fermentation process. Existing fermentation methods for producing polyhydroxyalkanoates utilize wild-type or transgenic microorganisms cultured on specific substrates to produce the desired PHA polymer composition. In many cases the polymers of interest are copolymers of the (D)-isomer of 3-hydroxybutyrate copolymerized with one other 3, 4 or 5-hydroxyacids. These copolymers are produced as granular inclusions inside the cells and are random copolymers. Mixtures of one or more copolymers or homopolymers or combination of these polyhydroxyalkanoate monomers are also contemplated herein.

PHAs, diols, diacids and higher alcohols are industrially useful. It is highly desirable to use non-petroleum renewable carbon substrates as feedstock for the production of PHAs, diols, diacids and higher alcohols both to lower cost and to provide materials that are made entirely from renewable resources. It is also desirable to develop processes for the production of these products which reduce the production of greenhouse gasses. The methods described herein provide the process for producing PHAs, dials, diacids and higher acids from organisms that are naturally grown or genetically altered to use ethanol as a carbon source.

The term "PHA copolymer" refers to a polymer composed of at least two different hydroxyalkanoic acid monomers.

The term "PHA homopolymer" refers to a polymer that is composed of a single hydroxyalkanoic acid monomer.

As used herein, a "vector" is a replicon, such as a plasmid, phage, or cosmid, into which another DNA segment may be inserted so as to bring about the replication of the inserted segment. The vectors can be expression vectors.

As used herein, an "expression vector" is a vector that includes one or more expression control sequences.

As used herein, an "expression control sequence" is a DNA sequence that controls and regulates the transcription and/or translation of another DNA sequence.

As used herein, "operably linked" means incorporated into a genetic construct so that expression control sequences effectively control expression of a coding sequence of interest.

As used herein, "transformed" and "transfected" encompass the introduction of a nucleic acid into a cell by a number of techniques known in the art.

As used herein "overproduced" means that the particular compound is produced at a higher quantity in the engineered organism as compared to the non-engineered organism.

As used herein the terms "renewable feedstock", "renewable carbon substrate" and "renewable substrate" are all used interchangeably.

"Plasmids" are designated by a lower case "p" preceded and/or followed by capital letters and/or numbers.

As used herein, the term "heterologous" means that a gene or gene fragment encoding a protein is obtained from one or more sources other than the genome of the species within which it is ultimately expressed. The source can be natural, e.g., the gene can be obtained from another source of living matter, such as bacteria, yeast, fungi and the like, or a different species of plant. The source can also be synthetic, e.g., the gene or gene fragment can be prepared in vitro by chemical synthesis. "Heterologous" can also be used in situations where the source of the gene fragment is elsewhere in the genome of the plant in which it is ultimately expressed.

As used herein, to say that an organism is "homologously" capable of a biochemical reaction, means that the organism naturally possesses the genetic and cellular machinery to undertake the stated reaction. For instance, an organism that is homologously capable of converting ethanol to acetyl-CoA is an organism that naturally is capable of doing so. Similarly, an organism that is homologously capable of producing polyhydroxyalkanoate polymer is an organism that is naturally capable of producing such polymers.

A "diol" is a chemical compound containing two hydroxyl (—OH) groups.

A "diacid" or dicarboxylic acid, is an organic compound that contains two carboxylic acid functional groups. These groups are often written as HOOC—R—COOH, where R may be an alkyl, alkenyl, alkynyl, or aryl group. Dicarboxylic acids can make up copolymers such as polyesters.

A "higher alcohol" (or secondary alcohol) is an alcohol containing more than two carbons.

As used herein "yield" refers to the amount of product per amount of carbon source (g/g or wt/wt). The maximal theoretical yield calculated by various techniques provides the greatest (maximum) yield (wt/wt) for any given biochemical process from carbon source to end-product. See below for examples.

Synthesis of Polyhydroxyalkanoate

During the mid-1980's, several research groups were actively identifying and isolating the genes and gene products responsible for PHA synthesis. These efforts led to the development of transgenic systems for production of PHAs in both microorganisms and plants, as well as enzymatic methods for PHA synthesis. Such routes could increase further the available PHA types. These advances have been reviewed in Williams & Peoples, *CHEMTECH*, 26:38-44 (1996) and Williams & Peoples, *Chem. Br.* 33:29-32 (1997).

Methods which can be used for producing PHA polymers suitable for subsequent modification to alter their rates of degradation are described, for example, in U.S. Pat. No. 4,910,145 to Holmes, et al.; Byrom, "Miscellaneous Biomaterials" in *Biomaterials* (Byrom, Ed.), pp. 333-59 (MacMillan Publishers, London 1991); Hocking & Marchessault, "Biopolyesters" in *Chemistry and Technology of Biodegradable Polymers* (Griffin, Ed.), pp. 48-96 (Chapman and Hall, London 1994); Holmes, "Biologically Produced (R)-3-hydroxyalkanoate Polymers and Copolymers," in *Develop-* ments in *Crystalline Polymers* (Bassett Ed.), vol. 2, pp. 1-65 (Elsevier, London 1988); Lafferty et al., "Microbial Production of Poly-b-hydroxybutyric acid" in *Biotechnology* (Rehm & Reed, Eds.) vol. 66, pp. 135-76 (Verlagsgesellschaft, Weinheim 1988); Muller & Seebach, *Angew. Chem. Int. Ed. Engl.* 32:477-502 (1993); Steinbuchel, "Polyhydroxyalkanoic Acids" in *Biomaterials* (Byrom, Ed.), pp. 123-213 (MacMillan Publishers, London 1991); Williams & Peoples, *CHEMTECH,* 26:38-44, (1996); Steinbuchel & Wiese, *Appl. Microbiol. Biotechnol.,* 37:691-697 (1992); U.S. Pat. Nos. 5,245,023; 5,250,430; 5,480,794; 5,512,669; and 5,534,432; Agostini, et al., *Polym. Sci., Part A*-1, 9:2775-87 (1971); Gross, et al., *Macromolecules,* 21:2657-68 (1988); Dubois, et al., *Macromolecules,* 26:4407-12 (1993); Le Borgne & Spassky, *Polymer,* 30:2312-19 (1989); Tanahashi & Doi, *Macromolecules,* 24:5732-33 (1991); Hori, et al., *Macromolecules,* 26:4388-90 (1993); Kemnitzer, et al., *Macromolecules,* 26:1221-29 (1993); Hori, et al., *Macromolecules,* 26:5533-34 (1993); Hocking, et al., *Polym. Bull.,* 30:163-70 (1993); Xie, et al., *Macromolecules,* 30:6997-98 (1997); U.S. Pat. No. 5,563,239 to Hubbs; U.S. Pat. Nos. 5,489,470 and 5,520,116 to Noda, et al. The PHAs derived from these methods may be in any form, including a latex or solid form.

Identification, cloning and expression of the genes involved in the biosynthesis of PHAs from several microorganisms within recombinant organisms allow for the production of PHAs within organisms that are not native PHA producers. A preferred example is *E. coli*, which is a well-recognized host for production of biopharmaceuticals, and PHAs for medical and other applications. Such recombinant organisms provide researchers with a greater degree of control of the PHA production process because they are free of background enzyme activities for the biosynthesis of unwanted PHA precursors or degradation of the PHA. Additionally, the proper selection of a recombinant organism may facilitate purification of or allow for increased biocompatibility of, the produced PHA.

Ethanol as a Feedstock

Biofuels, predominantly ethanol, dominate the production of biobased products worldwide. Although there is considerable interest in producing more advanced biofuels from renewable resources by far the simplest to produce is ethanol. Currently ethanol is produced at a scale of over 20 billion gallons per year through a combination of the fermentation of corn in the United States and sugar from sugarcane in Brazil. There is considerable effort to extend ethanol production to other renewable feedstocks including biomass such as straw, bagasse and wood as well as dedicated energy crops for example *Sorghum*, switchgrass, miscanthus and elephant grass. The use of these renewable resources has the potential to improve the overall energy balance of ethanol production and to separate biofuel production from the direct use of food crops. The overall economics of biomass based biorefineries will be dramatically improved by producing value added co-products including biobased chemicals and bioplastics in addition to biofuels such as ethanol. Clearly integrated biomass biorefineries based on cellulose hydrolysate technologies will optimize the separation of sugar feedstocks to maximize the product yields and economic and energy values. For this reason it is likely that some biomass biorefineries will produce only a mixed sugar stream containing primarily glucose (C6) and xylose (C5), whereas others will deploy different pre-treatment and hydrolysis conditions which enable the production of separate C6 and C5 streams. In the case of separate streams, the C6 stream can be readily converted to ethanol using existing industrial yeast strains without further genetic engineering. This then requires that the C5 sugar stream, which will contain at least 60%, 70%, 80%, 90%, 95%, 99% xylose has an end use consistent with the quantities that would typically be produced. As a general estimate a typical biomass facility producing separate sugar streams would produce around 1 ton of C5 sugars for every 3-5 tons of C6 sugars. A particularly attractive use of the clean C5 stream would be for the production of polyhydroxyalkanoate polymers, copolymers, diols, diacids and higher alcohols in microbes that are genetically engineered to produce these products as taught in the examples herein by replacing the ethanol feed with xylose (C5) sugars.

In addition there are efforts to produce ethanol directly from carbon dioxide using photosynthetic organisms including algae and cyanobacteria. Another source of carbon which is being developed is the use of waste streams such as municipal solid waste which can be converted to syngas (carbon monoxide, carbon dioxide and hydrogen) and then fermented to ethanol. Collectively these efforts to produce ethanol from renewable or waste carbon resources have the potential to make renewable resource based ethanol a very low cost high volume commodity feedstock which has many advantages for the production of other value added fermentation products in biorefineries. Ethanol production is well suited to using a wide range of relatively impure or complex feedstocks including for example dry mill corn or cellulose hydrolysate because it is volatile and hence readily recovered from complex fermentation broths through simple distillation. Microorganisms have been developed to produce ethanol from the complex sugar mixtures produced by the hydrolytic or thermal breakdown of cellulose and lignocellulose. These feedstocks typically contain both 5 carbon (C5, mostly xylose), and 6 carbon (C6, mostly glucose) sugars in the mix. In some biorefinery settings with for example wood based feedstocks it is relatively straightforward to separate the feedstocks to produce separate C5 and C6 feed streams. This opens the possibility of using these streams to produce different end products through fermentation. The C6 stream is well suited to the traditional ethanol process using industrial yeast strains. The C5 stream can be used separately to produce other value added biobased products such as for example the PHA polymers, diols, diacids, and higher alcohols described herein. Ethanol produced from the mixed C6 sugars can then also be used to practice the invention disclosed herein.

There are a number of advantages to being able to use ethanol over sugar as a feedstock for microbes producing polyhydroxyalkanoates and other chemicals. "Sugar" is actually a large class of compounds, of wildly varying types, concentrations, and purities. Ethanol's concentration and purity are more standardized and easily ascertainable than that of any sugar. Ethanol is already a standardized and widely transported feedstock in a number of industrial processes, and it is more logistically available than sugar. Ethanol also has a longer shelf life than sugar. Sugar cannot be sterilized when in solid form, so it must be dissolved in water for sterilization prior for introduction to the microbes. In contrast, ethanol is an alcohol, and is therefore self-sterilizing, and at certain concentrations, can be added to unsterilized water to produce a self-sterilizing sterile feedstock. To be added to a fermentation tank, sugar must first be dissolved in water. Adding it to a fermenter therefore increases the volume within the vessel after it is consumed by the microbes, as the residual water is left behind. In contrast, ethanol is already in liquid form, and adding it does not contribute additional water and volume to a fermenter after it is consumed. Use of ethanol in fed-batch fermentation processes may be especially advantageous in this regard, as it can be added over time, both reducing the risk of toxicity to the microbes, and obviating the need for a larger fermentation vessel.

Ethanol may be a more expensive feedstock for microbes than sugar, but the secondary costs associated with using sugar (shorter shelf life, sterilization requirements, and addition of diluent water to the fermentation tanks), may easily outweigh those costs. Moreover, production of ethanol is becoming less expensive as new industrial processes are refined. Having ethanol as a feedstock option for microbes producing polyhydroxyalkanoates and other chemicals therefore allows one to choose feedstocks in light of market availability and price.

A quantitative decision tree can be used for fermentation feedstock selection. Cost of a feedstock is a primary concern which drives the economic feasibility of a process. In general, the cost of a feedstock i ($C_i$) is related to the price of the feedstock i ($P_i$) and the yield of the product P from that feedstock ($Y_{P/i}$), such that:

$$C_i = \frac{P_i}{Y_{P/i}} \quad \text{(Equation - 1)}$$

For the substrates ethanol (E) and dextrose sugar (S), the equations read:

$$C_E = \frac{P_E}{Y_{P/E}} \quad \text{(Equation - 2)}$$

$$C_S = \frac{P_S}{Y_{P/S}} \quad \text{(Equation - 3)}$$

In some cases, the direct cost of the substrate is insufficient to capture the total cost of the system. In particular, the purity of the feedstock, feedstock concentration, byproducts, capital utilization, and the local availability of the resource dictate external costs which are not captured.

In comparing the cost parameters presented in Equations 2 and 3, a discount fraction ($f_{DIS}$) must be applied to capture the externalities. This variable represents the magnitude of the discount related to using the new feedstock. The range of the variable is 0 to 1, where a discount fraction of 0 represents no discount and a fraction of 1 represents a complete discount.

The cost ratio ($R_C$) is created to quantitatively determine the feedstock choice between two alternatives. This parameter is calculated in Equation—4, with dextrose sugar as the base feedstock choice and ethanol as the new feedstock choice.

$$R_C = (1 - f_{DIS})\frac{C_E}{C_S} = (1 - f_{DIS})\frac{P_E}{P_S}\frac{Y_{P/S}}{Y_{P/E}} \quad \text{(Equation - 4)}$$

If the cost ratio ($R_C$) is above 1, the costs increase when using the new feedstock and the base feedstock should be chosen. If the cost ratio is below 1, the costs decrease when using the new feedstock and the new feedstock should be chosen. At a cost ratio equal to one, the scenarios are equal and a decision is not determined.

One can also conduct an in silico analysis (model) of the biochemical networks for the production of *Escherichia coli* biomass from ethanol as a carbon source. A variety of techniques have been used by those of ordinary skill in the art to construct and simulate model biochemical networks for the purposes of calculating the maximum theoretical yield.

In planning the examples presented herein, a biochemical network was constructed using reactions annotated to known examples of *Escherichia coli* models, including model compositions for the biomass components (Edwards J, Ibarra R, Palsson B O, *Nat. Biotech.* 19:125-130 (2001); Reed J L, V O T D, Schilling C H, Palsson B O, *Genome Biology.* 4:R54 (2003)). The biochemical network was supplemented with additional reactions known to accommodate the utilization of ethanol, as described in Table 1.

A variety of analytical techniques were used to analyze this network for the maximum theoretical yield of biomass and biomass components from ethanol based on principles of mass and energy conservation (Clarke B L, *J. Chem. Phys.* 75:4970-4979 (1981); Roels J A, Energetics and kinetics in biotechnology, Elsevier, New York (1983); Reder C, *J. Theor. Biol.* 135:175-201 (1988); Schuster R, Schuster S, *CABIOS* 9:79-85 (1993)), including: thermodynamic free energy evaluation, extreme pathway analysis (Schilling C H, Letscher D, Palsson B, *J. Theor. Biol.* 203:229-248 (2000)), elementary mode analysis (Schuster S, Hilgetag S, *J. Biol. Syst.* 2:165-182 (1994); Schuster S, Dandekar T, Fell D A, *Trends Biotechnology* 17:53-60 (1999)), and flux balance analysis (Edwards J, Ibarra R, Palsson B O, *Nat. Biotech.* 19:125-130 (2001)).

These in silico scenarios indicated that supplementation of the *E. coli* network with the aforementioned reactions for the incorporation of ethanol is sufficient for growth on ethanol. The maximum theoretical yield was calculated as 0.72 (wt/wt) *E. coli* biomass per ethanol.

As shown in the examples below, ethanol-degrading genes can be identified from microbes capable of growing on ethanol as a carbon source, and transformed into *E. coli*, thus creating a strain of *E. coli* capable of growing on ethanol as a carbon source. This strain can then be further engineered to produce various useful products such as polyhydroxyalkanoates (including, but not limited to, polyglycolic acid (PGA), poly-3-hydroxybutyrate (P3HB), poly-3-hydroxypropionate (P3HP), poly-4-hydroxybutyrate (P4HB), poly-5-hydroxyvalerate (P5HV), poly-(3-hydroxybutyrate-co-4-hydroxybutyrate) (P3HB-co-4HB), poly-(3-hydroxybutyrate-co-5-hydroxyvalerate) (P3HB-co-5HV)), diols (including, but not limited to, 1,3-propanediol (1,3PD), 1,4-butanediol (1,4BD), 1,5-pentanediol (1,5PD), 1,6-hexanediol (1,6HD)), and other chemicals.

*Acinetobacter baylyi* is capable of growing on ethanol as a carbon source (see Example 1), and is therefore a candidate source of ethanol-degrading genes. However, publicly-available information on the metabolic pathways in *A. baylyi* provides conflicting information regarding the pathways involved in ethanol degradation. The database "MetaCyc" provides the following pathway:

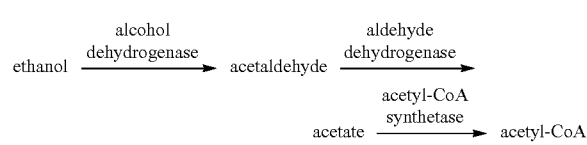

In contrast, the database "AcinetoCyc" provides the following pathway:

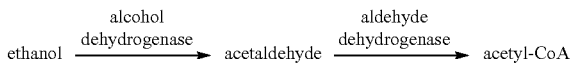

Corynebacterium glutamicum also grows on ethanol as a carbon source, and its two ethanol utilizing genes were used to search for corresponding genes in *A. baylyi*, revealing ACIAD3339 and ACIAD2018 (Example 2). When *Acinetobacter baumanii* was grown on ethanol, its two most up-regulated genes were identified, and used to search for corresponding genes in *A. baylyi*. This search revealed ACIAD2015 and ACIAD2018 (Example 2). ACIAD2018 was found to be the aldehyde dehydrogenase gene (ACIAD2018), but the identity of the alcohol dehydrogenase was still not clear. Additional experiments (Examples 3, 4) showed that ACIAD2015 was the ethanol dehydrogenase gene, and that the AcinetoCyc pathway was correct, while the MetaCyc pathway was not.

These genes were then cloned into broad host-range plasmids (Example 5). These plasmids were then used in conjunction with other plasmids to engineer host microorganisms to successfully utilize ethanol as a carbon source to make various useful products, including P3HB (Example 6), P4HB (Example 7), P3HP (Example 8), P4HV (Example 9), P3HB-co-4HB (Example 10), and P3HB-co-5HV (Example 11).

Suitable Host Strains

Recombinant organisms having enzymes for the biochemical pathways to convert ethanol to acetyl-CoA, and/or to produce useful products such as PHAs, diols, diacids, and higher alcohols, are provided. Host strains are genetically engineered to express the enzymes necessary to accomplish the metabolism of ethanol as a substrate, and the production of such useful products.

The host strain can be a bacterium, a fungus, an alga, or other microbe. Organisms of cells that can be modified for production of PHAs, diols, diacids and higher alcohols include prokaryotes and eukaryotes. Suitable prokaryotes include bacteria.

The host strain can be, for example, *Escherichia coli*. In certain embodiments, the host strain is *E. coli* K-12 strain LS5218 (Spratt et al., *J. Bacteriol.* 146 (3):1166-1169 (1981); Jenkins and Nunn, *J. Bacteriol.* 169 (1):42-52 (1987)) or DH5α (Raleigh et al., In: Ausubel et al., (Eds.) *Current Protocols in Molecular Biology*, p. 14 New York: Publishing Associates and Wiley Interscience (1989)). Other suitable *E. coli* K-12 host strains include, but are not limited to, MG1655 (Guyer et al., *Cold Spr. Harb. Symp. Quant. Biol.* 45:135-140 (1981)), WG1 and W3110 (Bachmann *Bacteriol. Rev.* 36(4):525-57 (1972)). Alternatively, *E. coli* strain W (Archer et al., *BMC Genomics* 2011, 12:9 doi: 10.1186/1471-2164-12-9) or *E. coli* strain B (Delbruck and Luria, *Arch. Biochem.* 1:111-141 (1946)) and their derivatives such as REL606 (Lenski et al., *Am. Nat.* 138:1315-1341 (1991)) are other suitable *E. coli* host strains.

Other exemplary microbial host strains include but are not limited to: *Ralstonia eutropha, Acinetobacter baumannii, Acinetobacter baylyi, Acinetobacter aceti, Acinetobacter sp. DR1, Acinetobacter calcoaceticus, Acinetobacter haemolyticus, Acinetobacter johnsonii, Acinetobacter junii, Acinetobacter lwoffii, Acinetobacter radioresistens, Acinetobacter venetianus, Acinetobacter sp. DSM, Zoogloea ramigera, Allochromatium vinosum, Rhodococcus ruber, Delftia acidovorans, Aeromonas caviae, Synechocystis sp. PCC 6803, Synechococcus elongatus PCC 7942, Thiocapsa pfenigii, Bacillus megaterium, Clostridium kluyveri, Methylobacterium extorquens, Nocardia corralina, Nocardia salmonicolor, Pseudomonas fluorescens, Pseudomonas oleovorans, Pseudomonas sp. 6-19, Pseudomonas sp. 61-3 and Pseudomonas putida, Rhodobacter sphaeroides, Alcaligenes latus, Klebsiella oxytoca, Anaerobiospirillum succiniciproducens, Actinobacillus succinogenes, Mannheimia succiniciproducens, Rhizobium etli, Bacillus subtilis, Corynebacterium glutamicum, Gluconobacter oxydans, Zymomonas mobilis, Lactococcus lactis, Lactobacillus plantarum, Streptomyces coelicolor,* and *Clostridium acetobutylicum*.

Exemplary yeasts or fungi include species selected from *Saccharomyces cerevisiae, Schizosaccharomyces pombe, Kluyveromyces lactis, Kluyveromyces marxianus, Aspergillus terreus, Aspergillus niger* and *Pichia pastoris*.

These include organisms that already produce polyhydroxyalkanoates, modified to utilize alternative substrates or incorporate additional monomers, or to increase production, and organisms that do not produce polyhydroxyalkanoates, but which express none to some of the enzymes required for production of polyhydroxyalkanoates. *R. eutropha* is an example of an organism which produces PHAs naturally. *E. coli* and *C. glutamicum* are examples of organisms where it would be necessary to introduce transgenes which encode the enzymes for PHA production.

Source of Recombinant Genes

Sources of encoding nucleic acids for an ethanol utilizing pathway enzyme can include, for example, any species where the encoded gene product is capable of catalyzing the referenced reaction. Such species include both prokaryotic and eukaryotic organisms including, but not limited to, bacteria (including archaea and eubacteria), and eukaryotes (including yeast, plant, insect, animal, and mammal, including human). Exemplary species for such sources include, for example, *Acinetobacter* species, including *Acinetobacter baumannii, Acinetobacter baylyi, Acinetobacter aceti, Acinetobacter sp. DR1, Acinetobacter calcoaceticus, Acinetobacter haemolyticus, Acinetobacter johnsonii, Acinetobacter junii, Acinetobacter lwoffii, Acinetobacter radioresistens, Acinetobacter venetianus, Acinetobacter sp. DSM,* and *Corynebacterium* species, including *Corynebacterium glutamicum, Corynebacterium diphtheriae, Corynebacterium xerosis, Corynebacterium striatum, Corynebacterium minutissimum, Corynebacterium amycolatum, Corynebacterium glucuronolyticum, Corynebacterium argentoratense, Corynebacterium matruchotii, Corynebacterium afermentans subsp. afermentans, Corynebacterium auris, Corynebacterium pseudodiphtheriticum, Corynebacterium propinquum, Corynebacterium jeikeium, Corynebacterium urealyticum, Corynebacterium afermentans subsp. lipophilum, Corynebacterium accolens, Corynebacterium macginleyi, Corynebacterium bovis,* and *Methylibium petroleiphilum* PM1, *Escherichia coli, Saccharomyces cerevisiae, Saccharomyces kluyveri, Clostridium kluyveri, Clostridium acetobutylicum, Clostridium beijerinckii, Clostridium saccharoperbutylacetonicum, Clostridium perfringens, Clostridium difficile, Clostridium botulinum, Clostridium tyrobutyricum, Clostridium tetanomorphum, Clostridium tetani, Clostridium propionicum, Clostridium aminobutyricum, Clostridium subterminale, Clostridium sticklandii, Ralstonia eutropha, Mycobacterium bovis, Mycobacterium tuberculosis, Porphyromonas gingivalis, Arabidopsis thaliana, Thermus thermophilus, Pseudomonas* species, including *Pseudomonas aeruginosa, Pseudomonas putida,*

Pseudomonas stutzeri, Pseudomonas fluorescens, Chlorella minutissima, Chlorella emersonii, Chlorella sorokiniana, Chlorella ellipsoidea, Chlorella sp., Chlorella protothecoides, Homo sapiens, Oryctolagus cuniculus, Rhodobacter spaeroides, Thermoanaerobacter brockii, Metallosphaera sedula, Leuconostoc mesenteroides, Chloroflexus aurantiacus, Roseiflexus castenholzii, Erythrobacter, Simmondsia chinensis, Porphyromonas gingivalis, Sulfolobus tokodaii, Sulfolobus solfataricus, Sulfolobus acidocaldarius, Bacillus subtilis, Bacillus cereus, Bacillus megaterium, Bacillus brevis, Bacillus pumilus, Rattus norvegicus, Klebsiella pneumonia, Klebsiella oxytoca, Euglena gracilis, Treponema denticola, Moorella thermoacetica, Thermotoga maritima, Halobacterium salina rum, Geobacillus stearothermophilus, Aeropyrum pernix, Sus scrofa, Caenorhabditis elegans, Corynebacterium glutamicum, Acidaminococcus fermentans, Lactococcus lactis, Lactobacillus plantarum, Streptococcus thermophilus, Enterobacter aerogenes, Candida, Aspergillus terreus, Pedicoccus pentosaceus, Zymomonas mobilis, Acetobacter pasteurians, Kluyveromyces lactis, Eubacterium barkeri, Bacteroides capillosus, Anaerotruncus colihominis, Natranaerobius thermophilusm, Campylobacter jejuni, Haemophilus influenzae, Serratia marcescens, Citrobacter amalonaticus, Myxococcus xanthus, Fusobacterium nuleatum, Penicillium chrysogenum marine gamma proteobacterium.

For example, microbial hosts (e.g., organisms) having the capability to utilize ethanol as a carbon source are exemplified herein with reference to an E. coli host. However, with the complete genome sequence available for now more than 550 species (with more than half of these available on public databases such as the NCBI), including 395 microorganism genomes and a variety of yeast, fungi, plant, and mammalian genomes, the identification of genes encoding the requisite ethanol utilization activity for one or more genes in related or distant species, including for example, homologues, orthologs, paralogs and non-orthologous gene displacements of known genes, and the interchange of genetic alterations between organisms is routine and well known in the art. Accordingly, the metabolic alterations enabling production of PHA and chemicals from ethanol as a carbon source described herein with reference to a particular organism such as E. coli can be readily applied to other microorganisms, including prokaryotic and eukaryotic organisms alike. Given the teachings and guidance provided herein, those skilled in the art will know that a metabolic alteration exemplified in one organism can be applied equally to other organisms.

Production of Transgenic Hosts

Transgenic (recombinant) hosts capable of utilizing ethanol as a carbon source are genetically engineered using conventional techniques known in the art. The genes cloned and/or assessed for host strains producing PHA and chemicals are presented below in Table 1A, along with the appropriate Enzyme Commission number (EC number) and references. Some genes can be synthesized for codon optimization or can be cloned via PCR from the genomic DNA of the native or wild-type host. As used herein, "heterologous" means from another host. The host can be the same or different species.

FIG. 1 is a schematic diagram showing the biochemical reaction from ethanol to acetyl-coenzyme A (Acetyl-CoA).

TABLE 1A

Genes in microbial host strains using ethanol as a carbon source.

| Reaction number (FIG. 1) | Enzyme Name | EC Number | Accession No. |
|---|---|---|---|
| 1 | alcohol dehydrogenase | 1.1.1.1 | ACIAD2015 |
| 2 | acetaldehyde dehydrogenase (acetylating) | 1.2.1.10 | ACIAD2018 |

Other proteins capable of catalyzing the reactions listed in Table 1A can be discovered by consulting the scientific literature, patents or by BLAST searches against e.g. nucleotide or protein databases at NCBI (www.ncbi.nlm.nih.gov/). Synthetic genes can then be created to provide an easy path from sequence databases to physical DNA. Such synthetic genes are designed and fabricated from the ground up, using codons to enhance heterologous protein expression, optimizing characteristics needed for the expression system and host. Companies such as e.g. DNA 2.0 (Menlo Park, Calif. 94025, USA) will provide such routine service. Proteins that may catalyze some of the biochemical reactions listed in Table 1A are provided in Tables 1B and 1C.

TABLE 1B

Suitable homologues for the Adh protein (alcohol dehydrogenase, from A. baylyi ADP1; EC No. 1.1.1.1, which acts on an alcohol such as ethanol to produce an aldehyde such as acetaldehyde; protein acc. no. ACIAD2015).

| Protein Name | Protein Accession No. |
|---|---|
| alcohol dehydrogenase | P33010 |
| alcohol dehydrogenase | Q64413 |
| alcohol dehydrogenase | Q70UP6 |
| alcohol dehydrogenase | P49385 |
| alcohol dehydrogenase | Q6LCE4 |
| alcohol dehydrogenase | Q4J781 |
| alcohol dehydrogenase | Q3Z550 |
| alcohol dehydrogenase | P85440 |
| alcohol dehydrogenase | P25141 |
| alcohol dehydrogenase | P04707 |

TABLE 1C

Suitable homologues for the Ald1 protein (acetaldehyde dehydrogenase (acetylating), from A. baylyi ADP1, EC No. 1.2.1.10, which acts on acetaldehyde to produce acetyl-CoA; protein acc. no. ACIAD2018).

| Protein Name | Protein Accession No. |
|---|---|
| acetaldehyde dehydrogenase (acetylating) | C1DMT1 |
| acetaldehyde dehydrogenase (acetylating) | A5V6T7 |
| acetaldehyde dehydrogenase (acetylating) | Q0S9X0 |
| acetaldehyde dehydrogenase (acetylating) | Q764S1 |
| acetaldehyde dehydrogenase (acetylating) | A4XAK8 |
| acetaldehyde dehydrogenase (acetylating) | A1UM81 |
| acetaldehyde dehydrogenase (acetylating) | A0R4S7 |
| acetaldehyde dehydrogenase (acetylating) | Q79AF6 |
| acetaldehyde dehydrogenase (acetylating) | B9LCM0 |
| acetaldehyde dehydrogenase (acetylating) | D1WHZ7 |

Suitable Extrachromosomal Vectors and Plasmids

A "vector," as used herein, is an extrachromosomal replicon, such as a plasmid, phage, or cosmid, into which another DNA segment may be inserted so as to bring about the replication of the inserted segment. Vectors vary in copy number and depending on the origin of their replication they contain, in their size, and the size of insert. Vectors with different origin of replications can be propagated in the same microbial cell unless they are closely related such as pMB1 and ColE1. Suitable vectors to express recombinant proteins can constitute pUC vectors with a pMB1 origin of replication having 500-700 copies per cell, pBluescript vectors with a ColE1 origin of replication having 300-500 copies per cell, pBR322 and derivatives with a pMB1 origin of replication having 15-20 copies per cell, pACYC and derivatives with a p15A origin of replication having 10-12 copies per cell, and pSC101 and derivatives with a pSC101 origin of replication having 2-5 copies per cell as described in the QIAGEN® Plasmid Purification Handbook (found on the world wide web at: //kirshner.med.harvard.edu/files/protocols/QIAGEN_QIAGENPlasmidPurification_EN.pdf). Another useful vector is the broad host-range cloning vector pBBR1MCS with a pBBR1 origin of replication and its derivatives that contain different antibiotic resistance cassettes (Kovach et al., *Gene* 166:175-176 (1995)). These vectors are compatible with IncP, IncQ and IncW group plasmids, as well as with ColE1- and p15A-based replicons.

Suitable Strategies and Expression Control Sequences for Recombinant Gene Expression Strategies for achieving expression of recombinant genes in *E. coli* have been extensively described in the literature (Gross, Chimica Oggi 7(3):21-29 (1989); Olins and Lee, *Cur. Op. Biotech.* 4:520-525 (1993); Makrides, *Microbiol. Rev.* 60(3):512-538 (1996); Hannig and Makrides, *Trends in Biotech.* 16:54-60 (1998)). Expression control sequences can include constitutive and inducible promoters, transcription enhancers, transcription terminators, and the like which are well known in the art. Suitable promoters include, but are not limited to, $P_{lac}$, $P_{tac}$, $P_{trc}$, $P_R$, $P_L$, $P_{trp}$, $P_{phoA}$, $P_{ara}$, $P_{uspA}$, $P_{rspU}$, $P_{tet}$, $P_{syn}$ (Rosenberg and Court, Ann. Rev. Genet. 13:319-353 (1979); Hawley and McClure, *Nucleic Acids Res.* 11 (8):2237-2255 (1983); Harley and Raynolds, *Nucleic Acids Res.* 15:2343-2361 (1987); also ecocyc.org and partsregistry.org).

Construction of Recombinant Hosts

Recombinant hosts containing the necessary genes that will encode the enzymatic pathway for the conversion of a carbon substrate such as e.g. ethanol to PHA and chemicals may be constructed using techniques well known in the art.

Methods of obtaining desired genes from a source organism (host) are common and well known in the art of molecular biology. Such methods can be found described in, for example, Sambrook et al., *Molecular Cloning: A Laboratory Manual*, Third Ed., Cold Spring Harbor Laboratory, New York (2001); Ausubel et al., *Current Protocols in Molecular Biology*, John Wiley and Sons, Baltimore, Md. (1999). For example, if the sequence of the gene is known, the DNA may be amplified from genomic DNA using polymerase chain reaction (Mullis, U.S. Pat. No. 4,683,202) with primers specific to the gene of interest to obtain amounts of DNA suitable for ligation into appropriate vectors. Alternatively, the gene of interest may be chemically synthesized de novo in order to take into consideration the codon bias of the host organism to enhance heterologous protein expression. Expression control sequences such as promoters and transcription terminators can be attached to a gene of interest via polymerase chain reaction using engineered primers containing such sequences. Another way is to introduce the isolated gene into a vector already containing the necessary control sequences in the proper order by restriction endonuclease digestion and ligation. One example of this latter approach is the BIOBRICK™ technology (see the world wide web at biobricks.org) where multiple pieces of DNA can be sequentially assembled together in a standardized way by using the same two restriction sites.

In addition to using vectors, genes that are necessary for the enzymatic conversion of a carbon substrate such as e.g. ethanol to PHA and chemicals can be introduced into a host organism by integration into the chromosome using either a targeted or random approach. For targeted integration into a specific site on the chromosome, the method generally known as Red/ET recombineering is used as originally described by Datsenko and Wanner (*Proc. Natl. Acad. Sci. USA*, 97:6640-6645 (2000)). Random integration into the chromosome involved using a mini-Tn5 transposon-mediated approach as described by Huisman et al. (U.S. Pat. Nos. 6,316,262 and 6,593,116).

Using the engineering methods described herein, one of ordinary skill in the art can (1) start with an organism capable of growing on ethanol as a carbon source and engineer it to make useful products as described herein, (2) start with an organism capable of making useful products and engineer it to be capable of growing on ethanol as a carbon source, or (3) start with an organism, and engineer it to be capable of growing on ethanol as a carbon source and engineer it to make useful products as described herein.

For instance, one can start with an organism such as *Acinetobacter baylyi*, which is known to utilize ethanol as a carbon source, and engineer it according to methods described herein to make useful products. Alternatively, one can start with an organism such as *Ralstonia eutropha*, which is known to make polyhydroxyalkanoate polymers, and engineer it as described herein to grow on ethanol as a carbon source. Also shown below are microbes that neither use ethanol nor make polyhydroxyalkanoates naturally, and are engineered to utilize ethanol as a carbon source and make polyhydroxyalkanoates and other useful products.

Methods of culturing such engineered organisms to produce useful products are known in the art. To make some products, co-feeds besides ethanol may be required, for instance, depending on the pathway(s) engineered into the organism, a co-feed of propionate or propanol may be required to produce polymers containing 3-hydroxyvalerate. For polymers containing 4-hydroxybutyrate, a co-feed of 1,4-butanediol or gamma butyrolactone may be needed. For copolymers containing 5-hydroxyvalerate, a co-feed of 5-hydroxyvalerate or 1,5-pentanediol could be required.

EXAMPLES

Example 1

Growth of *Acinetobacter baylyi* ADP1 on Ethanol

This example shows the ability of *Acinetobacter baylyi* ADP1 utilizing ethanol as a carbon source.

A single colony of *A. baylyi* ADP1 was inoculated into 3 mL of LB medium (1.0% Tryptone, 0.5% Yeast Extract, 1.0% NaCl, pH 7.0) and grown over night in an orbital shaker at 37° C. Thirty μL of the preculture was then transferred into the production medium which consisted of 1×E2 minimal salts solution containing 2 mM $MgSO_4$, 1× Trace Salts Solution and 0.1% (v/v) of ethanol. 50×E2 stock solution consists of 1.275 M $NaNH_4HPO_4.4H_2O$, 1.643 M $K_2HPO_4$, and 1.36 M $KH_2PO_4$. 1000× stock Trace Salts Solution is prepared by adding per 1 L of 1.5 NHCL: 50 g $FeSO_4.7H_2O$, 11 g $ZnSO_4.7H_2O$, 2.5 g $MnSO_4.4H_2O$, 5 g $CuSO_4.5H_2O$, 0.5 g $(NH_4)_6Mo_7O_{24}.4H_2O$, 0.1 g $Na_2B_4O_7$, and 10 g $CaCl_2.2H_2O$.

The doubling time was calculated to be about 30 min and reached a final OD$_{600}$ of 1.15 demonstrating that *A. baylyi* ADP1 contains genes that enable growth on ethanol as a carbon source.

Example 2

Identification of Putative Ethanol Utilizing Genes in *Acinetobacter*

Publicly-available metabolic databases provided conflicting information regarding the pathway for converting ethanol to acetyl-CoA.

Examination of MetaCyc, a database of nonredundant, experimentally elucidated metabolic pathways containing more than 1600 pathways from more than 2000 different organisms (found at http://metacyc.org/), indicated that three biochemical reactions in *A. baylyi* ADP1 convert ethanol to acetyl-CoA: (a) ethanol to acetaldehyde using an alcohol dehydrogenase (EC 1.1.1.1), (b) acetaldehyde to acetate using an aldehyde dehydrogenase (EC 1.2.1.3), and (c) acetate to acetyl-CoA using an acetyl-CoA synthetase (EC 6.2.1.1). In contrast, examination of AcinetoCyc, a pathway genome database dedicated to *A. baylyi* ADP1 (found on the world wide web at genoscope.cns.fr/acinetocyc), indicated that only two biochemical reactions are required: (a) ethanol to acetaldehyde using an alcohol dehydrogenase (EC 1.1.1.1) and (b) acetaldehyde to acetyl-CoA using an acetaldehyde dehydrogenase (acetylating) (EC 1.2.1.10). \Table 2 provides an overview of the gene candidates as identified by MetaCyc and AcinetoCyc. Since both public pathway databases indicate different biochemical reactions and multiple annotated gene candidates, it is unclear which reactions and genes enable cell growth on ethanol as a carbon source.

TABLE 2

Gene candidates for ethanol degradation listed by MetaCyc and AcinetoCyc

| EC number and Enzyme Name | MetaCyc Gene Candidates | AcinetoCyc Gene Candidates |
|---|---|---|
| 1.1.1.1 alcohol dehydrogenase | ACIAD3339 (adhA) ACIAD1950 ACIAD2015 ACIAD2929 | ACIAD3339 (adhA) ACIAD1950 ACIAD2015 ACIAD2929 |
| 1.2.1.3 Aldehyde dehydrogenase | ACIA2018 (ald1) ACIAD0131 ACIAD2542 | NA |
| 1.2.1.10 Acetaldehyde dehydrogenase (acetylating) | NA | ACIA2018 (ald1) ACIA3616 (alrA) |
| 6.2.1.1 acetate-CoA ligase | ACIAD3475 (acs) ACIAD1606 ACIAD1611 | NA |

*Corynebacterium glutamicum* was shown to be able to grow on ethanol as a carbon source and the two ethanol-utilizing genes were identified as Cg3107 encoding ethanol dehydrogenase (EC 1.1.1.1) and Cg3096 encoding aldehyde dehydrogenase (EC 1.2.1.3) (Arndt and Eikmanns, *J. Bacteriol.* 189(20):7408-7416 (2007)); Auchter et al., *J. Biotechnol.* 140:84-91 (2009); Arndt et al., *J. Mol. Microbiol. Biotechnol.* 15:222-233 (2008)). BLASTP searches (Altschul, *J. Mol. Biol.* 219:555-65 (1991)) using the protein sequences of Cg3107 and Cg3096 against the protein sequences of *A. baylyi* ADP1 identified ACIAD3339 and ACIAD2018, respectively, as best hits for ethanol dehydrogenase and aldehyde dehydrogenase.

Global gene expression profiles of the pathogenic *A. baumannii* were analyzed under ethanol-induced pathogenesis and compared to glucose growth conditions (Camarena et al., *PLoS Pathog.* 6(4):e1000834. doi:10.1371/journal.ppat.1000834). The two most up-regulated genes under ethanol-induced conditions were A1S_2098 and A1S_2102, which are annotated as ethanol dehydrogenase and aldehyde dehydrogenase, respectively. BLASTP searches using the protein sequences of A1S_2098 and A1S_2102 against the protein sequences of *A. baylyi* ADP1 identified ACIAD2015 and ACIAD2018 as best hits for alcohol dehydrogenase and aldehyde dehydrogenase, respectively.

From these two lines of experimental evidence, it seems clear that ACIAD2018 is the best candidate for aldehyde dehydrogenase. But it remains unclear which alcohol dehydrogenase enables growth on ethanol, ACIAD3339 or ACIAD2015.

Example 3

Identification of Alcohol Dehydrogenase in *A. baylyi* ADP1 by Gene Knock-Out

In order to experimentally verify which of the two alcohol dehydrogenase genes from *A. baylyi* ADP1 (ACIAD3339 or ACIAD 2015) is responsible for growth on ethanol as a carbon source, individual gene knock-outs of ACIAD3339 and ACIAD2015 were constructed.

The coding sequences of the native genes were replaced by the kanamycin resistance marker using well known molecular biology techniques as described by Metzgar et al. (*Nucleic Acids Res.* 32:5780-5790 (2004)) and de Berardinis et al. (*Mol. Syst. Biol.* 4:174; doi:10.1038/msb.2008.10. (2008); Young et al., *Annu. Rev. Microbiol.* 59:519-551 (2005)). The two gene knock-out strains were first grown over night in 3 mL tubes containing LB medium (see Example 1 for composition) supplemented with 50 ug/mL kanamycin at 37° C. and then inoculated at a 1:100 dilution into 1×E2 medium supplemented with 0.5% ethanol and 50 ug/mL kanamycin. Both E2 medium and trace elements are described in Example 1. As a control, the wild-type strain was included.

Figure 2:
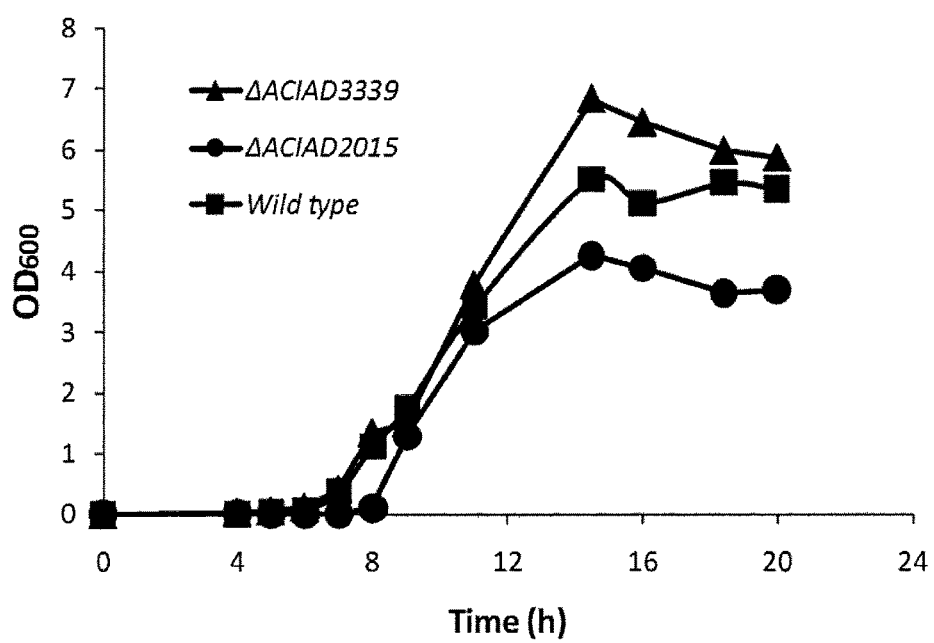
FIG. 2 is a graph showing growth curves of *A. baylyi* ADP1 wild-type strain (■) and its single gene knock-out mutants (ΔACIAD3339 (▲) and ΔACIAD2015 (•)) in 1×E2 medium supplemented with 0.5% (v/v) ethanol.

The growth profile is shown in FIG. 2 and shows that only the deletion of ACIAD2015 exhibited a measurable growth defect on ethanol with a longer lag phase and a lower final OD$_{600}$. This result indicates that more than one alcohol dehydrogenase enables growth on ethanol and that ACIAD2015 seems to be more important for ethanol degradation than ACIAD3339.

Example 4

Heterologous Expression of Putative Alcohol Degradation Genes in *E. coli*

In this example, the alcohol dehydrogenase and aldehyde dehydrogenase gene combinations of ACIAD3339+ACIAD2018 and ACIAD2015+ACIAD2018 were tested against each other. As shown below, it was found that ACIAD2015 and ACIAD2018 support growth on ethanol as a carbon source.

The two *A. baylyi* ADP1 genes ACIAD3339 and ACIAD2018 were cloned into a vector in *E. coli* and expressed from the P$_{tet}$ promoter. This plasmid was constructed in a three step process. First, the ACIAD3339 and ACIAD2018 genes were PCR-amplified individually from a genomic DNA preparation from *A. baylyi* ADP1 using primers ZZ212/ZZ213 yielding PCR product 1 and ZZ214/ZZ215 yielding PCR product 2, respectively (Table 3). Primers ZZ212 and ZZ215 were designed to incorporate BamHI and BspHI restriction sites, respectively, on their 5' ends. The sequences of primers ZZ213 and ZZ214 are reverse-complementary so that the sequences of 39 bps of 3'-end ACIAD3339 fragment (PCR product 1) and 39 bps of 5'-end ACIAD2018 fragment (PCR product 2) were the same. Following the method of Murphy et al., (Gene 246: 321-330 (2000)), the two DNA fragments were sewed together by PCR simply using small amounts of PCR products 1 and 2 as template without additional primers, yielding PCR product 3. Finally, the PCR product 3 containing the two amplified ACIAD3339 and ACIAD2018 genes in an operon was digested with BamHI and BspHI and ligated to pJB78, a pACYC184 derivative vector (Farmer et al., US Patent Application No. 2010/0168481 A1) that had been digested with the same enzymes, thus creating plasmid pZZ9 which expressed the ACIAD3339 and ACIAD2018 genes in an operon under the control of the constitutive $P_{tet}$ promoter.

TABLE 3

Primers used in Example 4.

| Primer | Sequence (5' → 3') |
|---|---|
| ZZ212 | CCCGGATCCAGGAGGTTTTTATGGGAAGTTTAATGAAAGC (SEQ ID NO: 1) |
| ZZ213 | TCGATATAACGCATAAAAACCTCCTTTAGAGTTTAAGGTCAATCA (SEQ ID NO: 2) |
| ZZ214 | ACCTTAAACTCTAAAGGAGGTTTTTATGCGTTATATCGATCCTAA (SEQ ID NO: 3) |
| ZZ215 | CCCTCATGATTAGAAGAAGCCCATTGGTT (SEQ ID NO: 4) |
| ZZ226 | CCCGACGTCAGGAGGTTTTTATGGCTTTTAAAAATATTGCTGACC (SEQ ID NO: 5) |
| ZZ227 | AACGCATAAAAACCTCCTTCTAGGTTTACAATGCTGCTGTGAAAA (SEQ ID NO: 6) |
| ZZ228 | ATTGTAAACCTAGAAGGAGGTTTTTATGCGTTATATCGATCCTAA (SEQ ID NO: 7) |
| ZZ229 | GGGCCCGGGTTAGAAGAAGCCCATTGGTTTTGTT (SEQ ID NO: 8) |

Plasmid pZZ9 was transformed into E. coli strain DH5α and the resulting strain was first grown in LB supplemented with 25 μg/mL chloramphenicol over night at 37° C. and was then inoculated 1:100 into 1×E2 minimal medium supplemented with 0.1% (v/v) ethanol and 25 μg/mL chloramphenicol at 37° C. Both E2 medium and trace elements are described in Example 1. After 24 h of incubation no measurable cell growth was detected.

Since the two A. baylyi ADP1 genes ACIAD3339 and ACIAD2018 did not support growth on ethanol as a carbon source, the two A. baylyi ADP1 genes ACIAD2015 and ACIAD2018 were cloned. This plasmid was made similarly as pZZ9. First, the ACIAD2015 and ACIAD2018 genes were PCR-amplified individually from a genomic DNA preparation using primers ZZ226/ZZ227 yielding PCR product 1 and ZZ228/ZZ229 yielding PCR product 2, respectively. Primers ZZ226 and ZZ229 were designed to incorporate AatII and XmaI restriction sites, respectively, on their 5' ends. The sequences of primers ZZ227 and ZZ228 are reverse-complementary so that the sequences of 32 bps of 3'-end ACIAD2015 fragment (PCR product 1) and 32 bps of 5'-end ACIAD2018 fragment (PCR product 2) were the same. Following the method of Murphy et al., (Gene 246: 321-330 (2000)), the two DNA fragments were sewed together by PCR simply using small amounts of PCR products 1 and 2 as template without additional primers, yielding PCR product 3. Finally, the PCR product 3 containing the two amplified ACIAD2015 and ACIAD2018 genes in an operon was digested with AatII and XmaI and ligated to pJB78 that had been digested with the same enzymes. The resulting plasmid expressed the ACIAD2015 and ACIAD2018 genes in an operon under the control of the constitutive $P_{tet}$ promoter.

The plasmid was transformed into E. coli strain DH5α and two clones were tested for their ability to grow on ethanol as a carbon source. The strains were first grown in LB supplemented with 25 μg/mL chloramphenicol over night at 37° C. and were then inoculated 1:100 into 1×E2 minimal medium supplemented with 0.1% (v/v) ethanol and 25 μg/mL chloramphenicol at 37° C. After 24 h of incubation one clone (clone 6) reached an $OD_{600}$ of 0.3 whereas, surprisingly, the other one (clone 7) reached on $OD_{600}$ of 1.25. DNA sequence analysis confirmed that clone 6 exhibited the correct DNA sequence of the cloned ethanol-utilizing genes. However, clone 7 contained a deletion in the Shine-Dalgarno (SD) sequence of ACIAD2015. The intended SD sequence of ACIAD2015 in clone 6 was 5'-AGGAGG-3', whereas the mutated SD sequence of ACIAD2015 in clone 7 was 5'-AG_AGG-3'. The plasmid of clone 7 was named pZZ10 and the plasmid of clone 6 was named pZZ12.

Example 5

Cloning of Ethanol Degradation Genes into Broad Host-Range Plasmids

To enable production of various PHA and chemicals in E. coli and various other microbes, the ethanol-degradation genes ACIAD2015 and ACIAD2018 were cloned into the broad host-range vector pBBR1MCS and its derivatives (Kovach et al., Gene 166:175-176 (1995)). Plasmids pZZ17, pZZ18 and pZZ22 were made by first PCR-amplifying the $P_{tet}$-ACIAD2015-ACIAD2018 operon from plasmid pZZ10 using primers ZZ235 and ZZ236, which were designed to incorporate SalI and SacI restriction sites on their 5' ends, respectively. The resulting PCR product was digested with SalI and SacI and ligated to similarly digested broad host-range vectors pSS7 (kanamycin-resistant (Km)) creating pZZ17, to pBBR1MCS-4 (ampicillin-resistant ($Ap^R$)) (GenBank Accession No. U25060) creating pZZ18, and to pBBR1MCS (chloramphenicol-resistant ($Cm^R$)) (GenBank Accession No. U02374) creating pZZ22, respectively. Vector pSS7 ($Km^R$) was made by PCR-amplification of the kan cassette from pKD4 (Datsenko and Warmer, Proc. Natl. Acad. Sci. USA. 97:6640-6645 (2000)) with primers SS62 and SS63 (Table 4), which were engineered to introduce ApaLI and ScaI restriction sites, respectively. Then the PCR product was digested with ApaLI and ScaI and cloned into pBBR1MCS-4 ($Ap^R$) vector that were digested with the same enzymes to generate pSS7 ($Km^R$). Plasmid pZZ23 was constructed by first PCR-amplifying the $P_{tet}$-ACIAD2015-ACIAD2018 operon from plasmid pZZ10 using primers ZZ268 and ZZ236, which contains XbaI and SacI restriction sites on their 5' ends, respectively. The resulting PCR product was digested with XbaI and SacI and ligated to similarly digested broad host-range vector pBBR1MCS-3 (tetracycline-resistant (Tc$^R$)) (GenBank accession No. U25059) creating pZZ23. All these broad host-range plasmids containing the different antibiotic resistances are compatible with ColE1- and p15A-based replicons (Kovach, et al., Gene 166:175-176 (1995)).

TABLE 4

Primers used in Example 5.

| Primer | Sequence (5' → 3') |
|---|---|
| SS62 | ATGCGTGCACGTGTAGGCTGGAGCTGCTTC (SEQ ID NO: 9) |
| SS63 | ATGCAGTACTATGGGAATTAGCCATGGTCC (SEQ ID NO: 10) |
| ZZ235 | CCCGTCGACAATTCTCATGTTTGACAGCTT (SEQ ID NO: 11) |
| ZZ236 | CCCGAGCTCTTAGAAGAAGCCCATTGGTTT (SEQ ID NO: 12) |
| ZZ268 | CCCTCTAGAAATTCTCATGTTTGACAGCTT (SEQ ID NO: 13) |

Example 6

P3HB Production From Ethanol as a Carbon Source in Recombinant *E. coli* Cells

Figure 3:
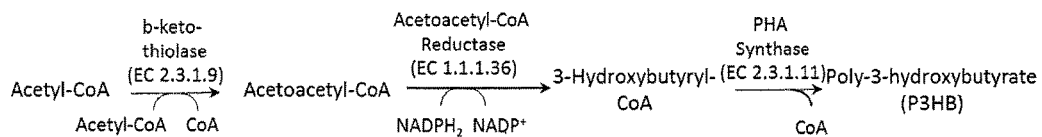
FIG. 3 is a diagram showing the pathway from acetyl-CoA to poly-3-hydroxybutyrate (P3HB).

This example shows poly-3-hydroxybutyrate (P3HB) production from ethanol as a carbon source in recombinant *E. coli* cells. The pathway from acetyl-CoA to P3HB is shown in FIG. 3, and involves the phaA$_5$, phaB$_5$ and phaC$_3$/C$_5$ genes to convert acetyl-CoA to acetoacetyl-CoA (via beta-ketothiolase (PhaA$_5$)), acetoacetyl-CoA to 3-hydroxybutyryl-CoA (via acetoacetyl-CoA reductase (PhaB$_5$)), and 3-hydroxybutyryl-CoA to P3HB (via PHA synthase (PhaC$_3$/C$_5$)).

To produce P3HB from ethanol as a carbon source in recombinant *E. coli* cells, a derivative strain of LS5218 (Jenkins and Nunn, *J. Bacteria* 169:42-52 (1987)) was used that expressed the phaA$_5$, phaB$_5$ and phaC$_3$/C$_5$ genes as described previously by Huisman et al. (U.S. Pat. No. 6,316,262). To enable growth on ethanol as the carbon source, plasmid pZZ18 containing the P$_{tet}$-ACIAD2015-ACIAD2018 operon in pBBR1MCS-4 (Ap$^R$) was transformed into this strain, resulting in strain MBX4900. These gene modifications and host strains are shown in Tables 5 and 6, below.

TABLE 5

Microbial strain used to produce P3HB from ethanol as sole carbon source.

| Strain | Relevant host genome modifications |
|---|---|
| MBX4900 | P$_{12}$-phaA$_5$-phaB$_5$-kan; phaC$_3$/C$_5$-cat |

TABLE 6

Genes in microbial host strains producing P3HB.

| Gene Name | Enzyme Name | EC Number | Reference |
|---|---|---|---|
| phaA$_5$ | β-ketoacyl-CoA thiolase | 2.3.1.9 | U.S. Pat. No. 6,316,262 |
| phaB$_5$ | acetoacetyl-CoA reductase | 1.1.1.36 | U.S. Pat. No. 6,316,262 |
| phaC$_3$/C$_5$ | Polyhydroxyalkanoate synthase fusion protein | 2.3.1.n | U.S. Pat. No. 6,316,262 |

To examine production of 3HB homopolymer from ethanol, strain MBX4900 was cultured for 7 h in a sterile tube containing 3 mL of LB supplemented with 100 µg/mL ampicillin and 25 µg/mL chloramphenicol. Then 60 µL was added to a sterile tube containing 3 mL of 1×E2 medium supplemented with 1.0% (v/v) ethanol and 100 µg/mL ampicillin and 25 µg/mL chloramphenicol. Both E2 medium and trace elements are described in Example 1. The tube cultures were incubated over night with shaking at 250 rpm at 37° C. From this, 25 µL was added as seeds in triplicate to Duetz deep-well shake plate wells containing 475 µL of 1×E2 medium supplemented with 2.0% (v/v) ethanol and 100 µg/mL ampicillin and 25 µg/mL chloramphenicol. The cells were grown for 6 h at 37° C. followed by 42 h at 30° C. with shaking at 250 rpm. Thereafter, production well sets were combined (1.5 mL total) and analyzed for polymer content. At the end of the experiment, cultures were spun down at 4150 rpm, washed twice with distilled water, frozen at −80° C. for at least 30 minutes, and lyophilized overnight. The next day, a measured amount of lyophilized cell pellet was added to a glass tube, followed by 3 mL of butanolysis reagent that consisted of an equal volume mixture of 99.9% n-butanol and 4.0 N HCl in dioxane with 2 mg/mL diphenylmethane as internal standard. After capping the tubes, they were vortexed briefly and placed on a heat block set to 110° C. for 3 h with periodic vortexing. Afterwards, the tube was cooled down to room temperature before adding 3 mL distilled water. The tube was vortexed for approximately 10 s before spinning down at 620 rpm (Sorvall Legend RT benchtop centrifuge) for 2 min. One mL of the organic phase was transferred into a GC vial, which was then analyzed by gas chromatography-flame ionization detection (GC-FID) (Hewlett-Packard 5890 Series II).

The quantity of P3HB homopolymer in the cell pellet was determined by comparing against standard curves that were made by adding defined amounts of P(3HB) (Aldrich Chemical Co., Milwaukee Wis.) in separate butanolysis reactions. Four 3HB standards ranging from 0.5-10 mg were used to create the standard curves. Strain MBX4900 produced a total biomass titer of 3.96±0.07 g/L from 2.0% (v/v) of ethanol, containing 32.19±1.45% (dry cell weight (dcw)) of P3HB.

Example 7

P4HB Production from Ethanol as a Carbon Source in Recombinant *E. coli* Cells

Figure 4:
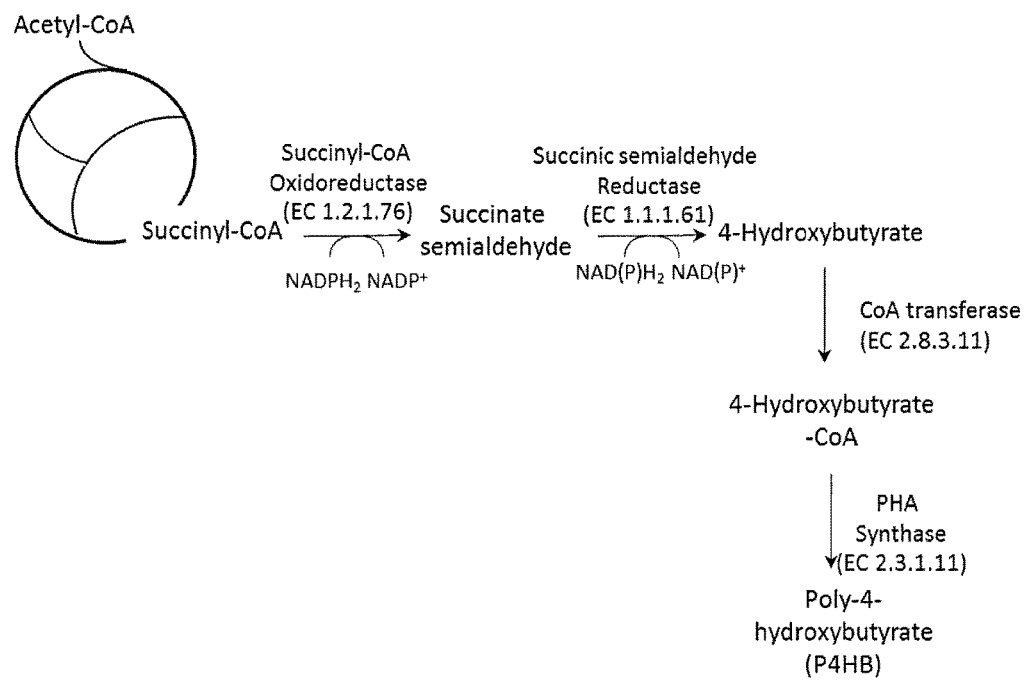
FIG. 4 is a diagram showing the pathway from acetyl-CoA and succinyl-CoA to poly-4-hydroxybutyrate (P4HB).

This example illustrates poly-4-hydroxybutyrate (P4HB) production from ethanol as the carbon source in recombinant *E. coli* cells. The pathway from acetyl-CoA to P4HB is shown in FIG. 4. Acetyl-CoA is naturally converted to succinyl-CoA by the organism, and so no engineering is required to convert acetyl-CoA to succinyl-CoA. The pathway from succinyl-CoA to P4HB includes the conversion of succinyl-CoA to succinate semialdehyde (via succinyl-CoA oxidoreductase), succinate semialdehyde to 4-hydroxybutyrate (via succinate semialdehyde reductase), 4-hydroxybutyrate to 4-hydroxybutyrate-CoA (via CoA transferase), and 4-hydroxybutyrate-CoA to P4HB (via PHA synthase).

To produce P4HB from ethanol as a carbon source in recombinant E. coli cells, a derivative strain of LS5218 was used that contains chromosomal deletions of the native genes gabD and yneI and expresses a CoA-transferase gene orfZ from Chlostridium kluyveri. Single null gabD and yneI mutants were constructed as described by Farmer et al. (US Patent Application No. 2010/0168481 A1) and used the Red/ET recombineering method originally described by Datsenko and Wanner (Proc. Natl. Acad. Sci. USA 97:6640-6645 (2000)), a method well known for those skilled in the art. Expression of orfZ involved a mini-Tn5 transposon-mediated approach described by Huisman et al. (U.S. Pat. Nos. 6,316,262 and 6,593,116). To produce P4HB from ethanol, 3 plasmids were individually transformed into strain LS5218 resulting in strain MBX4978 that expressed the recombinant genes outlined in Table 7. The source of the recombinant genes is listed in Table 8.

TABLE 7

Microbial strain used to produce P4HB from ethanol as a carbon source. A star (*) after the gene name denotes that the nucleotide sequence was optimized for expression in E. coli.

| Strain | Relevant host genome modifications | Genes overexpressed from a plasmid | Plasmid origin of replication |
|---|---|---|---|
| MBX4978 | ΔyneI ΔgabD $P_{rpsU}$-orfZ | $P_{sym1}$-sucD*-ssaR$_{At}$* $P_{tet}$-phaC1 $P_{tet}$-ACIAD2015-ACIAD2018 | ColE1 (Ap$^R$) p15A (Cm$^R$) pBBR1 (Km$^R$) |

TABLE 8

Genes in microbial host strains producing P4HB and 4HB copolymer. A star (*) after the gene name denotes that the nucleotide sequence was optimized for expression in E. coli.

| Gene Name | Enzyme Name | EC Number | Accession No. |
|---|---|---|---|
| sucD* | Succinate semialdehyde dehydrogenase | 1.2.1.76 | YP_001396394 |
| ssaR$_{At}$* | Succinic semialdehyde reductase | 1.1.1.61 | AAK94781 |
| orfZ | CoA transferase | 2.8.3.n | AAA92344 |
| phaC1 | Polyhydroxyalkanoate synthase | 2.3.1.n | YP_725940 |
| yneI | Succinate-semialdehyde dehydrogenase, NADP+-dependent | 1.2.1.24 | NP_416042 |
| gabD | Succinate-semialdehyde dehydrogenase, NADP+-dependent | 1.2.1.16 | NP_417147 |

To produce P4HB from ethanol, strain MBX4978 was grown in a 53 h shake plate assay. The seeds culture was prepared the same way as described in Example 6. The production medium consisted of 1×E2 minimal salts solution containing 3.0% (v/v) of ethanol, 1× Trace Salts Solution and appropriate antibiotics (100 μg/mL ampicillin, 25 μg/mL chloramphenicol and 50 μg/mL kanamycin). Both E2 medium and trace elements are described in Example 1. At the end of the growth phase, the biomass and P4HB titers were determined as described previously (Van Walsem et al., International Publication No. WO/2011/100601). The P4HB content was measured by gas chromatography-flame ionization detection (GC-FID) (Hewlett-Packard 5890 Series II) and the identity of the 4HB monomer was further confirmed by GC-MS (Agilent GC model 6890N and Agilent MS model 5973).

Strain MBX4978 produced a total biomass titer of 2.59±0.02 g/L from 3.0% (v/v) of ethanol, containing 0.48±0.02% (dcw) of P4HB.

Example 8

P3HP Production From Ethanol as a Carbon Source in Recombinant E. coli Cells

Figure 5:
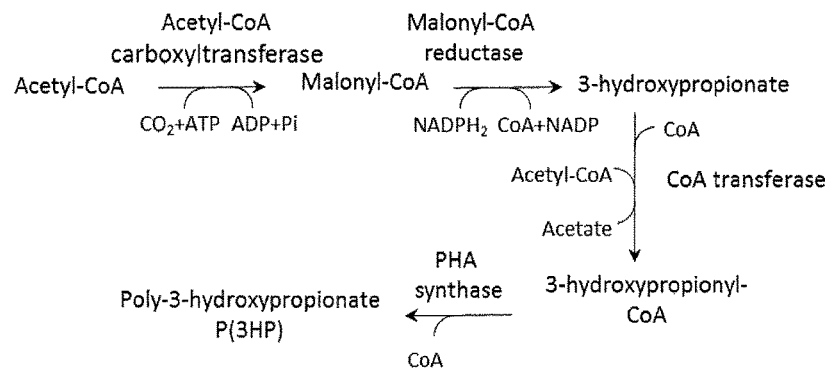
FIG. 5 is a diagram showing the pathway from acetyl-CoA to poly-3-hydroxypropionate (P3HP).

This example demonstrates poly-3-hydroxypropionate (P3HP) production from ethanol as a carbon source in recombinant E. coli cells. This pathway is shown in FIG. 5, and involves the conversion of acetyl-CoA to malonyl-CoA (via acetyl-CoA carboxyltransferase), malonyl-CoA to 3-hydroxypropionate (via malonyl-CoA reductase), 3-hydroxypropionate to 3-hydroxypropionyl-CoA (via CoA transferase), and 3-hydroxypropyl-CoA to P3HP (via PHA synthase).

To produce P3HP from ethanol as a carbon source in recombinant E. coli cells, a derivative strain of LS5218 was used harboring 2 plasmids resulting in strain MBX4938 that expressed the recombinant genes outlined in Table 9. The sources of the recombinant genes are listed in Table 10.

TABLE 9

Microbial strain used to produce P3HP from ethanol as a carbon source. A star (*) after the gene name denotes that the nucleotide sequence was optimized for expression in E. coli.

| Strain | Relevant host genome modifications | Genes overexpressed from a plasmid | Plasmid origin of replication |
|---|---|---|---|
| MBX4938 | $P_{rpsU}$-orfZ | $P_{trc}$-mcr*-phaC3/C1* $P_{tet}$-ACIAD2015-ACIAD2018 | ColE1 (Ap$^R$) pBBR1 (Km$^R$) |

TABLE 10

Genes in microbial host strains producing P3HP. A star (*) after the gene name denotes that the nucleotide sequence was optimized for expression in E. coli.

| Gene Name | Enzyme Name | EC Number | Accession No. or Reference |
|---|---|---|---|
| mcr* | malonyl-CoA reductase | 1.1.1.298 | Q6QQP7; Gene ID 001 |
| phaC3/C1* | Polyhydroxyalkanoate synthase fusion protein | 2.3.1.n | Van Walsem et al., International Application No PCT/US11/024612 |

To produce P3HP from ethanol, strain MBX4938 was grown in a 103 h shake plate assay. The seeds culture was prepared the same way as described in Example 6. The production medium consisted of 1×E2 minimal salts solution containing either 2.0% or 3.0% (v/v) of ethanol, 1× Trace Salts Solution, 0.1 mM IPTG and appropriate antibiotics (100 μg/mL ampicillin and 50 μg/mL kanamycin). The initial ethanol concentration was 2.0% (v/v) for both, but 1.0% (v/v) ethanol was added at 27 h for one of the cultures. Both E2 medium and trace elements are described in Example 1. At the end of the growth phase, the biomass and P3HP titers were determined as described previously (Skraly and Peoples, U.S. Pat. No. 6,329,183).

Strain MBX4938 produced a total biomass titer of 0.73±0.21 g/L from 2.0% (v/v) ethanol, containing 2.83±0.79% (dcw) of P3HP. From 3.0% (v/v) of ethanol, strain MBX4938 produced a total biomass titer of 1.99±0.06 g/L, containing 0.38±0.07% (dcw) of P3HP.

Example 9

P5HV Production from Ethanol as a Carbon Source in Recombinant E. coli Cells

Figure 6:
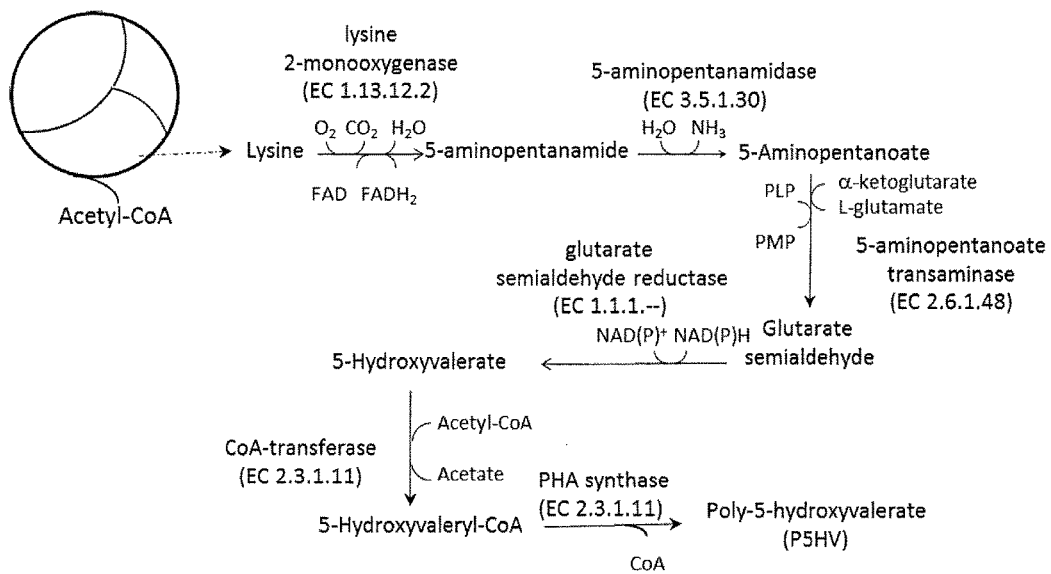
FIG. 6 is a diagram showing the pathways from acetyl-CoA and lysine to poly-5-hydroxyvalerate (P5HV).

This example demonstrates poly-5-hydroxyvalerate (P5HV) production from ethanol as a carbon source in recombinant E. coli cells. The pathway from acetyl-CoA to P5HV is illustrated in FIG. 6. The organisms naturally convert acetyl-CoA to lysine from the TCA cycle intermediate oxaloacetate (OAA) via the lysine biosynthesis pathway. Lysine is then converted to 5-aminopentanamide (via lysine 2-monooxygenase (EC 1.13.12.2)), 5-aminopentanamide to 5-aminopentanoate (via 5-aminopentanamidase (a.k.a, delta-aminovaleramidase (EC 3.5.1.30))), 5-aminopentanoate to glutarate semialdehyde (via 5-aminopentanoate transaminase (a.k.a, delta-aminovalerate transaminase (EC 2.6.1.48))), glutarate semialdehyde to 5-hydroxyvalerate (via glutarate semialdehyde reductase (a.k.a, 5-glutarate semialdehyde reductase (EC 1.1.1.61))), 5-hydroxyvalerate to 5-hydroxyvaleryl-CoA (via CoA transferase (EC 2.8.3.n))), and 5-hydroxyvaleryl-CoA to P5HV (via PHA synthase (EC 2.3.1.n)). Although the organisms naturally make lysine from acetyl-CoA, this conversion can be enhanced, as was done in Farmer et al., US Patent Application No. 2010/0168481 A1.

To produce P5HV from ethanol as a carbon source in recombinant E. coli cells, plasmid pZZ18, expressing the $P_{tet}$-ACIAD2015-ACIAD2018 in pBBR1MCS-4 ($Ap^R$), was transformed into MBX3342 [pJG22, pJB91] (Farmer et al., US Patent Application No. 2010/0168481 A1). The resulting strain was designated MBX4994. The strain and the genes expressed in the strain are shown in Tables 11 and 12, below.

TABLE 11

Microbial strain used to produce P5HV from ethanol as sole carbon source. A star (*) after the gene name denotes that the nucleotide sequence was optimized for expression in E. coli.

| Strain | Relevant host genome modifications | Genes overexpressed from a plasmid | Plasmid origin of replication |
|---|---|---|---|
| MBX4994 | ΔyneI ΔgabD | $P_{trc}$-phaC1-ssaR$_{At}$*-orfZ-Psyn1-dapA$^{C352T}$ | ColE1 ($Gm^R$) |
| | | PompA-davB-davA-davT | p15A ($Cm^R$) |
| | | $P_{tet}$-ACIAD2015-ACIAD2018 | pBBR1 ($Ap^R$) |

TABLE 12

Genes in microbial host strains producing P5HV and 5HV copolymer. A star (*) after the gene name denotes that the nucleotide sequence was optimized for expression in E. coli.

| Gene Name | Enzyme Name | EC Number | Accession No. |
|---|---|---|---|
| dapA$^{C352T}$ | dihydrodipicolinate synthase | 4.2.1.52 | NP_416973 |
| davB | lysine 2-monooxygenase | 1.13.12.2 | BAG54787 |
| davA | 5-aminopentanamidase | 3.5.1.30 | BAG54788 |
| davT | 5-aminopentanoate transaminase | 2.6.1.48 | AAK97868 |
| ssaR$_{At}$* | Succinic semialdehyde reductase | 1.1.1.61 | AAK94781 |
| orfZ | CoA transferase | 2.8.3.n | AAA92344 |
| phaC1 | Polyhydroxyalkanoate synthase | 2.3.1.n | YP_725940 |
| yneI | Succinate-semialdehyde dehydrogenase, NAD$^+$-dependent | 1.2.1.24 | NP_416042 |
| gabD | Succinate-semialdehyde dehydrogenase, NADP$^+$-dependent | 1.2.1.16 | NP_417147 |

To produce P5HV from ethanol, strain MBX4994 was grown in a shake tube assay for 96 h. The seeds culture was prepared the same way as described in Example 6. The production medium consisted of 1×E2 minimal salts solution containing 0.5% (v/v) of ethanol, 1× Trace Salts Solution, 0.1 mM IPTG and appropriate antibiotics (100 µg/mL ampicillin, 25 µg/mL chloramphenicol and 30 µg/mL gentamycin). Both E2 medium and trace elements are described in Example 6. At the end of the growth phase, the biomass and P5HV titers were determined as described previously (Farmer et al., US Patent Application No. 2010/0168481 A1). The P5HV content was measured by gas chromatography-flame ionization detection (GC-FID) (Hewlett-Packard 5890 Series II) and the identity of the 5HV monomer was further confirmed by GC-MS (Agilent GC model 6890N and Agilent MS model 5973.

Strain MBX4994 produced a total biomass titer of 0.72 g/L from 0.5% (v/v) of ethanol, containing 1.45% (dcw) of P5HV.

Example 10

Figure 7:
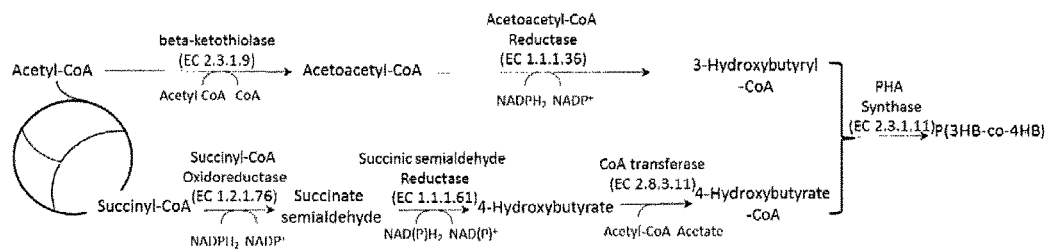
FIG. 7 is a diagram showing the pathways from acetyl-CoA and succinyl-CoA to poly(3-hydroxybutyrate-co-4-hydroxybutyrate) (P(3HB-co-4HB)).

P(3HB-co-4HB) Production from Ethanol as a Carbon Source in Recombinant E. coli Cells This experiment demonstrates the production of poly-(3-hydroxybutyrate-co-4-hydroxybutyrate) (P(3HB-co-4HB)) copolymer in a recombinant E. coli strain from ethanol as a carbon source. These pathways are illustrated in FIG. 7. 3-hydroxybutyryl-CoA is made from acetyl-CoA, and 4-hydroxybutyryl-CoA from succinyl-CoA. The organisms naturally convert between acetyl-CoA and succinyl-CoA via the TCA cycle. To make 3-hydroxybutyryl-CoA from acetyl-CoA, acetyl-CoA is converted to acetoacetyl-CoA (via beta-ketothiolase (phaA)), acetoacetyl-CoA to 3-hydroxybutyryl-CoA (via acetoacetyl-CoA reductase (phaB)), and 3-hydroxybutyryl-CoA to P(3HB-co-4HB) (via PHA synthase (phaC)). To make 4-hydroxybutyryl-CoA from succinyl-CoA, succinyl-CoA is converted to succinate semialdehyde (via succinyl-CoA oxidoreductase), succinate semialdehyde to 4-hydroxybutyrate (via succinate semialdehyde reductase), and 4-hydroxybutyrate to 4-hydroxybutyrate-CoA (via CoA transferase). PHA synthase then combines the two to make P(3HB-co-4HB).

To produce P(3HB-co-4HB) from ethanol as a carbon source in recombinant *E. coli* cells, a derivative of strain LS5218 was used that harbored 3 plasmids, resulting in strain MBX4998 that expressed the recombinant genes outlined in Table 13. The sources of the recombinant genes are listed in Tables 8 and 14.

TABLE 13

Microbial strain used to produce P(3HB-co-4HB) from ethanol as a carbon source. A star (*) after the gene name denotes that the nucleotide sequence was optimized for expression in *E. coli*.

| Strain | Relevant host genome modifications | Genes overexpressed from a plasmid | Plasmid origin of replication (antibiotic resistance) |
|---|---|---|---|
| MBX4998 | ΔyneI ΔgabD $P_{rpsU}$-orfZ $P_{yfdZ}$-bktB-phaB | $P_{syn1}$-sucD*-ssaR$_{At}$* $P_{tet}$-phaC1 $P_{tet}$-ACIAD2015-ACIAD2018 | ColE1 (Ap$^R$) p15A (Cm$^R$) pBBR1 (Tc$^R$) |

TABLE 14

Genes in microbial host strains producing P(3HB-co-4HB) copolymer.

| Gene Name | Enzyme Name | EC Number | Accession No. |
|---|---|---|---|
| bktB | β-ketothiolase | 2.3.1.9 | AAC38322 |
| phaB | acetoacetyl-CoA reductase | 1.1.1.36 | AAD05259 |

To produce P(3HB-co-4HB) copolymer from ethanol, strain MBX4998 was grown in a 43 h shake plate assay. The seeds culture was prepared the same way as described in Example 6. The production medium consisted of 1×E2 minimal salts solution containing either 1.0% or 2.0% (v/v) of ethanol, 1× Trace Salts Solution, 0.1 mM IPTG and appropriate antibiotics (100 μg/mL ampicillin, 25 μg/mL chloramphenicol and 15 μg/mL tetracycline). The initial ethanol concentration was 1.0% (v/v) for both, but 1.0% (v/v) ethanol was added at 28 h for one of the cultures. Both E2 medium and trace elements are described in Example 1. At the end of the growth phase, the biomass and PHA titers, and 3HB and 4HB compositions in PHA, were determined as described previously (Van Walsem et al., International Application No PCT/US11/024612).

Strain MBX4998 produced a total biomass titer of 1.53±0.09 g/L from 1.0% (v/v) ethanol, containing 8.23±1.83% (dcw) copolymer. The copolymer contained 96.90±1.14 (% PHA) of 3HB and 3.10±1.14 (% PHA) of 4HB. From 2.0% (v/v) of ethanol, strain MBX4998 produced a total biomass titer of 2.56±0.13 g/L, containing 21.66±0.88% (dcw) copolymer. The copolymer contained 97.33±0.09 (% PHA) of 3HB and 2.67±0.09 (% PHA) of 4HB.

Example 11

Figure 8:
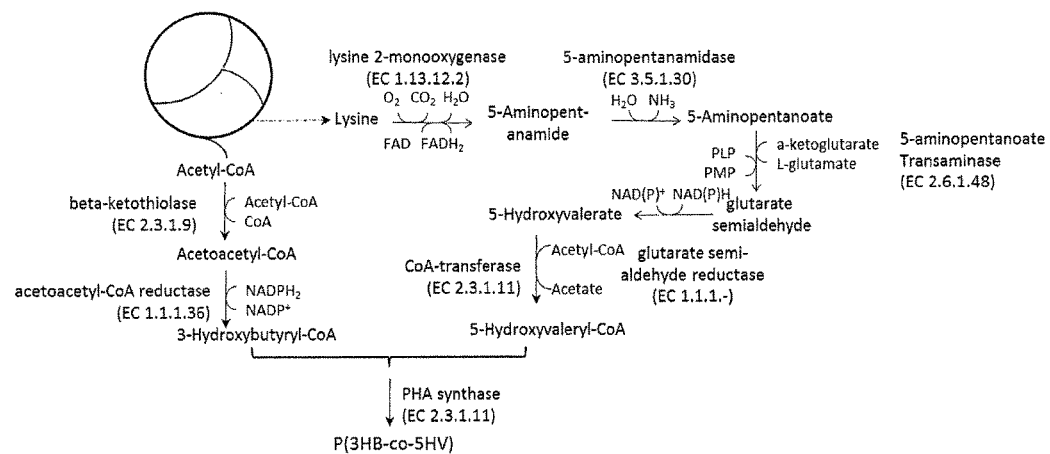
FIG. 8 is a diagram showing the pathways from acetyl-CoA and lysine to poly(3-hydroxybutyrate-co-5-hydroxyvalerate) (P(3HB-co-5HV)).

P(3HB-co-5HV) Production from Ethanol as a Carbon Source in Recombinant *E. coli* Cells This experiment demonstrates the production of poly-(3-hydroxybutyrate-co-5-hydroxyvalerate) (P(3HB-co-5HV)) copolymer in a recombinant *E. coli* strain from ethanol as a carbon source. These pathways are illustrated in FIG. 8. 3-hydroxybutyryl-CoA is made from acetyl-CoA, and 5-hydroxyvaleryl-CoA from lysine. The organisms naturally convert between acetyl-CoA and oxaloacetate (OAA) via the TCA cycle. Lysine is being naturally produced from the TCA cycle intermediate OAA via the lysine biosynthesis pathway. To make 3-hydroxybutyryl-CoA from acetyl-CoA, acetyl-CoA is converted to acetoacetyl-CoA (via beta-ketothiolase (phaA)), acetoacetyl-CoA to 3-hydroxybutyryl-CoA (via acetoacetyl-CoA reductase (phaB)), and 3-hydroxybutyryl-CoA to P(3HB-co-4HB) (via PHA synthase (phaC)). To make 5-hydroxyvaleryl-CoA from lysine, lysine is converted to 5-aminopentanamide (via lysine 2-monooxygenase (EC 1.13.12.2)), 5-aminopentanamide to 5-aminopentanoate (via 5-aminopentanamidase (a.k.a, delta-aminovaleramidase (EC 3.5.1.30))), 5-aminopentanoate to glutarate semialdehyde (via 5-aminopentanoate transaminase (a.k.a, delta-aminovalerate transaminase (EC 2.6.1.48))), glutarate semialdehyde to 5-hydroxyvalerate (via glutarate semialdehyde reductase (a.k.a, glutarate semialdehyde reductase (EC 1.1.1.61))), 5-hydroxyvalerate to 5-hydroxyvaleryl-CoA (via CoA transferase (EC 2.8.3.n))). PHA synthase then combines 3-hydroxybutyryl-CoA and 5-hydroxyvaleryl-CoA to make P(3HB-co-5HV).

To produce P(3HB-co-5HV) from ethanol as a carbon source in recombinant *E. coli* cells, plasmid pZZ18, expressing $P_{tet}$-ACIAD2015-ACIAD2018 in pBBR1MCS-4 (Ap$^R$), was transformed into strain MBX3344 [pJG22, pJB91] (Farmer et al., US Patent Application No. 2010/0168481 A1). The resulting strain was designated MBX4995. The gene modifications in this strain are shown in Table 15, below.

TABLE 15

Microbial strain used to produce P(3HB-co-5HV) from ethanol as sole carbon source. A star (*) after the gene name denotes that the nucleotide sequence was optimized for expression in *E. coli*.

| Strain | Relevant host genome modifications | Genes overexpressed from a plasmid | Plasmid origin of replication |
|---|---|---|---|
| MBX4995 | ΔyneI, ΔgabD, $P_{yfdz}$-bktB-phaB | $P_{trc}$-phaC1-ssaR$_{At}$*-orfZ $P_{syn1}$-dapA$^{C352T}$ $P_{ompA}$-davB-davA-davT $P_{tet}$-ACIAD2015-ACIAD2018 | ColE1 (Gm$^R$) p15A (Cm$^R$) pBBR1 (Ap$^R$) |

To produce P(3HB-co-5HV) copolymer from ethanol, strain MBX4995 was grown in a 76 h shake plate assay. The seed culture was prepared the same way as described in Example 6. The production medium consisted of 1×E2 minimal salts solution containing either 1.0% or 2.0% (v/v) ethanol, 1× Trace Salts Solution, 0.1 mM IPTG and appropriate antibiotics (100 μg/mL ampicillin, 25 μg/mL chloramphenicol and 30 μg/mL gentamycin). Both E2 medium and trace elements are described in Example 1. At the end of the growth phase, the biomass and PHA titers, and 3HB and 5HV compositions in PHA, were determined as described previously (Farmer et al., US Patent Application No. 2010/0168481 A1).

Strain MBX4995 produced a total biomass titer of 1.46±0.13 g/L from 1.0% (v/v) ethanol, containing 6 43±0.45% (dcw) copolymer. The copolymer contained 82.49±0.99 (% PHA) of 3HB and 17.51±0.99 (% PHA) of 5HV. From 2.0% (v/v) of ethanol, strain MBX4995 produced a total biomass titer of 2.54±0.11 g/L, containing 13.30±1.09% (dcw) copolymer. The copolymer contained 66.43±2.39 (% PHA) of 3HB and 33.57±2.39 (% PHA) of 5HV.

Example 12

Growth of Other Microorganisms on Ethanol

This example describes how to enable growth on ethanol in microorganisms that cannot naturally grow on ethanol as a carbon source. An exemplary microbe is *Ralstonia eutropha*, which makes polyhydroxyalkanoates naturally, but does not grow on ethanol as a carbon source. The broad host-range plasmid pZZ17 described in Example 5 that contained the $P_{tet}$-ACIAD2015-ACIAD2018 operon in pSS7 (Km$^R$) was transformed into wild-type *R. eutropha* H-16 obtained from the NCIMB culture collection (Accession No. 10442) using well known molecular biology techniques. The resulting strain MBX4914, along with its parent harboring no plasmid, were initially grown in Nutrient Broth (3 g/L beef extract, 5 g/L peptone) overnight at 30° C. and then were diluted 1:100 into shake tubes containing 3 mL 1×E2 minimal medium supplemented with either 0.1% (v/v) or 1.0% (v/v) ethanol and 50 µg/mL kanamycin. Both E2 medium and trace elements are described in Example 1. The parental *R. eutropha* H-16 strain did not show visible growth after 5 days whereas strain MBX4914 reached final OD$_{600}$ of 1.25 and 6.24 using 0.1% (v/v) and 1.0% (v/v) of ethanol, respectively, after 16 hours of growth at 30° C.

*R. eutropha* is a natural PHA-producer. To examine the PHA production from ethanol as a carbon source, recombinant *R. eutropha* H16 expressing the $P_{tet}$-ACIAD2015-ACIAD2018 operon would be cultured in 1×E2 medium supplemented with ethanol concentrations between 0.5-5.0% (v/v) in an orbital shaker at 30° C. The amount of PHA produced is then measured by gas chromatography-flame ionization detection (GC-FID) (Hewlett-Packard 5890 Series II), as described in Example 6.

Example 13

Adaptive Evolution of a Microbial Strain to Increase Growth Rate on Ethanol as a Carbon Source This example describes how one would improve the growth rate of a microbial strain using ethanol as the carbon source by adaptive laboratory evolution, the method of which is well-known to the artisan (Elena and Lenski, *Nat. Rev. Genet.* 4 (6): 457-469 (2003)); Herring et al., *Nat. Genet.* 38:1406-1412 (2006)). *E. coli* could be used as the target organism to improve the growth rate on ethanol. Such an *E. coli* strain could encompass a polycistronic DNA fragment containing $P_{tet}$-ACIAD2015-ACIAD2018 and an rrnB T2 terminator from pZZ10 as described in Example 4 inserted into the *E. coli* chromosome to provide efficient gene expression and stability. Using well known molecular biology techniques, chromosomal integration is achieved by inserting the polycistronic DNA fragment by targeted knocked-in using the λ red homologous recombination method described by Datsenko and Wanner (*Proc. Nat. Acad. Sci. USA* 97:6640-6645 (2000)) into a locus that is preferably close to the *E. coli* origin of chromosomal replication, such as, but not limited to, the rbsK, ilvC, rrnC and fimD gene loci.

Another method well known to the artisan is to use miniTn5-mediated random integration as described by Huisman et al. (U.S. Pat. Nos. 6,316,262 and 6,593,116). For both approaches, the ethanol utilizing clones are selected on minimal medium agar plates containing ethanol as a carbon source. Suitable E2 minimal medium and trace elements are described in Example 1. *E. coli* clones capable of growing on minimal medium agar plates containing ethanol as a carbon source are initially grown over night in liquid LB medium before being transferred into E2 minimal liquid medium with ethanol concentrations between 0.5-5.0% (v/v) in an orbital shaker at 37° C. The cells are grown to an OD$_{600}$ of about 0.5 before being diluted by passage into fresh E2 ethanol medium. The dilution factor at each passage is adjusted daily to account for changes in growth rate. Cultures are evolved until a stable growth rate of about 0.70 h$^{-1}$ is achieved. Following evolution, individual colonies are isolated on E2 minimal medium agar plates containing ethanol as a carbon source, and growth in aerobic flasks is compared to that of the initial un-evolved clone. The evolved strain with improved ethanol utilizing rate can be used to produce PHA and chemicals from ethanol as a carbon source.

Example 14

PHA Production from Ethanol as a Carbon Source in Recombinant *Acinetobacter* Cells This example describes how to engineer PHA production into microorganisms that naturally grow on ethanol as a carbon source but cannot naturally produce PHA. An exemplary microbe would be *A. baylyi* ADP1. To accomplish this, the PHA biosynthesis genes from other microorganisms that naturally produce PHA would be heterologously expressed in *A. baylyi* ADP1. The source of the PHB genes could be *Ralstonia eutropha* (Peoples and Sinskey, *J. Biol. Chem.* 264:15293-15297 (1989)). The PHB genes phaA, phaB, and phaC under the control of a suitable promoter can be obtained as a 5.2 kb fragment from *R. eutropha* chromosome 1 (Accession No. NC_008313) using appropriate primers. Suitable promoter regions that are highly expressed in *Acinetobacter* have been identified by Camarena et al. (*PLoS Pathog.* 6(4): e1000834. doi:10.1371/journal.ppat.1000834). Exemplary promoter regions include those of genes A1S_2098 and A1S_2102 that were shown to be highly induced by growth on ethanol.

Since efficiency of natural transformation in *Acinetobacter* allows introduction of modified DNA into recipient strains with high frequency, gene replacement with engineered DNA can be achieved efficiently in *A. baylyi* ADP1 through a two-step process in which a cassette containing both selectable and counter-selectable genes is introduced into the target region and then replaced with the modified DNA using well known molecular biology techniques (Metzgar et al., *Nucleic Acids Res.* 32:5780-5790 (2004); de Berardinis et al., *Mol. Syst. Biol.* 4:174; doi:10.1038/msb.2008.10. (2008); Young et al., *Annu. Rev. Microbiol.* 59:519-551 (2005)). Suitable chromosomal integration sites are chosen to be close to the *A. baylyi* ADP1 origin of chromosomal replication for high expression of the integrated genes. To examine PHA production from ethanol as a carbon source, recombinant *A. baylyi* ADP1 strain harboring the phaA, phaB and phaC genes is cultured in 1×E2 medium supplemented with ethanol concentrations between 0.5-5.0% (v/v) in an orbital shaker at 30° C. The amount of PHA produced is then measured by gas chromatography-flame ionization detection (GC-FID) (Hewlett-Packard 5890 Series II), as described in Example 6.

Example 15

Production of 1,4-Butanediol from Ethanol as a Carbon Source in Recombinant *Escherichia coli*

This example describes production of 1,4-butanediol (1,4BD) from ethanol as a carbon source.

An *E. coli* biochemical network model as described in the specification above was supplemented with biochemical reactions suitable for the incorporation of ethanol. Utilization of ethanol by *Escherichia coli* is enabled through the heterologous expression of genes leading to enzymes suitable for the task, as shown in Examples 4-11.

Figure 9:
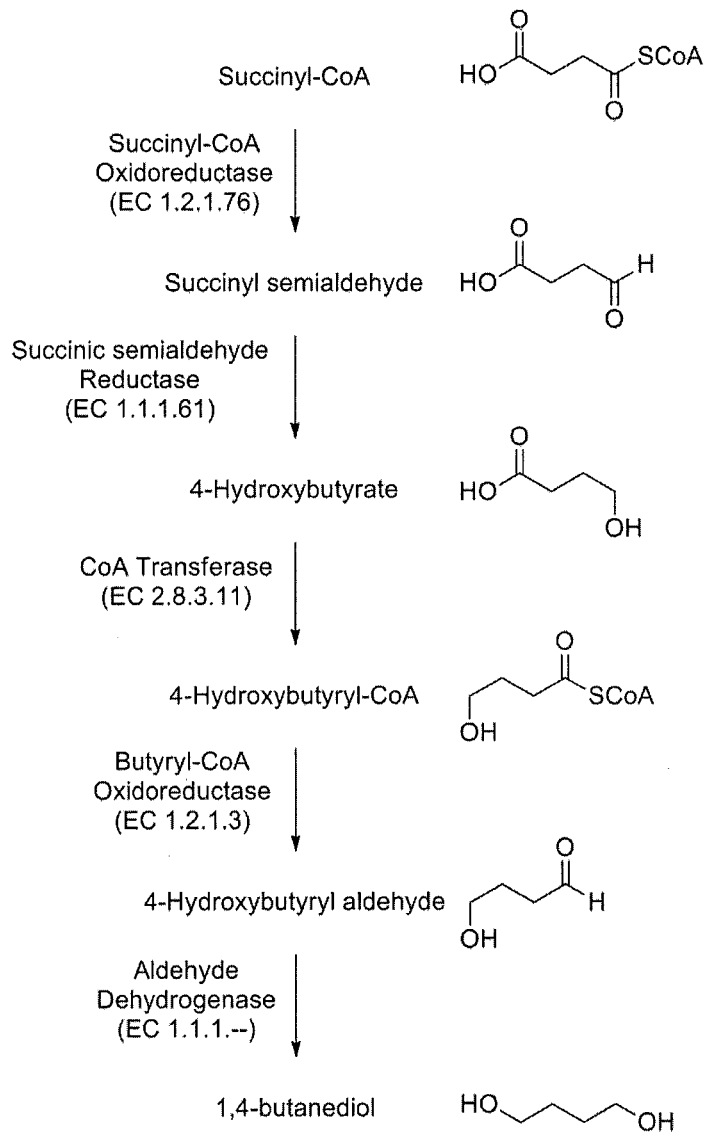
FIG. 9 is a diagram showing the pathway from acetyl-CoA to 1,4-butanediol.

Routes for the production of 1,4BD were added to the in silico *E. coli* model to discover the feasibility for 1,4BD production from ethanol as a carbon source. Table 16 details exemplary EC numbers and enzymes names for a feasible route from succinyl-CoA, a well-known metabolic intermediate (the organisms naturally convert between acetyl-CoA and succinyl-CoA). FIG. 9 illustrates this pathway. The theoretical yield of BDO from ethanol using this biochemical reaction set was calculated to be 0.67 (wt/wt). To enable production of 1,4BD, genes listed in Table 16 are heterologously expressed in *E. coli*. Techniques related to heterologous expression of multiple genes under a variety of promoters in a single *E. coli* cell is well understood (as is demonstrated herein in Examples 6-11) for the synthesis of various products from ethanol as a carbon source.

TABLE 16

Exemplary EC numbers and enzyme names participating in the synthesis of 1,4-butanediol from ethanol.

| EC Number | Enzyme Name |
|---|---|
| 1.2.1.76 | Succinyl-CoA oxidoreductase |
| 1.1.1.61 | Succinate semialdehyde reductase |
| 2.8.3.n | 4-hydroxybutyrate CoA transferase |
| 1.2.1.3 | Propionaldehyde dehydrogenase |
| 1.2.1.4 | Aldehyde dehydrogenase |
| 1.1.1.- | 1,4-butanediol dehydrogenase |

Example 16

Production of Poly(3-Hydroxybutyrate) from Ethanol as a Carbon Source in Recombinant *Escherichia coli*

This example describes production of poly(3-hydroxybutyrate) (P3HB) from ethanol as a carbon source. The routes for production of P3HB that were determined in this example were confirmed experimentally in the data and results presented in Example 6.

An *E. coli* biochemical network model as described in the specification above was supplemented with biochemical reactions suitable for the incorporation of ethanol. Utilization of ethanol by *Escherichia coli* is enabled through the heterologous expression of genes leading to enzymes suitable for the task, as shown in Examples 4-11.

Routes for the production of P3HB were added to the in silico *E. coli* model to discover the feasibility for P3HB production from ethanol as a carbon source. Table 17 details exemplary EC numbers and enzymes names for a feasible route from acetyl-CoA, a well-known metabolic intermediate. The theoretical yield of P3HB from ethanol using this biochemical reaction set was calculated to be 0.91 (wt/wt). To enable production of P3HB, genes listed in Table 17 are heterologously expressed in *E. coli*. Techniques related to heterologous expression of multiple genes under a variety of promoters in a single *E. coli* cell is well understood (as is demonstrated herein in Example 6) for the synthesis of P3HB from ethanol as a carbon source.

TABLE 17

Exemplary EC numbers and enzyme names participating in the synthesis of poly(3-hydroxybutyrate) from ethanol.

| EC Number | Enzyme Name |
|---|---|
| 2.3.1.9 | beta-Ketothiolase |
| 1.1.1.36 | Acetoacetyl-CoA reductase |
| 2.3.1.- | Polyhydroxyalkanoate synthase |

Example 17

Production of Isopropanol from Ethanol as a Carbon Source in Recombinant *Escherichia coli*

This example describes production of isopropanol (IPA) from ethanol as a carbon source.

An *E. coli* biochemical network model as described in the specification above was supplemented with biochemical reactions suitable for the incorporation of ethanol. Utilization of ethanol by *Escherichia coli* is enabled through the heterologous expression of genes leading to enzymes suitable for the task, as shown in Examples 4-11.

Figure 10:
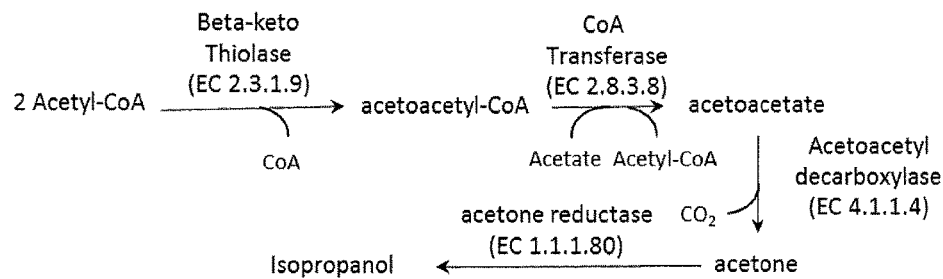
FIG. 10 is a diagram showing the pathway from acetyl-CoA to isopropanol.

Routes for the production of IPA were added to the in silico *E. coli* model to discover the feasibility for IPA production from ethanol as a carbon source. Table 18 details exemplary EC numbers and enzymes names for a feasible route from acetyl-CoA, a well-known metabolic intermediate. FIG. 10 illustrates this pathway. The theoretical yield of IPA from ethanol using this biochemical reaction set was calculated to be 0.65 (wt/wt). To enable production of IPA, genes listed in Table 18 are heterologously expressed in *E. coli*. Techniques related to heterologous expression of multiple genes under a variety of promoters in a single *E. coli* cell is well understood (as is demonstrated herein in Examples 6-11) for the synthesis of various products from ethanol as a carbon source.

TABLE 18

Exemplary EC numbers and enzyme names participating in the synthesis of isopropanol from ethanol.

| EC Number | Enzyme Name |
|---|---|
| 2.3.1.9 | beta-Ketothiolase |
| 2.8.3.8 | Coenzyme A transferase |
| 4.1.1.4 | Acetoacetyl decarboxylase |
| 1.1.1.80 | Acetone reductase |

Example 18

Production of 1-Propanol from Ethanol as a Carbon Source in Recombinant *Escherichia coli*

This example describes production of 1-propanol from ethanol as a carbon source.

An *E. coli* biochemical network model as described in the specification above was supplemented with biochemical reactions suitable for the incorporation of ethanol. Utilization of ethanol by *Escherichia coli* is enabled through the heterologous expression of genes leading to enzymes suitable for the task, as shown in Examples 4-11.

Figure 11:
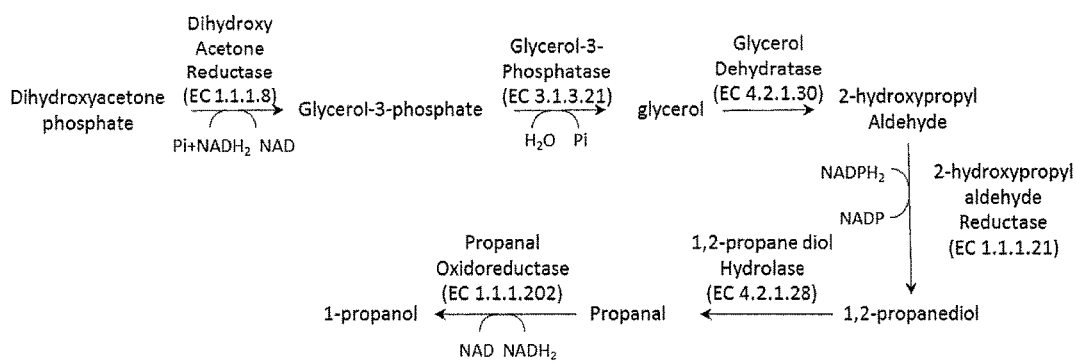
FIG. 11 is a diagram showing the pathway from dihydroxyacetone phosphate to 1-propanol.

Routes for the production of 1-propanol were added to the in silico *E. coli* model to discover the feasibility for 1-propanol production from ethanol as a carbon source. Table 19 details exemplary EC numbers and enzymes names for a feasible route from dihydroxyacetone phosphate, a well-known metabolic intermediate which is made naturally from acetyl-CoA by the organisms via gluconeogenesis. FIG. 11 illustrates the pathway. The theoretical yield of 1-propanol from ethanol using this biochemical reaction set was calculated to be 0.56 (wt/wt). To enable production of 1-propanol, genes listed in Table 19 are heterologously expressed in *E. coli*. Techniques related to heterologous expression of multiple genes under a variety of promoters in a single *E. coli* cell is well understood (as is demonstrated herein in Examples 6-11) for the synthesis of various products from ethanol as a carbon source.

TABLE 19

Exemplary EC numbers and enzyme names participating in the synthesis of 1-propanol from ethanol.

| EC Number | Enzyme Name |
|---|---|
| 1.1.1.8 | Dihydroxyacetone reductase |
| 3.1.3.21 | Glycerol-3-phosphatase |
| 4.2.1.30 | Glycerol dehydratase |
| 1.1.1.21 | 2-Hydroxypropylaldehyde reductase |
| 4.2.1.28 | 1,2-Propanediol hydrolase |
| 1.1.1.202 | Propanal oxidoreductase |

Example 19

Production of Adipic Acid from Ethanol as a Carbon Source in Recombinant *Escherichia coli*

This example describes production of adipic acid from ethanol as a carbon source.

An *E. coli* biochemical network model as described in the specification above was supplemented with biochemical reactions suitable for the incorporation of ethanol. Utilization of ethanol by *Escherichia coli* is enabled through the heterologous expression of genes leading to enzymes suitable for the task, as shown in Examples 4-11.

Figure 12:
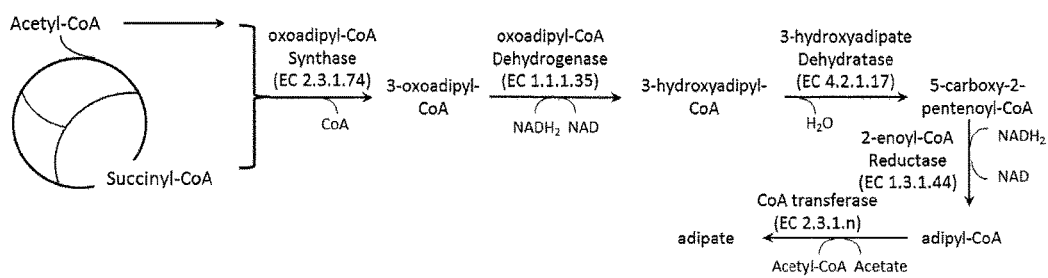
FIG. 12 is a diagram showing the pathway from succinyl-CoA and acetyl-CoA to adipate.

Routes for the production of adipic acid were added to the in silico *E. coli* model to discover the feasibility for adipic acid production from ethanol as a carbon source. Table 20 details exemplary EC numbers and enzymes names for a feasible route from acetyl-CoA and succinyl-CoA (the organisms naturally convert between acetyl-CoA and succinyl-CoA). FIG. 12 illustrates this pathway. The theoretical yield of adipic acid from ethanol using this biochemical reaction set was calculated to be 1.06 (wt/wt). To enable production of adipic acid, genes listed in Table 20 are heterologously expressed in *E. coli*. Techniques related to heterologous expression of multiple genes under a variety of promoters in a single *E. coli* cell is well understood (as is demonstrated herein in Examples 6-11) for the synthesis of various products from ethanol as a carbon source.

TABLE 20

Exemplary EC numbers and enzyme names participating in the synthesis of adipic acid from ethanol.

| EC Number | Enzyme Name |
|---|---|
| 2.3.1.174 | Oxoadipyl-Coenzyme A synthase |
| 1.1.1.35 | Oxoadipyl-Coenzyme A dehydrogenase |
| 4.2.1.17 | 3-Hydroxyadipate dehydratase |
| 1.3.1.44 | 2-Enoyl-CoA reductase |
| 2.8.3.- | Coenzyme A transferase |

Example 20

Production of 3-Hydroxypropionic Acid from Ethanol as a Carbon Source in Recombinant *Escherichia coli*

This example describes production of 3-hydroxypropionic acid (3HP) from ethanol as a carbon source.

An *E. coli* biochemical network model as described in the specification above was supplemented with biochemical reactions suitable for the incorporation of ethanol. Utilization of ethanol by *Escherichia coli* is enabled through the heterologous expression of genes leading to enzymes suitable for the task, as shown in Examples 4-11.

Routes for the production of 3HP were added to the in silico *E. coli* model to discover the feasibility for 3HP production from ethanol as a carbon source. Table 21 details exemplary EC numbers and enzymes names for a feasible route from acetyl-CoA, a well-known metabolic intermediate. The theoretical yield of 3HP from ethanol using this biochemical reaction set was calculated to be 1.09 (wt/wt). To enable production of 3HP, genes listed in Table 21 are heterologously expressed in *E. coli*. Techniques related to heterologous expression of multiple genes under a variety of promoters in a single *E. coli* cell is well understood (as is demonstrated herein in Examples 6-11) for the synthesis of various products from ethanol as a carbon source.

TABLE 21

Exemplary EC numbers and enzyme names participating in the synthesis of 3-hydroxypropionic acid from ethanol.

| EC Numbers | Enzyme Name |
|---|---|
| 6.4.1.2 | Acetyl-CoA carboxylase |
| 1.2.1.75 | Malonyl-CoA reductase |
| 1.1.1.59 | Malonyl semialdehyde reductase |

Example 21

Replacing the Ethanol Feedstock with Xylose

This example demonstrates polyhydroxyalkanoate (PHA) homopolymer and copolymer production from xylose as a carbon source in recombinant *E. coli* cells. The PHA homopolymer and copolymer produced in this example include poly-3-hydroxybutyrate (P3HB), poly-3-hydroxypropionate (P3HP), poly-4-hydroxybutryrate (P4HB), poly-5-hydroxyvalerate (P5HV), poly-3-hydroxybutyrate-co-4-hydroxybutyrate (P(3HB-co-4HB)), and poly-3-hydroxybutyrate-co-5-hydroxyvalerate (P(3HB-co-5HV)).

To demonstrate production of PHAs from xylose, the precursor strains engineered to produce the various homopolymers and copolymers from ethanol as a carbon source in the previous examples were used. All precursor strains possess the same genotype as the ethanol utilizing strains with the exception that they lack the broad host-range plasmid expressing the $P_{tet}$-ACIAD2015-ACIAD2018 operon which enables ethanol utilization. These strains include MBX1335, the precursor strain of MBX4900 as described in Example 6 for P3HB production, MBX5116, the precursor strain of MBX4978 as described in Example 7 for P4HB production, MBX5115, the precursor strain of MBX4938 as described in Example 8 for P3HP production, MBX4081, the precursor strain of MBX4994 as described in Example 9 for P5HV production, MBX4996, the precursor strain of MBX4998 as described in Example 10 for P(3HB-co-4HB) production, and MBX4083, the precursor strain of MBX4995 as described in Example 11 for P(3HB-co-5HV) production.

All strains were cultured overnight in sterile tubes containing 3 mL of LB supplemented with the appropriate antibiotics to ensure plasmid maintenance. From this, 25 µL was used to inoculate Duetz deep-well shake plate wells in triplicates containing 475 µL of 1×E2 medium supplemented with 10 g/L or 20 g/L xylose, appropriate antibiotics and IPTG where necessary. The final concentration of antibiotics used were 100 µg/mL ampicillin, 25 µg/mL chloramphenicol, 100 µg/mL ampicillin and 30 µg/mL gentamycin. The final IPTG concentration used was 0.1 mM. Both E2 medium and trace elements are described in Example °1. The cells were grown for 6 h at 37° C. followed by 48 or 66 h at 30° C. with shaking at 250 rpm. At the end of the growth phase, the biomass titer, PHA titer and composition were determined as described in Examples 6 to 11. The strain, growth condition and polymer production for each PHA homopolymer and copolymer are listed in Table 22.

TABLE 22

PHA polymer and copolymer production from xylose.

| PHA | Strain | Growth condition | Biomass (g/L) | PHA (% dcw) | 3HB (% PHA) |
|---|---|---|---|---|---|
| P3HB | MBX1335 | 10 g/L xylose, 72 h | 2.99 ± 0.06 | 8.36 ± 0.16 | — |
| P3HP | MBX5115 | 20 g/L xylose, 0.1 mM IPTG, 54 h | 2.40 ± 0.12 | 0.53 ± 0.16 | — |
| P4HB | MBX5116 | 20 g/L xylose, 54 h | 2.50 ± 0.17 | 1.70 ± 0.41 | — |
| P5HV | MBX4081 | 10 g/L xylose, 0.1 mM IPTG, 72 h | 2.83 ± 0.06 | 4.15 ± 0.13 | — |
| P(3HB-co-4HB) | MBX4996 | 10 g/L xylose, 72 h | 2.66 ± 0.23 | 7.11 ± 0.70 | 94.73 ± 0.17 |
| P(3H-co-5HV) | MBX4083 | 20 g/L xylose, 0.1 mM IPTG, 72 h | 5.54 ± 0.11 | 48.89 ± 0.68 | 87.08 ± 0.16 |

These results demonstrate that PHAs can be produced from xylose as a sole carbon source in recombinant *E. coli* cells. For the copolymers, the corresponding co-monomer 4HB or 5HV makes up the remaining fraction of the composition.

Other than in the examples herein, or unless otherwise expressly specified, all of the numerical ranges, amounts, values and percentages, such as those for amounts of materials, elemental contents, times and temperatures of reaction, ratios of amounts, and others, in the following portion of the specification and attached claims may be read as if prefaced by the word "about" even though the term "about" may not expressly appear with the value, amount, or range. Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains error necessarily resulting from the standard deviation found in its underlying respective testing measurements. Furthermore, when numerical ranges are set forth herein, these ranges are inclusive of the recited range end points (i.e., end points may be used). When percentages by weight are used herein, the numerical values reported are relative to the total weight.

Also, it should be understood that any numerical range recited herein is intended to include all sub-ranges subsumed therein. For example, a range of "1 to 10" is intended to include all sub-ranges between (and including) the recited minimum value of 1 and the recited maximum value of 10, that is, having a minimum value equal to or greater than 1 and a maximum value of equal to or less than 10. The terms "one," "a," or "an" as used herein are intended to include "at least one" or "one or more," unless otherwise indicated.

Any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

While this invention has been particularly shown and described with references to preferred embodiments thereof, it will be understood by those skilled in the art that various changes in form and details may be made therein without departing from the scope of the invention encompassed by the appended claims.

APPENDIX

Annotated DNA sequence of the cloned ACIAD2015 and ACIAD2018 genes in pZZ10

```
              p15A origin of replication
6601 TCTAGATTTCAGTGCAATTTATCTCTTCAAATGTAGCACCTGAAGTCAGCCCCATACGAT
     AGATCTAAAGTCACGTTAAATAGAGAAGTTTACATCGTGGACTTCAGTCGGGGTATGCTA Predicted -35 box of P_tet
6661 ATAAGTTGTAATTCTCATGTTTGACAGCTTATCATCGATAAGCTTTAATGCGGTAGTTTA
     TATTCAACATTAAGAGTACAAACTGTCGAATAGTAGCTATTCGAAATTACGCCATCAAAT Predicted -10 box of P_tet
6721 TCACAGTTAAATTGCTAACGCAGTCAGGCACCGTGTATGAAATCTAACAATGCGCTCATC
     AGTGTCAATTTAACGATTGCGTCAGTCCGTGGCACATACTTTAGATTGTTACGCGAGTAG 6781 GTCATCCTCGGCACCGTCACCCTGGATGCTGTAGGCATAGGCTTGGTTATGCCGGTACTG
     CAGTAGGAGCCGTGGCAGTGGGACCTACGACATCCGTATCCGAACCAATACGGCCATGAC 6841 CCGGGCCTCTTGCGGGATGTCGTGGAATGCCTTCGAATTCAGCACCTGCACATGGGACGT
     GGCCCGGAGAACGCCCTACAGCACCTTACGGAAGCTTAAGTCGTGGACGTGTACCCTGCA
         SEQ ID No: 14
         SEQ ID NO: 15

RBS       ACIAD2015--→
                M  A  F  K  N  I  A  D  Q  T  N  G  F  Y  I  P
    C .
  1 CAGAGGTTTTTATGGCTTTTAAAAATATTGCTGACCAAACAAACGGTTTTTATATCCCTT
    GTCTCCAAAAATACCGAAAATTTTTATAACGACTGGTTTGTTTGCCAAAAATATAGGGAA

.  V  S  L  F  G  P  G  C  A  K  E  I  G  T  K  A  Q  N  L
    G .
 61 GTGTCTCCCTTTTTGGCCCTGGTTGTGCCAAAGAAATTGGTACCAAAGCACAAAATTTAG
    CACAGAGGGAAAAACCGGGACCAACACGGTTTCTTTAACCATGGTTTCGTGTTTTAAATC

.  A  K  K  A  L  I  V  T  D  A  G  L  F  K  F  G  V  A  D
    T .
121 GTGCAAAAAAGCACTCATCGTGACTGATGCTGGTTTATTTAAATTTGGTGTAGCTGACA
    CACGTTTTTTCGTGAGTAGCACTGACTACGACCAAATAAATTTAAACCACATCGACTGT

.  I  A  A  Y  L  K  E  A  G  V  D  S  H  I  F  P  G  A  E
    P .
181 CTATCGCAGCATACCTTAAAGAAGCTGGCGTAGACAGTCATATTTTCCCAGGCGCTGAAC
    GATAGCGTCGTATGGAATTTCTTCGACCGCATCTGTCAGTATAAAAGGGTCCGCGACTTG

.  N  P  T  D  K  N  V  H  N  G  V  D  A  Y  N  T  N  G  C
    D .
241 CCAATCCGACAGATAAAAACGTACATAATGGCGTTGATGCATATAATACCAATGGATGTG
    GGTTAGGCTGTCTATTTTTGCATGTATTACCGCAACTACGTATATTATGGTTACCTACAC

.  F  I  V  S  L  G  G  G  S  S  H  D  C  A  K  G  I  G  L
    V .
301 ACTTTATTGTATCGCTCGGTGGTGGATCATCTCACGACTGTGCAAAAGGTATTGGATTAG
    TGAAATAACATAGCGAGCCACCACCTAGTAGAGTGCTGACACGTTTTCCATAACCTAATC

.  T  A  G  G  G  H  I  R  D  Y  E  G  I  D  K  S  T  V  P
    M .
361 TTACCGCAGGCGGTGGTCACATTCGTGATTACGAAGGAATTGATAAAAGTACTGTTCCAA
    AATGGCGTCCGCCACCAGTGTAAGCACTAATGCTTCCTTAACTATTTTCATGACAAGGTT

.  T  P  L  I  A  V  N  T  T  A  G  T  A  S  E  M  T  R  F
    C .
421 TGACGCCGTTAATTGCAGTCAATACCACTGCAGGCACAGCATCTGAAATGACACGTTTCT
    ACTGCGGCAATTAACGTCAGTTATGGTGACGTCCGTGTCGTAGACTTTACTGTGCAAAGA

.  I  I  T  N  T  D  T  H  V  K  M  A  I  V  D  W  R  C  T
    P .
481 GTATTATTACCAATACAGATACACATGTAAAAATGGCGATTGTAGATTGGCGTTGTACCC
    CATAATAATGGTTATGTCTATGTGTACATTTTTACCGCTAACATCTAACCGCAACATGGG

.  L  I  A  I  D  D  P  K  L  M  I  A  K  P  A  S  L  T  A
    A .
541 CACTGATTGCCATTGATGACCCTAAGCTCATGATTGCTAAGCCTGCAAGCCTGACTGCTG
    GTGACTAACGGTAACTACTGGGATTCGAGTACTAACGATTCGGACGTTCGGACTGACGAC

.  T  G  M  D  A  L  T  H  A  V  E  A  Y  V  S  T  A  A  N
    P .
601 CGACTGGTATGGATGCGCTGACACATGCTGTCGAAGCTTATGTATCTACTGCTGCGAACC
    GCTGACCATACCTACGCGACTGTGTACGACAGCTTCGAATACATAGATGACGACGCTTGG

.  I  T  D  A  C  A  E  K  A  I  S  M  I  S  E  W  L  S  P
```

APPENDIX-continued

Annotated DNA sequence of the cloned ACIAD2015 and ACIAD2018 genes in pZZ10

```
          A .
661 CAATCACAGACGCCTGTGCCGAAAAAGCAATCAGCATGATCAGTGAATGGCTCAGCCCAG
    GTTAGTGTCTGCGGACACGGCTTTTTCGTTAGTCGTACTAGTCACTTACCGAGTCGGGTC

. V  A  N  G  E  N  L  E  A  R  D  A  M  S  Y  A  Q  Y  L
     A .
721 CTGTTGCCAATGGTGAAAACCTTGAAGCACGTGATGCAATGAGCTATGCCCAATATCTTG
    GACAACGGTTACCACTTTTGGAACTTCGTGCACTACGTTACTCGATACGGGTTATAGAAC

. G  M  A  F  N  N  A  S  L  G  Y  V  H  A  M  A  H  Q  L
     G .
781 CAGGTATGGCATTTAACAATGCGTCATTAGGTTATGTTCATGCCATGGCGCACCAACTTG
    GTCCATACCGTAAATTGTTACGCAGTAATCCAATACAAGTACGGTACCGCGTGGTTGAAC

. G  F  Y  N  L  P  H  G  V  C  N  A  V  L  L  P  H  V  C
     E .
841 GCGGTTTCTACAATCTGCCACACGGCGTATGTAATGCGGTATTGTTGCCACACGTTTGTG
    CGCCAAAGATGTTAGACGGTGTGCCGCATACATTACGCCATAACAACGGTGTGCAAACAC

. F  N  L  I  A  C  P  E  R  Y  A  R  I  A  E  L  M  G  V
     N .
901 AGTTCAACCTGATTGCTTGCCCAGAGCGTTATGCACGTATCGCAGAATTAATGGGCGTAA
    TCAAGTTGGACTAACGAACGGGTCTCGCAATACGTGCATAGCGTCTTAATTACCCGCATT

. T  H  G  L  T  V  T  E  A  A  Y  A  A  I  D  A  I  R  T
     L .
961 ATACACACGGCCTTACGGTGACTGAAGCTGCATATGCTGCAATCGATGCAATTCGTACAT
    TATGTGTGCCGGAATGCCACTGACTTCGACGTATACGACGTTAGCTACGTTAAGCATGTA

. S  K  S  I  G  I  P  S  G  L  T  E  L  G  V  K  T  E  D
     L .
1021 TATCAAAATCAATTGGTATCCCATCTGGCTTGACCGAGCTTGGTGTAAAAACTGAAGATC
     ATAGTTTTAGTTAACCATAGGGTAGACCGAACTGGCTCGAACCACATTTTTGACTTCTAG

. A  V  M  A  E  N  A  Q  K  D  A  C  M  L  T  N  P  R  K
     A .
1081 TTGCAGTAATGGCCGAAAATGCACAAAAAGACGCGTGTATGTTGACTAATCCACGCAAAG
     AACGTCATTACCGGCTTTTACGTGTTTTTCTGCGCACATACAACTGATTAGGTGCGTTTC

End of ACIAD2015 RBS
        . N  H  A  Q  V  V  D  I  F  T  A  A  L  * SEQ ID NO: 16
1141 CAAATCACGCTCAAGTTGTAGATATTTTCACAGCAGCATTGTAAACCTAGA<u>AGGAGG</u>TTT
     GTTTAGTGCGAGTTCAACATCTATAAAAGTGTCGTCGTAACATTTGGATCTTCCTCCAAA
     SEQ ID NO: 17
     SEQ ID NO: 18

ACIAD2018--->
          M  R  Y  I  D  P  N  Q  P  G  S  K  V  Q  F  K  A  Q  Y
     E .
1201 TTATGCGTTATATCGATCCTAATCAACCTGGCTCTAAGGTTCAATTTAAAGCACAATATG
     AATACGCAATATAGCTAGGATTAGTTGGACCGAGATTCCAAGTTAAATTTCGTGTTATAC

. N  F  I  G  G  Q  W  V  P  P  V  K  G  E  Y  F  G  N  S
     S .
1261 AAAACTTTATTGGCGGTCAGTGGGTTCCTCCTGTAAAAGGAGAATACTTCGGAAATAGCT
     TTTTGAAATAACCGCCAGTCACCCAAGGAGGACATTTTCCTCTTATGAAGCCTTTATCGA

. P  V  D  G  K  V  F  T  Q  I  P  R  S  S  V  E  D  I  E
     L .
1321 CTCCTGTCGATGGCAAAGTATTTACTCAAATTCCTCGCTCAAGCGTCGAAGATATTGAAC
     GAGGACAGCTACCGTTTCATAAATGAGTTTAAGGAGCGAGTTCGCAGCTTCTATAACTTG

. A  L  D  A  A  H  K  A  K  A  D  W  N  K  A  S  P  T  V
     R .
1381 TAGCACTTGATGCAGCGCACAAAGCGAAAGCTGATTGGAATAAAGCATCACCTACAGTTC
     ATCGTGAACTACGTCGCGTGTTTCGCTTTCGACTAACCTTATTTCGTAGTGGATGTCAAG

. S  N  V  L  L  K  I  A  D  R  L  E  E  N  L  E  L  L  A
     V .
1441 GTTCAAATGTTTTACTTAAAATTGCAGATCGTCTGGAAGAAAACCTAGAGCTACTTGCTG
     CAAGTTTACAAAATGAATTTTAACGTCTAGCAGACCTTCTTTTGGATCTCGATGAACGAC

. A  E  T  W  E  N  G  K  P  I  R  E  T  L  A  A  D  I  P
     L .
1501 TAGCAGAAACATGGGAAAATGGTAAACCTATCCGCGAAACACTCGCAGCAGATATCCCAC
     ATCGTCTTTGTACCCTTTTACCATTTGGATAGGCGCTTTGTGAGCGTCGTCTATAGGGTG
```

APPENDIX-continued

Annotated DNA sequence of the cloned ACIAD2015 and ACIAD2018 genes in pZZ10

```
       .  A  I  D  H  F  R  Y  F  A  G  C  I  R  A  Q  E  G  G  I
     S  .
1561 TTGCAATTGACCATTTCCGCTATTTCGCAGGCTGTATACGTGCACAAGAAGGTGGTATTT
     AACGTTAACTGGTAAAGGCGATAAAGCGTCCGACATATGCACGTGTTCTTCCACCATAAA

.  E  I  D  E  D  T  I  A  Y  H  F  H  E  P  L  G  V  V  G
     Q  .
1621 CAGAAATTGATGAGGATACCATTGCTTATCATTTCCATGAACCGCTTGGTGTTGTAGGCC
     GTCTTTAACTACTCCTATGGTAACGAATAGTAAAGGTACTTGGCGAACCACAACATCCGG

.  I  I  P  W  N  F  P  I  L  M  A  A  W  K  L  A  P  A  L
     A  .
1681 AGATCATTCCATGGAACTTTCCAATTTTGATGGCTGCATGGAAATTGGCACCAGCACTGG
     TCTAGTAAGGTACCTTGAAAGGTTAAAACTACCGACGTACCTTTAACCGTGGTCGTGACC

.  A  G  N  C  I  V  L  K  P  A  E  Q  T  P  S  S  I  L  V
     L  .
1741 CAGCAGGTAACTGTATTGTTCTTAAACCAGCAGAGCAAACACCGTCAAGTATTCTAGTTC
     GTCGTCCATTGACATAACAAGAATTTGGTCGTCTCGTTTGTGGCAGTTCATAAGATCAAG

.  A  E  L  I  Q  D  L  L  P  P  G  V  L  N  I  V  N  G  Y
     G  .
1801 TGGCTGAATTGATTCAGGACCTCCTTCCACCTGGCGTACTTAATATCGTCAATGGATACG
     ACCGACTTAACTAAGTCCTGGAGGAAGGTGGACCGCATGAATTATAGCAGTTACCTATGC

.  A  E  V  G  R  P  L  A  T  N  P  R  I  S  K  I  A  F  T
     G  .
1861 GTGCTGAGGTTGGTCGTCCTTTAGCGACAAATCCAAGAATTTCAAAAATTGCATTCACTG
     CACGACTCCAACCAGCAGGAAATCGCTGTTTAGGTTCTTAAAGTTTTTAACGTAAGTGAC

.  S  T  K  V  G  Q  M  I  M  Q  Y  A  T  E  N  I  I  P  V
     T  .
1921 GTTCAACCAAAGTTGGACAAATGATCATGCAATATGCCACTGAAAATATCATTCCTGTAA
     CAAGTTGGTTTCAACCTGTTTACTAGTACGTTATACGGTGACTTTTATAGTAAGGACATT

.  L  E  L  G  G  K  S  P  N  I  F  F  E  D  I  L  D  K  E
     D  .
1981 CGCTAGAACTTGGTGGTAAATCTCCAAATATCTTTTTTGAAGACATCTTAGATAAAGAAG
     GCGATCTTGAACCACCATTTAGAGGTTTATAGAAAAACTTCTGTAGAATCTATTTCTTC

.  D  Y  L  E  K  T  L  E  G  F  A  M  F  A  L  N  Q  G  E
     V  .
2041 ATGATTATTTGGAAAAAACACTTGAAGGTTTTGCCATGTTTGCCTTGAACCAGGGTGAAG
     TACTAATAAACCTTTTTTGTGAACTTCCAAAACGGTACAAACGGAACTTGGTCCCACTTC

.  C  T  C  P  S  R  A  L  V  Q  E  S  I  A  D  K  F  L  E
     M  .
2101 TATGTACCTGCCCTTCACGTGCACTTGTTCAGGAAAGTATTGCTGACAAATTCCTTGAAA
     ATACATGGACGGGAAGTGCACGTGAACAAGTCCTTTCATAACGACTGTTTAAGGAACTTT

.  A  V  E  R  V  K  R  I  K  T  G  H  P  L  D  T  E  T  M
     I  .
2161 TGGCTGTAGAGCGTGTCAAACGCATCAAGACGGGTCATCCACTTGATACAGAAACCATGA
     ACCGACATCTCGCACAGTTTGCGTAGTTCTGCCCAGTAGGTGAACTATGTCTTTGGTACT

.  G  A  Q  A  S  K  Q  Q  F  D  K  I  L  G  C  I  D  T  G
     R  .
2221 TTGGCGCACAAGCCTCTAAGCAACAGTTTGATAAAATTTTAGGCTGTATTGATACAGGTC
     AACCGCGTGTTCGGAGATTCGTTGTCAAACTATTTTAAAATCCGACATAACTATGTCCAG

.  N  E  G  A  Q  L  L  T  G  G  D  A  R  H  D  V  D  G  G
     F  .
2281 GTAATGAAGGTGCACAACTTTTAACTGGTGGTGATGCACGTCACGATGTAGATGGTGGTT
     CATTACTTCCACGTGTTGAAAATTGACCACCACTACGTGCAGTGCTACATCTACCACCAA

.  Y  I  E  P  T  I  F  K  G  N  N  S  M  K  I  F  Q  E  E
     I  .
2341 TTTATATTGAACCAACGATTTTCAAAGGCAATAACAGTATGAAAATCTTCCAAGAAGAAA
     AAATATAACTTGGTTGCTAAAAGTTTCCGTTATTGTCATACTTTTAGAAGGTTCTTCTTT

.  F  G  P  V  L  S  V  T  T  F  K  D  F  D  D  A  M  R  I
     A  .
2401 TTTTTGGACCAGTACTTTCAGTAACGACATTTAAAGATTTTGACGATGCAATGCGTATTG
     AAAAACCTGGTCATGAAAGTCATTGCTGTAAATTTCTAAAACTGCTACGTTACGCATAAC

.  N  D  T  I  Y  G  L  G  A  G  V  W  S  R  S  A  H  T  S
     Y  .
```

APPENDIX-continued

Annotated DNA sequence of the cloned ACIAD2015 and ACIAD2018 genes in pZZ10

```
                .  R  A  G  R  A  I  E  A  G  R  V  W  T  N  C  Y  H  L  Y
      P  .
2461 CCAACGACACGATTTATGGCTTGGGTGCTGGTGTATGGTCACGTTCTGCACATACCTCAT
     GGTTGCTGTGCTAAATACCGAACCCACGACCACATACCAGTGCAAGACGTGTATGGAGTA

.  A  H  A  A  F  G  G  Y  K  Q  S  G  I  G  R  E  N  H  R
      M  .
2521 ACCGTGCTGGTCGTGCGATTGAAGCCGGTCGTGTGTGGACAAACTGTTATCACCTTTATC
     TGGCACGACCAGCACGCTAACTTCGGCCAGCACACACCTGTTTGACAATAGTGGAAATAG

.  M  L  D  H  Y  Q  Q  T  K  N  L  L  V  S  Y  S  T  K  P
      M  .
2581 CAGCGCATGCTGCATTTGGTGGTTACAAACAGTCAGGTATTGGTCGTGAAAACCACAGAA
     GTCGCGTACGACGTAAACCACCAATGTTTGTCAGTCCATAACCAGCACTTTTGGTGTCTT

2641 TGATGCTAGATCATTATCAACAAACCAAAAACTTGTTGGTGAGTTATTCAACAAAACCAA
     ACTACGATCTAGTAATAGTTGTTTGGTTTTTGAACAACCACTCAATAAGTTGTTTTGGTT

End of ACIAD2018
         .  G  F  F  *  SEQ ID NO: 19
2701 TGGGCTTCTTCTAACCCGGGCCCTATATATGGATCCAATTGCAATGATCATCATGACAGA
     ACCCGAAGAAGATTGGGCCCGGGATATATACCTAGGTTAACGTTACTAGTAGTACTGTCT

2761 TCTGCGCGATCGATATCAGCGCTTTAAATTTGCGCATGCTAGCTATAGTTCTAGAGGT
     AGACGCGCGCTAGCTATAGTCGCGAAATTTAAACGCGTACGATCGATATCAAGATCTCCA

2821 ACCGGTTGTTAACGTTAGCCGGCTACGTATACTCCGGAATATTAATAGGCCTAGGATGCA
     TGGCCAACAATTGCAATCGGCCGATGCATATGAGGCCTTATAATTATCCGGATCCTACGT

2881 TATGGCGGCCGCCTGCAGCTGGCGCCATCGATACGCGTACGTCGCGACCGCGGACATGTA
     ATACCGCCGGCGGACGTCGACCGCGGTAGCTATGCGCATGCAGCGCTGGCGCCTGTACAT

2941 CAGAGCTCGAGAAGTACTAGTGGCCACGTGGGCCGTGCACCTTAAGCTTGGCTGTTTTGG
     GTCTCGAGCTCTTCATGATCACCGGTGCACCCGGCACGTGGAATTCGAACCGACAAAACC

3001 CGGATGAGAGAAGATTTTCAGCCTGATACAGATTAAATCAGAACGCAGAAGCGGTCTGAT
     GCCTACTCTCTTCTAAAAGTCGGACTATGTCTAATTTAGTCTTGCGTCTTCGCCAGACTA

3061 AAAACAGAATTTGCCTGGCGGCAGTAGCGCGGTGGTCCCACCTGACCCCATGCCGAACTC
     TTTTGTCTTAAACGGACCGCCGTCATCGCGCCACCAGGGTGGACTGGGGTACGGCTTGAG

3121 AGAAGTGAAACGCCGTAGCGCCGATGGTAGTGTGGGGTCTCCCCATGCGAGAGTAGGGAA
     TCTTCACTTTGCGGCATCGCGGCTACCATCACACCCCAGAGGGGTACGCTCTCATCCCTT rrnB T2 terminator
3181 CTGCCAGGCATCAAATAAAACGAAAGGCTCAGTCGAAAGACTGGGCCTTTCGTTTTATCT
     GACGGTCCGTAGTTTATTTTGCTTTCCGAGTCAGCTTTCTGACCCGGAAAGCAAAATAGA 3241 GTTGTTTGTCGGTGAACGCTCTCCTGAGTAGGACAAATCCGCCGGGAGCGGATTTGAACG
     CAACAAACAGCCACTTGCGAGAGGACTCATCCTGTTTAGGCGGCCCTCGCCTAAACTTGC 3301 TTGCGAAGCAACGGCCCGGAGGGTGGCGGGCAGGACGCCCGCCATAAACTGCCAGGCATC
     AACGCTTCGTTGCCGGGCCTCCCACCGCCCGTCCTGCGGGCGGTATTTGACGGTCCGTAG rrnB T2 terminator
3361 AAATTAAGCAGAAGGCCATCCTGACGGATGGCCTTTTCACCGACGCGAGGCTGGATGGCC
     TTTAATTCGTCTTCCGGTAGGACTGCCTACCGGAAAAGTGGCTGCGCTCCGACCTACCGG 3421 TTCCCCATTATGATTCTTCTCGCTTCCGGCGGCATCGGGATGCCCGCGTTGCAGGCCATG
     AAGGGGTAATACTAAGAAGAGCGAAGGCCGCCGTAGCCCTACGGGCGCAACGTCCGGTAC
     SEQ ID NO: 20
     SEQ ID NO: 21

Gene ID 001 Nucleotide Sequence: Chlorofexus aurantiacus
malonyl-CoA reductase mcr*
ATGTCTGGTACTGGTCGACTGGCAGGTAAAATTGCACTGATCACTGGCGGTGCTGGCAATA
TTGGTTCCGAGCTGACCCGCCGTTTCCTGGCCGAGGGCGCGACCGTCATCATCTCTGGTCG
TAACCGCGCCAAACTGACCGCACTGGCAGAGCGTATGCAAGCAGGACGCTGGTGTGCCGCT
AAGCGTATTGATCTGGAAGTCATGGACGGTAGCGATCCAGTCGCTGTGCGCGCTGGTATTG
AAGCGATTGTGGCTCGCCATGGTCAGATTGATATTCTGGTTAACAATGCTGGTTCCGCGGG
TGCACAGCGTCGCCTGGCCGAAATTCCGCTGACCGAGGCCGAACTGGGTCCGGGCGCTGAG
GAAACTCTGCACGCGTCCATCGCAAATCTGCTGGGTATGGGCTGGCACCTGATGCGCATTG
CGGCTCCACACATGCCGGTTGGTTCCGCAGTTATCAACGTTTCCACCATTTTCAGCCGCGC
TGAATACATGGTCGTATTCCGTACGTTACGCCGAAAGCCGCTCTGAACGCGCTGTCCCAG
CTGGCGGCACGCGAGCTGGGCGCTCGTGGTATTCGTGTCAACACTATCTTCCCGGGTCCGA
TCGAGTCCGACCGTATCCGTACTGTCTTTCAACGCATGGACCAGCTGAAAGGTCGCCCTGA
GGGCGACACCGCTCATCACTTCCTGAACACCATGCGTCTGTGCCGTGCGAACGATCAGGGC
```

APPENDIX-continued

Annotated DNA sequence of the cloned ACIAD2015 and ACIAD2018 genes in pZZ10

```
GCTCTGGAACGTCGCTTCCCGTCCGTGGGTGATGTGGCGGACGCGGCTGTGTTCCTGGCGT
CTGCCGAATCTGCGGCACTGTCTGGTGAGACTATTGAAGTGACTCACGGCATGGAGCTGCC
GGGCGTGCTCTGAGACTAGCCTGCTGGCTCGTACGGATCTGCGCACCATCGACGCTAGCGGT
CGCACCACCCTGATCTGTGCGGGCGACCAGATTGAAGAAGTGATGGCGCTGACCGGTATGC
TGCGTACCTGCGGCTCTGAAGTTATTATCGGCTTCCGCTCCGCAGCAGCGCTGGCCCAGTT
TGAACAGGCGGTCAACGAAAGCCGTCGTCTGGCAGGTGCTGATTTTACTCCACCAATCGCC
CTGCCGCTGGACCCGCGTGATCCGGCAACTATCGATGCTGTGTTTGACTGGGGCGCAGGTG
AAAACACCGGCGGCATCCACGCTGCTGTTATCCTGCCGGCAACCTCTCATGAGCCAGCCCC
TTGTGTGATCGAGGTTGATGACGAGCGTGTTCTGAACTTCCTGGCTGACGAGATTACCGGC
ACGATCGTTATCGCGTCTCGTCTGGCTCGCTACTGGCAGTCTCAGCGCCTGACCCCTGGTG
CACGTGCCCGTGGCCCTCGTGTTATCTTTCTGTCCAATGGCGCGGATCAGAACGGTAACGT
CTATGGCCGTATCCAATCTGCTGCTATCGGCCAACTGATTCGTGTTTGGCGTCACGAAGCT
GAGCTGGATTACCAGCGTGCATCCGCAGCTGGCGATCACGTGCTGCCGCCTGTCGGGCCA
ACCAAATCGTTCGCTTCGCTAACCGCTCTCTGGAGGGCCTGGAGTTTGCATGCGCCTGGAC
GGCCCAGCTGCTGCACTCTCAGCGTCATATCAATGAAATCACTCTGAACATCCCTGCGAAC
ATTAGCGCTACTACCGGTGCTCGTTCTGCTTCTGTCGGTTGGGCGGAATCTCTGATCGGTC
TGCACCTGGGCAAAGTGGCGCTGATCACCGGTGGCTCTGCGGGCATCGGTGGCCAGATCGG
CCGTCTGCTGGCGCTGTCTGGCGCACGCGTGATGCTGGCTGCCACGTGACCGTCACAAACTG
GAGCAGATGCAGGCAATGATTCAGAGCGAGCTGGCGGAAGTCGGCTACACTGACGTTGAAG
ACCGCGTCCACATCGCTCCGGGCTGCGACGTGTCTTCTGAGGCTCAGCTGGCTGATCTGGT
CGAACGCACCCTGTCTGCATTCGGTACGGTGGACTACCTGATCAACAATGCGGGCATTGCC
GGTGTCGAGGAGATGGTGATCGACATGCCAGTCGAAGGTTGGCGCCGCACACGCTGTTCGCGA
ATCTGATCAGCAATTACAGCCTGATGCGTAAACTGGCGCCGCTGATGAAAAAGCAGGGTTC
TGGCTACATCCTGAACGTTTCTTCCTACTTCGGCGGCGAAAAGGATGCGGCCATCCCATAT
CCGAACCGCGCAGATTACGCGGTTTCTAAAGCCGGCCAGCGTGCGATGGCAGAAGTGTTCG
CCCGCTTCCTGGGTCCGGAGATCCAGATTAACGCGATCGCACCGGGTCCGGTTGAAGGTGA
TCGCCTGCGTGGTACGGGTGAACGTCCGGGCCTGTTCGCACGTCGTGCGCGTCTGATCCTG
GAAAACAAGCGCCTGAATGAGCTGCACGCGGCCCTGATTGCAGCCGCGCGTACCGACGAAC
GTTCTATGCACGAGCTGGTGGAGCTGCTGCCGAACGATGTGGCTGCCCTGGAACAGAA
TCCAGCAGCACCGACCGCGCTGCGCGAACTGGCCCGTCGTTTTCGTTCCGAAGGCGATCCG
GCTGCATCCTCCTCAGCGCACTGCTGAACCGTTCTATCGCGGCGAAGCTGCTGGCACGCC
TGCACAATGGTGGTTACGTCCTGCCAGCCGACATCTTCGCAAACTTGCCTAACCCACCGGA
TCCATTCTTTACCCGCGCTCAGATCGACCGTGAAGCGCGTAAAGTTCGTGATGGTATCATG
GGCATGCTGTATCTGCAGCGTATGCCGACGGAGTTCGATGTCGCGATGGCAACCGTCTATT
ACCTGGCCGACCGCAACGTGAGCGGCGAAACCTTCCACCCATCCGGTGGCCTGCGCTATGA
ACGTACGCCGACCGGTGGTGAGCTGTTCGGCCTGCCGAGCCCGGAACGCCTGGCAGAACTG
GTTGGCTCCACCGTGTACCTGATCGGTGAACACCTGACGGAGCACCTGAACCTGCTGGCCC
GTGCGTATCTGGAGCGTTATGGCGCACGTCAAGTTGTTATGATCGTGGAAACCGAAACGGG
TGCCGAAACTATGCGTCGTCTGCTGCACGACCATGTCGAAGCCGGCCGCCTGATGACGATC
GTGGCTGGTGACCAGATCGAAGCAGCCATCGATCAGGCAATTACGCGTTATGGTCGTCCGG
GTCCTGTTGTTTGCACTCCATTCCGCCCGCTGCCAACTGTGCCTCTGGTCGGTCGCAAGGA
CTCCGATTGGAGCACGGTCCTGTCTGAAGCTGAGTTCGCGGAACTGTGCGAGCATCAGCTG
ACTCACCACTTCCGTGTTGCTCGCAAGATCGCACTGTCCGATGGCGCCAGCCTGGCGCTGG
TCACCCCAGAGACTACCGCAACTTCTACCACTGAACAATTCGCTCTGGCAAACTTCATTAA
AACTACGCTGCACGCTTTCACCGCGACCATCGGCGTTGAGTCCGAACGTACGGCGCAGCGT
ATCCTGATCAATCAGGTGGATCTGACTCGTCGTGCGCGCGCCGAAGAACCGCGCGATCCGC
ACGAACGCCAGCAGGAACTGGAGCGCTTCATTGAAGCAGTCCTGCTGGTCACTGCGCCTCT
GCCACCGGAAGCGGACACGCGCTATGCCGGTCGCATCCATCGCGGCCGTGCCATCACTGTC
TGA (SEQ ID NO: 22)
```

Gene ID 001 Protein Sequence: *Chloroflexus aurantiacus* malonyl-CoA reductase mcr*

```
MSGTGRLAGKIALITGGAGNIGSELTRRFLAEGATVIISGRNRAKLTALAERMQAEAGVPA
KRIDLEVMDGSDPVAVRAGIEAIVARHGQIDILVNNAGSAGAQRRLAEIPLTEAELGPGAE
ETLHASIANLLGMGWHLMRIAAPHMPVGSAVINVSTIFSRAEYYGRIPYVTPKAALNALSQ
LAARELGARGIRVNTIFPGPIESDRIRTVFQRMDQLKGRPEGDTAHHFLNTMRLCRANDQG
ALERREPSVGDVADAAVFLASAESAALSGETIEVTHGMELPACSETSLLARTDLRTIDASG
RTTLICAGDQIEEVMALTGMLRTCGSEVIIGFRSAAALAQFEQAVNESRRLAGADFTPPIA
LPLDPRDPATIDAVEDWGAGENTGGIHAAVILPATSHEPAPCVIEVDDERVLNFLADEITG
TIVIASRLARYWQSQRLTPGARARGPRVIFLSNGADQNGNVYGRIQSAAIGQLIRVWRHEA
ELDYQRASAAGDHVLPPVWANQIVRFANRSLEGLEFACAWTAQLLHSQRHINEITLNIPAN
ISATTGARSASVGWAESLIGLHLGKVALITGGSAGIGGQIGRLLALSGARVMLAARDRHKL
EQMQAMIQSELAEVGYTDVEDRVHIAPGCDVSSEAQLADLVERTLSAFGTVDYLINNAGIA
GVEEMVIDMPVEGWRHTLFANLISNYSLMRKLAPLMKKQGSGYILNVSSYEGGEKDAAIPY
PNRADYAVSKAGQRAMAEVFARFLGPEIQINAIAPGPVEGDRLRGTGERPGLFARRARLIL
ENKRLNELHAALIAAARTDERSMHELVELLLPNDVAALEQNPAAPTALRELARRFRSEGDP
AASSSSALLNRSIAAKLLARLHNGGYVLPADIFANLPNPPDPFFTRAQIDREARKVRDGIM
GMLYLQRMPTEFDVAMATVYYLADRNVSGETFHPSGGLRYERTPTGGELFGLPSPERLAEL
VGSTVYLIGEHLTEHLNLLARAYLERYGARQVVMIVETETGAETMRRLLHDHVEAGRLMTI
VAGDQIEAAIDQAITRYGRPGPVVQTPFFRPLPTVPLVGRKDSDWSTVLSEAEFAELCEHQL
THHFRVARKIALSDGASLALVTPETTATSTTEQFALANFIKTTLHAFTATIGVESERTAQR
ILINQVDLTRRARAEEPRDPHERQQELERFIEAVLLVTAPLPPEADTRYAGRIHRGRAITV
(SEQ ID NO: 23)
```

What is claimed is:

1. An organism that is genetically engineered to express an alcohol dehydrogenase and an aldehyde dehydrogenase and to convert ethanol to acetyl-CoA when grown on ethanol as a sole carbon source,
wherein the organism is genetically engineered to express A. baylyi ADP1 genes ACIAD2015 and ACIAD2018, wherein the organism is further genetically engineered to produce a polyhydroxyalkanoate polymer.

2. The organism of claim 1, wherein the organism produces polyhydroxyalkanoate polymer when grown on ethanol as a sole carbon source.

3. The organism of claim 1, wherein the polyhydroxyalkanoate polymer is selected from the group consisting of: polyglycolic acid (PGA), poly-3-hydroxybutyrate (P3HB), poly-3-hydroxypropionate (P3HP), poly-4-hydroxybutyrate (P4HB), poly-5-hydroxyvalerate (P5HV), poly-3-hydroxybutyrate-co-4-hydroxybutyrate (P(3HB-co-4HB)), poly-3-hydroxybutyrate-co-5-hydroxyvalerate (P(3HB-co-5HV)), and copolymers thereof.

4. The organism of claim 1, wherein the organism is selected from the group consisting of: *Escherichia coli, Ralstonia eutropha, Acinetobacter baumannii, Acinetobacter baylyi, Acinetobacter aceti, Acinetobacter* sp. DRI, *Acinetobacter calcoaceticus, Acinetobacter haemolyticus, Acinetobacter johnsonii, Acinetobacter junii, Acinetobacter lwoffii, Acinetobacter radioresistens, Acinetobacter venetianus, Acinetobacter* sp. DSM, *Zoogloea ramigera, Allochromatium vinosum, Rhodococcus ruber, Delftia acidovorans, Aeromonas caviae, Synechocystis* sp. PCC 6803, *Synechococcus elongatus* PCC 7942, *Thiocapsa pfenigii, Bacillus megaterium, Clostridium kluyveri, Methylobacterium extorquens, Nocardia corralina, Nocardia salmonicolor, Pseudomonas fluorescens, Pseudomonas oleovorans, Pseudomonas* sp. 6-19, *Pseudomonas* sp. 61-3 and *Pseudomonas putida, Rhodobacter sphaeroides, Alcaligenes latus, Klebsiella oxytoca, Anaerobiospirillum succiniciproducens, Actinobacillus succinogenes, Mannheimia succiniciproducens, Rhizobium etli, Bacillus subtilis, Corynebacterium glutamicum, Gluconobacter oxydans, Zymomonas mobilis, Lactococcus lactis, Lactobacillus plantarum, Streptomyces coelicolor, Clostridium acetobutylicum, Saccharomyces cerevisiae, Schizosaccharomyces pombe, Kiuyveromyces iactis, Kiuyveromyces marxianus, Aspergillus terreus, Aspergillus niger, Pichia pastoris, Chiarella* spp., *Chiarella minutissima, Chiarella emersonii, Chiarella sorokiniana, Chiarella ellipsoidea, Chiarella* sp., and *Chiarella protothecoides*.

5. The organism of claim 1, wherein the organism if further genetically engineered to delete a native genomic copy of gene gabD (Succinate semialdehyde dehydrogenase, NADP+-dependent) and a native genomic copy of gene yneI (Succinate semialdehyde dehydrogenase, NAD(P)+-dependent).

6. The organism of claim 5, wherein the organism is further genetically engineered to express a *C. kluyveri* gene org (CoA-transferase).

* * * * *

SEQUENCE LISTING

<160> NUMBER OF SEQ ID NOS: 23

<210> SEQ ID NO 1
<211> LENGTH: 40
<212> TYPE: DNA
<213> ORGANISM: Artificial Sequence
<220> FEATURE:
<223> OTHER INFORMATION: E. coli

<400> SEQUENCE: 1
cccggatcca ggaggttttt atgggaagtt taatgaaagc                              40

<210> SEQ ID NO 2
<211> LENGTH: 45
<212> TYPE: DNA
<213> ORGANISM: Artificial Sequence
<220> FEATURE:
<223> OTHER INFORMATION: E. coli

<400> SEQUENCE: 2
tcgatataac gcataaaaac ctcctttaga gtttaaggtc aatca                        45

<210> SEQ ID NO 3
<211> LENGTH: 45
<212> TYPE: DNA
<213> ORGANISM: Artificial Sequence
<220> FEATURE:
<223> OTHER INFORMATION: E. coli

<400> SEQUENCE: 3
accttaaact ctaaaggagg tttttatgcg ttatatcgat cctaa                        45

<210> SEQ ID NO 4
<211> LENGTH: 29
<212> TYPE: DNA
<213> ORGANISM: Artificial Sequence
<220> FEATURE:
<223> OTHER INFORMATION: E. coli

<400> SEQUENCE: 4
ccctcatgat tagaagaagc ccattggtt                                          29

<210> SEQ ID NO 5
<211> LENGTH: 45
<212> TYPE: DNA
<213> ORGANISM: Artificial Sequence
<220> FEATURE:
<223> OTHER INFORMATION: E. coli

<400> SEQUENCE: 5
cccgacgtca ggaggttttt atggctttta aaatattgc tgacc                         45

<210> SEQ ID NO 6
<211> LENGTH: 45
<212> TYPE: DNA
<213> ORGANISM: Artificial Sequence
<220> FEATURE:
<223> OTHER INFORMATION: E. coli

<400> SEQUENCE: 6
aacgcataaa aacctccttc taggtttaca atgctgctgt gaaaa                        45

<210> SEQ ID NO 7
<211> LENGTH: 45
<212> TYPE: DNA
<213> ORGANISM: Artificial Sequence

```
<220> FEATURE:
<223> OTHER INFORMATION: E. coli

<400> SEQUENCE: 7
attgtaaacc tagaaggagg tttttatgcg ttatatcgat cctaa          45

<210> SEQ ID NO 8
<211> LENGTH: 34
<212> TYPE: DNA
<213> ORGANISM: Artificial Sequence
<220> FEATURE:
<223> OTHER INFORMATION: E. coli

<400> SEQUENCE: 8
gggcccgggt tagaagaagc ccattggttt tgtt                      34

<210> SEQ ID NO 9
<211> LENGTH: 30
<212> TYPE: DNA
<213> ORGANISM: Artificial Sequence
<220> FEATURE:
<223> OTHER INFORMATION: E. coli

<400> SEQUENCE: 9
atgcgtgcac gtgtaggctg gagctgcttc                           30

<210> SEQ ID NO 10
<211> LENGTH: 30
<212> TYPE: DNA
<213> ORGANISM: Artificial Sequence
<220> FEATURE:
<223> OTHER INFORMATION: E. coli

<400> SEQUENCE: 10
atgcagtact atgggaatta gccatggtcc                           30

<210> SEQ ID NO 11
<211> LENGTH: 30
<212> TYPE: DNA
<213> ORGANISM: Artificial Sequence
<220> FEATURE:
<223> OTHER INFORMATION: E. coli

<400> SEQUENCE: 11
cccgtcgaca attctcatgt ttgacagctt                           30

<210> SEQ ID NO 12
<211> LENGTH: 30
<212> TYPE: DNA
<213> ORGANISM: Artificial Sequence
<220> FEATURE:
<223> OTHER INFORMATION: E. coli

<400> SEQUENCE: 12
cccgagctct tagaagaagc ccattggttt                           30

<210> SEQ ID NO 13
<211> LENGTH: 30
<212> TYPE: DNA
<213> ORGANISM: Artificial Sequence
<220> FEATURE:
<223> OTHER INFORMATION: E. coli

<400> SEQUENCE: 13
ccctctagaa attctcatgt ttgacagctt                           30
```

<210> SEQ ID NO 14
<211> LENGTH: 300
<212> TYPE: DNA
<213> ORGANISM: E. coli

<400> SEQUENCE: 14

```
tctagatttc agtgcaattt atctcttcaa atgtagcacc tgaagtcagc cccatacgat      60
ataagttgta attctcatgt ttgacagctt atcatcgata agctttaatg cggtagttta     120
tcacagttaa attgctaacg cagtcaggca ccgtgtatga aatctaacaa tgcgctcatc     180
gtcatcctcg gcaccgtcac cctggatgct gtaggcatag gcttggttat gccggtactg     240
ccgggcctct gcgggatgt cgtggaatgc cttcgaattc agcacctgca catgggacgt     300
```

<210> SEQ ID NO 15
<211> LENGTH: 300
<212> TYPE: DNA
<213> ORGANISM: E. coli

<400> SEQUENCE: 15

```
agatctaaag tcacgttaaa tagagaagtt tacatcgtgg acttcagtcg gggtatgcta      60
tattcaacat taagagtaca aactgtcgaa tagtagctat tcgaaattac gccatcaaat     120
agtgtcaatt taacgattgc gtcagtccgt ggcacatact ttagattgtt acgcgagtag     180
cagtaggagc cgtggcagtg ggacctacga catccgtatc cgaaccaata cggccatgac     240
ggcccggaga acgccctaca gcaccttacg gaagcttaag tcgtggacgt gtaccctgca     300
```

<210> SEQ ID NO 16
<211> LENGTH: 390
<212> TYPE: PRT
<213> ORGANISM: E. coli

<400> SEQUENCE: 16

Met Ala Phe Lys Asn Ile Ala Asp Gln Thr Asn Gly Phe Tyr Ile Pro
 1               5                  10                  15

Cys Val Ser Leu Phe Gly Pro Gly Cys Ala Lys Glu Ile Gly Thr Lys
            20                  25                  30

Ala Gln Asn Leu Gly Ala Lys Lys Ala Leu Ile Val Thr Asp Ala Gly
        35                  40                  45

Leu Phe Lys Phe Gly Val Ala Asp Thr Ile Ala Ala Tyr Leu Lys Glu
    50                  55                  60

Ala Gly Val Asp Ser His Ile Phe Pro Gly Ala Glu Pro Asn Pro Thr
65                  70                  75                  80

Asp Lys Asn Val His Asn Gly Val Asp Ala Tyr Asn Thr Asn Gly Cys
                85                  90                  95

Asp Phe Ile Val Ser Leu Gly Gly Gly Ser Ser His Asp Cys Ala Lys
            100                 105                 110

Gly Ile Gly Leu Val Thr Ala Gly Gly His Ile Arg Asp Tyr Glu
        115                 120                 125

Gly Ile Asp Lys Ser Thr Val Pro Met Thr Pro Leu Ile Ala Val Asn
    130                 135                 140

Thr Thr Ala Gly Thr Ala Ser Glu Met Thr Arg Phe Cys Ile Ile Thr
145                 150                 155                 160

Asn Thr Asp Thr His Val Lys Met Ala Ile Val Asp Trp Arg Cys Thr
                165                 170                 175

Pro Leu Ile Ala Ile Asp Asp Pro Lys Leu Met Ile Ala Lys Pro Ala
            180                 185                 190

```
Ser Leu Thr Ala Ala Thr Gly Met Asp Ala Leu Thr His Ala Val Glu
        195                 200                 205

Ala Tyr Val Ser Thr Ala Ala Asn Pro Ile Thr Asp Ala Cys Ala Glu
    210                 215                 220

Lys Ala Ile Ser Met Ile Ser Glu Trp Leu Ser Pro Ala Val Ala Asn
225                 230                 235                 240

Gly Glu Asn Leu Glu Ala Arg Asp Ala Met Ser Tyr Ala Gln Tyr Leu
                245                 250                 255

Ala Gly Met Ala Phe Asn Asn Ala Ser Leu Gly Tyr Val His Ala Met
            260                 265                 270

Ala His Gln Leu Gly Gly Phe Tyr Asn Leu Pro His Gly Val Cys Asn
        275                 280                 285

Ala Val Leu Leu Pro His Val Cys Glu Phe Asn Leu Ile Ala Cys Pro
    290                 295                 300

Glu Arg Tyr Ala Arg Ile Ala Glu Leu Met Gly Val Asn Thr His Gly
305                 310                 315                 320

Leu Thr Val Thr Glu Ala Ala Tyr Ala Ala Ile Asp Ala Ile Arg Thr
                325                 330                 335

Leu Ser Lys Ser Ile Gly Ile Pro Ser Gly Leu Thr Glu Leu Gly Val
            340                 345                 350

Lys Thr Glu Asp Leu Ala Val Met Ala Glu Asn Ala Gln Lys Asp Ala
        355                 360                 365

Cys Met Leu Thr Asn Pro Arg Lys Ala Asn His Ala Gln Val Val Asp
    370                 375                 380

Ile Phe Thr Ala Ala Leu
385                 390

<210> SEQ ID NO 17
<211> LENGTH: 1200
<212> TYPE: DNA
<213> ORGANISM: E. coli

<400> SEQUENCE: 17
cagaggtttt tatggctttt aaaaatattg ctgaccaaac aaacggtttt tatatccctt      60
gtgtctccct ttttggccct ggttgtgcca agaaattgg taccaaagca caaaatttag     120
gtgcaaaaaa agcactcatc gtgactgatg ctggtttatt aaatttggt gtagctgaca     180 ctatcgcagc ataccttaaa gaagctggcg tagacagtca tattttccca ggcgctgaac     240
ccaatccgac agataaaaac gtacataatg gcgttgatgc atataatacc aatggatgtg     300
actttattgt atcgctcggt ggtggatcat ctcacgactg tgcaaaaggt attggattag     360
ttaccgcagg cggtggtcac attcgtgatt acgaaggaat tgataaaagt actgttccaa     420
tgacgccgtt aattgcagtc aataccactg caggcacagc atctgaaatg acacgtttct     480
gtattattac caatacagat acacatgtaa aaatggcgat tgtagattgg cgttgtaccc     540
cactgattgc cattgatgac cctaagctca tgattgctaa gcctgcaagc ctgactgctg     600
cgactggtat ggatgcgctg acacatgctg tcgaagctta tgtatctact gctgcgaacc     660
caatcacaga cgcctgtgcc gaaaaagcaa tcagcatgat cagtgaatgg ctcagcccag     720
ctgttgccaa tggtgaaaac cttgaagcac gtgatgcaat gagctatgcc caatatcttg     780
caggtatggc atttaacaat gcgtcattag gttatgttca tgccatggcg caccaacttg     840
gcggtttcta caatctgcca cacggcgtat gtaatgcggt attgttgcca cacgtttgtg     900
agttcaaccc tgattgcttg ccagagcgtt atgcacgtat cgcagaatta atgggcgtaa     960
```

-continued

```
atacacacgg ccttacggtg actgaagctg catatgctgc aatcgatgca attcgtacat    1020
tatcaaaatc aattggtatc ccatctggct tgaccgagct tggtgtaaaa actgaagatc    1080
ttgcagtaat ggccgaaaat gcacaaaaag acgcgtgtat gttgactaat ccacgcaaag    1140
caaatcacgc tcaagttgta gatattttca cagcagcatt gtaaacctag aaggaggttt    1200
```

<210> SEQ ID NO 18
<211> LENGTH: 1200
<212> TYPE: DNA
<213> ORGANISM: E. coli

<400> SEQUENCE: 18

```
gtctccaaaa ataccgaaaa tttttataac gactggtttg tttgccaaaa atatagggaa      60
cacagaggga aaaaccggga ccaacacggt ttctttaacc atggtttcgt gttttaaatc     120
cacgttttt tcgtgagtag cactgactac gaccaaataa atttaaacca catcgactgt     180
gatagcgtcg tatggaattt cttcgaccgc atctgtcagt ataaaagggt ccgcgacttg     240
ggttaggctg tctattttg catgtattac cgcaactacg tatattatgg ttacctacac     300
tgaaataaca tagcgagcca ccacctagta gagtgctgac acgttttcca taacctaatc     360
aatggcgtcc gccaccagtg taagcactaa tgcttcctta actattttca tgacaaggtt     420
actgcggcaa ttaacgtcag ttatggtgac gtccgtgtcg tagactttac tgtgcaaaga     480
cataataatg gttatgtcta tgtgtacatt tttaccgcta acatctaacc gcaacatggg     540
gtgactaacg gtaactactg ggattcgagt actaacgatt cggacgttcg gactgacgac     600
gctgaccata cctacgcgac tgtgtacgac agcttcgaat acatagatga cgacgcttgg     660
gttagtgtct gcggacacgg cttttcgtt agtcgtacta gtcacttacc gagtcgggtc     720
gacaacggtt accacttttg gaacttcgtg cactacgtta ctcgatacgg ttatagaac      780
gtccataccg taaattgtta cgcagtaatc caatacaagt acggtaccgc gtggttgaac    840
cgccaaagat gttagacggt gtgccgcata cattacgcca taacaacggt gtgcaaacac     900
tcaagttgga ctaacgaacg ggtctcgcaa tacgtgcata gcgtcttaat tacccgcatt     960
tatgtgtgcc ggaatgccac tgacttcgac gtatacgacg ttagctacgt taagcatgta    1020
atagttttag ttaaccatag ggtagaccga actggctcga accacatttt tgacttctag    1080
aacgtcatta ccggctttta cgtgttttc tgcgcacata caactgatta ggtgcgtttc    1140
gtttagtgcg agttcaacat ctataaaagt gtcgtcgtaa catttggatc ttcctccaaa    1200
```

<210> SEQ ID NO 19
<211> LENGTH: 503
<212> TYPE: PRT
<213> ORGANISM: E. coli

<400> SEQUENCE: 19

```
Met Arg Tyr Ile Asp Pro Asn Gln Pro Gly Ser Lys Val Gln Phe Lys
  1               5                  10                  15

Ala Gln Tyr Glu Asn Phe Ile Gly Gly Gln Trp Val Pro Val Lys
                 20                  25                  30

Gly Glu Tyr Phe Gly Asn Ser Ser Pro Val Asp Gly Lys Val Phe Thr
             35                  40                  45

Gln Ile Pro Arg Ser Ser Val Glu Asp Ile Glu Leu Ala Leu Asp Ala
         50                  55                  60

Ala His Lys Ala Lys Ala Asp Trp Asn Lys Ala Ser Pro Thr Val Arg
 65                  70                  75                  80
```

```
Ser Asn Val Leu Leu Lys Ile Ala Asp Arg Leu Glu Asn Leu Glu
                85                  90                  95

Leu Leu Ala Val Ala Glu Thr Trp Glu Asn Gly Lys Pro Ile Arg Glu
            100                 105                 110

Thr Leu Ala Ala Asp Ile Pro Leu Ala Ile Asp His Phe Arg Tyr Phe
            115                 120                 125

Ala Gly Cys Ile Arg Ala Gln Glu Gly Gly Ile Ser Glu Ile Asp Glu
130                 135                 140

Asp Thr Ile Ala Tyr His Phe His Glu Pro Leu Gly Val Val Gly Gln
145                 150                 155                 160

Ile Ile Pro Trp Asn Phe Pro Ile Leu Met Ala Ala Trp Lys Leu Ala
                165                 170                 175

Pro Ala Leu Ala Ala Gly Asn Cys Ile Val Leu Lys Pro Ala Glu Gln
            180                 185                 190

Thr Pro Ser Ser Ile Leu Val Leu Ala Glu Leu Ile Gln Asp Leu Leu
            195                 200                 205

Pro Pro Gly Val Leu Asn Ile Val Asn Gly Tyr Gly Ala Glu Val Gly
210                 215                 220

Arg Pro Leu Ala Thr Asn Pro Arg Ile Ser Lys Ile Ala Phe Thr Gly
225                 230                 235                 240

Ser Thr Lys Val Gly Gln Met Ile Met Gln Tyr Ala Thr Glu Asn Ile
                245                 250                 255

Ile Pro Val Thr Leu Glu Leu Gly Gly Lys Ser Pro Asn Ile Phe Phe
            260                 265                 270

Glu Asp Ile Leu Asp Lys Glu Asp Tyr Leu Glu Lys Thr Leu Glu
            275                 280                 285

Gly Phe Ala Met Phe Ala Leu Asn Gln Gly Glu Val Cys Thr Cys Pro
290                 295                 300

Ser Arg Ala Leu Val Gln Glu Ser Ile Ala Asp Lys Phe Leu Glu Met
305                 310                 315                 320

Ala Val Glu Arg Val Lys Arg Ile Lys Thr Gly His Pro Leu Asp Thr
                325                 330                 335

Glu Thr Met Ile Gly Ala Gln Ala Ser Lys Gln Phe Asp Lys Ile
            340                 345                 350

Leu Gly Cys Ile Asp Thr Gly Arg Asn Glu Gly Ala Gln Leu Leu Thr
            355                 360                 365

Gly Gly Asp Ala Arg His Asp Val Asp Gly Gly Phe Tyr Ile Glu Pro
370                 375                 380

Thr Ile Phe Lys Gly Asn Asn Ser Met Lys Ile Phe Gln Glu Glu Ile
385                 390                 395                 400

Phe Gly Pro Val Leu Ser Val Thr Thr Phe Lys Asp Phe Asp Asp Ala
                405                 410                 415

Met Arg Ile Ala Asn Asp Thr Ile Tyr Gly Leu Gly Ala Gly Val Trp
            420                 425                 430

Ser Arg Ser Ala His Thr Ser Tyr Arg Ala Gly Arg Ala Ile Glu Ala
            435                 440                 445

Gly Arg Val Trp Thr Asn Cys Tyr His Leu Tyr Pro Ala His Ala Ala
450                 455                 460

Phe Gly Gly Tyr Lys Gln Ser Gly Ile Gly Arg Glu Asn His Arg Met
465                 470                 475                 480

Met Leu Asp His Tyr Gln Gln Thr Lys Asn Leu Leu Val Ser Tyr Ser
                485                 490                 495
```

Thr Lys Pro Met Gly Phe Phe
         500

<210> SEQ ID NO 20
<211> LENGTH: 2280
<212> TYPE: DNA
<213> ORGANISM: E. coli

<400> SEQUENCE: 20

| | | | | | |
|---|---|---|---|---|---|
| ttatgcgtta | tatcgatcct | aatcaacctg | gctctaaggt | tcaatttaaa | gcacaatatg | 60 |
| aaaactttat | tggcggtcag | tgggttcctc | ctgtaaaagg | agaatacttc | ggaaatagct | 120 |
| ctcctgtcga | tggcaaagta | tttactcaaa | ttcctcgctc | aagcgtcgaa | gatattgaac | 180 |
| tagcacttga | tgcagcgcac | aaagcgaaag | ctgattggaa | taaagcatca | cctacagttc | 240 |
| gttcaaatgt | tttacttaaa | attgcagatc | gtctggaaga | aaacctagag | ctacttgctg | 300 |
| tagcagaaac | atgggaaaat | ggtaaaccta | tccgcgaaac | actcgcagca | gatatcccac | 360 |
| ttgcaattga | ccatttccgc | tatttcgcag | gctgtatacg | tgcacaagaa | ggtggtattt | 420 |
| cagaaattga | tgaggatacc | attgcttatc | atttccatga | accgcttggt | gttgtaggcc | 480 |
| agatcattcc | atggaacttt | ccaattttga | tggctgcatg | gaaattggca | ccagcactgg | 540 |
| cagcaggtaa | ctgtattgtt | cttaaaccag | cagagcaaac | accgtcaagt | attctagttc | 600 |
| tggctgaatt | gattcaggac | ctccttccac | ctggcgtact | taatatcgtc | aatggatacg | 660 |
| gtgctgaggt | tggtcgtcct | ttagcgacaa | atccaagaat | tcaaaaaatt | gcattcactg | 720 |
| gttcaaccaa | agttggacaa | atgatcatgc | aatatgccac | tgaaaatatc | attcctgtaa | 780 |
| cgctagaact | tggtggtaaa | tctccaaata | tcttttttga | agacatctta | gataaagaag | 840 |
| atgattattt | ggaaaaaaca | cttgaaggtt | ttgccatgtt | tgccttgaac | cagggtgaag | 900 |
| tatgtacctg | cccttcacgt | gcacttgttc | aggaaagtat | tgctgacaaa | ttccttgaaa | 960 |
| tggctgtaga | gcgtgtcaaa | cgcatcaaga | cgggtcatcc | acttgataca | gaaaccatga | 1020 |
| ttggcgcaca | agcctctaag | caacagtttg | ataaaatttt | aggctgtatt | gatacaggtc | 1080 |
| gtaatgaagg | tgcacaactt | ttaactggtg | gtgatgcacg | tcacgatgta | gatggtggtt | 1140 |
| tttatattga | accaacgatt | tcaaaggca | ataacagtat | gaaaatcttc | caagaagaaa | 1200 |
| tttttggacc | agtactttca | gtaacgacat | ttaaagattt | tgacgatgca | atgcgtattg | 1260 |
| ccaacgacac | gatttatggc | ttgggtgctg | gtgtatggtc | acgttctgca | catacctcat | 1320 |
| accgtgctgg | tcgtgcgatt | gaagccggtc | gtgtgtggac | aaactgttat | cacctttatc | 1380 |
| cagcgcatgc | tgcatttggt | ggttacaaac | agtcaggtat | tggtcgtgaa | accacagaa | 1440 |
| tgatgctaga | tcattatcaa | caaaccaaaa | acttgttggt | gagttattca | acaaaaccaa | 1500 |
| tgggcttctt | ctaacccggg | ccctatatat | ggatccaatt | gcaatgatca | tcatgacaga | 1560 |
| tctgcgcgcg | atcgatatca | gcgctttaaa | tttgcgcatg | ctagctatag | ttctagaggt | 1620 |
| accggttgtt | aacgttagcc | ggctacgtat | actccggaat | attaataggc | ctaggatgca | 1680 |
| tatggcggcc | gcctgcagct | ggcgccatcg | atacgcgtac | gtcgcgaccg | cggacatgta | 1740 |
| cagagctcga | gaagtactag | tggccacgtg | ggccgtgcac | cttaagcttg | gctgttttgg | 1800 |
| cggatgagag | aagattttca | gcctgataca | gattaaatca | gaacgcagaa | gcggtctgat | 1860 |
| aaaacagaat | ttgcctggcg | gcagtagcgc | ggtggtccca | cctgacccca | tgccgaactc | 1920 |
| agaagtgaaa | cgccgtagcg | ccgatggtag | tgtgggtct | ccccatgcga | gagtagggaa | 1980 |
| ctgccaggca | tcaaataaaa | cgaaaggctc | agtcgaaaga | ctgggccttt | cgttttatct | 2040 |

-continued

```
gttgtttgtc ggtgaacgct ctcctgagta ggacaaatcc gccgggagcg gatttgaacg     2100
ttgcgaagca acggcccgga gggtggcggg caggacgccc gccataaact gccaggcatc     2160
aaattaagca gaaggccatc ctgacggatg gccttttcac cgacgcgagg ctggatggcc     2220
ttccccatta tgattcttct cgcttccggc ggcatcggga tgcccgcgtt gcaggccatg     2280
```

<210> SEQ ID NO 21
<211> LENGTH: 2280
<212> TYPE: DNA
<213> ORGANISM: E. coli

<400> SEQUENCE: 21

```
aatacgcaat atagctagga ttagttggac cgagattcca agttaaattt cgtgttatac       60
ttttgaaata accgccagtc acccaaggag gacattttcc tcttatgaag cctttatcga      120
gaggacagct accgtttcat aaatgagttt aaggagcgag ttcgcagctt ctataacttg      180
atcgtgaact acgtcgcgtg tttcgctttc gactaacctt atttcgtagt ggatgtcaag      240
caagtttaca aaatgaattt taacgtctag cagaccttct tttggatctc gatgaacgac      300
atcgtctttg tacccttttta ccatttggat aggcgctttg tgagcgtcgt ctataggggtg     360 aacgttaact ggtaaaggcg ataaagcgtc cgacatatgc acgtgttctt ccaccataaa      420
gtctttaact actcctatgg taacgaatag taaaggtact tggcgaacca caacatccgg      480
tctagtaagg taccttgaaa ggttaaaact accgacgtac ctttaaccgt ggtcgtgacc      540
gtcgtccatt gacataacaa gaatttggtc gtctcgtttg tggcagttca taagatcaag      600
accgacttaa ctaagtcctg gaggaaggtg gaccgcatga attatagcag ttacctatgc      660
cacgactcca accagcagga aatcgctgtt taggttctta aagtttttaa cgtaagtgac      720
caagttggtt tcaacctgtt tactagtacg ttatacggtg acttttatag taaggacatt      780
gcgatcttga accaccattt agaggtttat agaaaaaact tctgtagaat ctatttcttc      840
tactaataaa ccttttttgt gaacttccaa aacggtacaa acggaacttg gtcccacttc      900
atacatggac gggaagtgca cgtgaacaag tcctttcata acgactgttt aaggaacttt      960
accgacatct cgcacagttt gcgtagttct gcccagtagg tgaactatgt ctttggtact     1020
aaccgcgtgt tcggagattc gttgtcaaac tattttaaaa tccgacataa ctatgtccag     1080
cattacttcc acgtgttgaa aattgaccac cactacgtgc agtgctacat ctaccaccaa     1140
aaatataact tggttgctaa aagtttccgt tattgtcata cttttagaag gttcttcttt     1200
aaaaacctgg tcatgaaagt cattgctgta aatttctaaa actgctacgt tacgcataac     1260
ggttgctgtg ctaaataccg aacccacgac cacataccag tgcaagacgt gtatggagta     1320
tggcacgacc agcacgctaa cttcggccag cacacacctg tttgacaata gtggaaatag     1380
gtcgcgtacg acgtaaacca ccaatgtttg tcagtccata accagcactt ttggtgtctt     1440
actacgatct agtaatagtt gtttggtttt tgaacaacca ctcaataagt tgttttggtt     1500
acccgaagaa gattgggccc gggatatata cctaggttaa cgttactagt agtactgtct     1560
agacgcgcgc tagctatagt cgcgaaattt aaacgcgtac gatcgatatc aagatctcca     1620
tggccaacaa ttgcaatcgg ccgatgcata tgaggcctta taattatccg gatcctacgt     1680
ataccgccgg cggacgtcga ccgcggtagc tatgcgcatg cagcgctggc gcctgtacat     1740
gtctcgagct cttcatgatc accggtgcac ccggcacgtg gaattcgaac cgacaaaacc     1800
gcctactctc ttctaaaagt cggactatgt ctaatttagt cttgcgtctt cgccagacta     1860
ttttgtctta aacggaccgc cgtcatcgcg ccaccagggt ggactggggt acggcttgag     1920
```

```
tcttcacttt gcggcatcgc ggctaccatc acaccccaga ggggtacgct ctcatccctt     1980
gacggtccgt agtttatttt gctttccgag tcagctttct gacccggaaa gcaaaataga     2040
caacaaacag ccacttgcga gaggactcat cctgtttagg cggccctcgc ctaaacttgc     2100
aacgcttcgt tgccgggcct cccaccgccc gtcctgcggg cggtatttga cggtccgtag     2160
tttaattcgt cttccggtag gactgcctac cggaaaagtg gctgcgctcc gacctaccgg     2220 aagggtaat  actaagaaga gcgaaggccg ccgtagccct acgggcgcaa cgtccggtac     2280

<210> SEQ ID NO 22
<211> LENGTH: 3663
<212> TYPE: DNA
<213> ORGANISM: Chloroflexus aurantiacus

<400> SEQUENCE: 22
atgtctggta ctggtcgact ggcaggtaaa attgcactga tcactggcgg tgctggcaat       60
attggttccg agctgacccg ccgtttcctg gccgagggcg cgaccgtcat catctctggt      120
cgtaaccgcg ccaaactgac cgcactggca gagcgtatgc aagcagaggc tggtgtgccg      180
gctaagcgta ttgatctgga agtcatggac ggtagcgatc cagtcgctgt gcgcgctggt      240
attgaagcga ttgtggctcg ccatggtcag attgatattc tggttaacaa tgctggttcc      300
gcgggtgcac agcgtcgcct ggccgaaatt ccgctgaccg aggccgaact gggtccgggc      360
gctgaggaaa ctctgcacgc gtccatcgca aatctgctgg gtatgggctg gcacctgatg      420
cgcattgcgg ctccacacat gccggttggt tccgcagtta tcaacgtttc caccattttc      480
agccgcgctg aatactatgg tcgtattccg tacgttacgc cgaaagccgc tctgaacgcg      540
ctgtcccagc tggcggcacg cgagctgggc gctcgtggta ttcgtgtcaa cactatcttc      600
ccgggtccga tcgagtccga ccgtatccgt actgtctttc aacgcatgga ccagctgaaa      660
ggtcgccctg agggcgacac cgctcatcac ttcctgaaca ccatgcgtct gtgccgtgcg      720
aacgatcagg gcgctctgga acgtcgcttc ccgtccgtgg gtgatgtggc ggacgcggct      780
gtgttcctgg cgtctgccga atctgcggca ctgtctggtg agactattga agtgactcac      840
ggcatggagc tgccggcgtg ctctgagact agcctgctgg ctcgtacgga tctgcgcacc      900
atcgacgcta gcgtcgcac caccctgatc tgtgcgggcg accagattga agaagtgatg      960
gcgctgaccg gtatgctgcg tacctgcggc tctgaagtta ttatcggctt ccgctccgca     1020
gcagcgctgg cccagtttga acaggcggtc aacgaaagcc gtcgtctggc aggtgctgat     1080
tttactccac caatcgccct gccgctggac ccgcgtgatc cggcaactat cgatgctgtg     1140
tttgactggg gcgcaggtga aaacaccggc ggcatccacg ctgctgttat cctgccggca     1200
acctctcatg agccagcccc ttgtgtgatc gaggttgatg acgagcgtgt tctgaacttc     1260
ctggctgacg agattaccgg cacgatcgtt atcgcgtctc gtctggctcg ctactggcag     1320
tctcagcgcc tgacccctgg tgcacgtgcc cgtggccctc gtgttatctt tctgtccaat     1380
ggcgcggatc agaacggtaa cgtctatggc cgtatccaat ctgctgctat cggccaactg     1440
attcgtgttt ggcgtcacga agctgagctg gattaccagc gtgcatccgc agctggcgat     1500
cacgtgctgc cgcctgtctg ggccaaccaa atcgttcgct tcgctaaccg ctctctggag     1560
ggcctggagt ttgcatgcgc ctggacggcc cagctgctgc actctcagcg tcatatcaat     1620
gaaatcactc tgaacatccc tgcgaacatt agcgctacta ccggtgctcg ttctgcttct     1680
gtcggttggg cggaatctct gatcggtctg cacctgggca aagtggcgct gatcaccggt     1740
```

-continued

```
ggctctgcgg gcatcggtgg ccagatcggc cgtctgctgg cgctgtctgg cgcacgcgtg      1800
atgctggctg cacgtgaccg tcacaaactg gagcagatgc aggcaatgat tcagagcgag      1860
ctggcggaag tcggctacac tgacgttgaa gaccgcgtcc acatcgctcc gggctgcgac      1920
gtgtcttctg aggctcagct ggctgatctg gtcgaacgca ccctgtctgc attcggtacg      1980
gtggactacc tgatcaacaa tgcgggcatt gccggtgtcg aggagatggt gatcgacatg      2040
ccagtcgaag gttggcgcca cacgctgttc gcgaatctga tcagcaatta cagcctgatg      2100
cgtaaactgg cgccgctgat gaaaaagcag ggttctggct acatcctgaa cgtttcttcc      2160
tacttcggcg gcgaaaagga tgcggccatc ccatatccga accgcgcaga ttacgcggtt      2220
tctaaagccg gccagcgtgc gatggcagaa gtgttcgccc gcttcctggg tccggagatc      2280
cagattaacg cgatcgcacc gggtccggtt gaaggtgatc gcctgcgtgg tacgggtgaa      2340
cgtccgggcc tgttcgcacg tcgtgcgcgt ctgatcctgg aaaacaagcg cctgaatgag      2400
ctgcacgcgg ccctgattgc agccgcgcgt accgacgaac gttctatgca cgagctggtg      2460
gagctgctgc tgccgaacga tgtggctgcc ctggaacaga tccagcagc accgaccgcg      2520
ctgcgcgaac tggcccgtcg tttcgttcc gaaggcgatc cggctgcatc ctcctccagc      2580
gcactgctga accgttctat cgcggcgaag ctgctggcac gcctgcacaa tggtggttac      2640
gtcctgccag ccgacatctt cgcaaacctg cctaacccac cggatccatt ctttacccgc      2700
gctcagatcg accgtgaagc gcgtaaagtt cgtgatggta tcatgggcat gctgtatctg      2760
cagcgtatgc cgacggagtt cgatgtcgcg atggcaaccg tctattacct ggccgaccgc      2820
aacgtgagcg cgaaaccttc caccccatcc ggtggcctgc gctatgaacg tacgccgacc      2880
ggtggtgagc tgttcggcct gccgagcccg gaacgcctgg cagaactggt tggctccacc      2940
gtgtacctga tcggtgaaca cctgacggag cacctgaacc tgctggcccg tgcgtatctg      3000
gagcgttatg gcgcacgtca agttgttatg atcgtggaaa ccgaaacggg tgccgaaact      3060
atgcgtcgtc tgctgcacga ccatgtcgaa gccggccgcc tgatgacgat cgtggctggt      3120
gaccagatcg aagcagccat cgatcaggca attacgcgtt atggtcgtcc gggtcctgtt      3180
gtttgcactc cattccgccc gctgccaact gtgcctctgg tcggtcgcaa ggactccgat      3240
tggagcacgg tcctgtctga agctgagttc gcggaactgt gcgagcatca gctgactcac      3300
cacttccgtt ttgctcgcaa gatcgcactg tccgatggcg ccagcctggc gctggtcacc      3360
ccagagacta ccgcaacttc taccactgaa caattcgctc tggcaaactt cattaaaact      3420
acgctgcacg ctttcaccgc gaccatcggc gttgagtccg aacgtacggc gcagcgtatc      3480
ctgatcaatc aggtggatct gactcgtcgt gcgcgcgccg aagaaccgcg cgatccgcac      3540
gaacgccagc aggaactgga gcgcttcatt gaagcagtcc tgctggtcac tgcgcctctg      3600
ccaccggaag cggacacgcg ctatgccggt cgcatccatc gcggccgtgc catcactgtc      3660
tga                                                                    3663
```

<210> SEQ ID NO 23
<211> LENGTH: 1220
<212> TYPE: PRT
<213> ORGANISM: Chloroflexus aurantiacus

<400> SEQUENCE: 23

Met Ser Gly Thr Gly Arg Leu Ala Gly Lys Ile Ala Leu Ile Thr Gly
1               5                   10                  15

Gly Ala Gly Asn Ile Gly Ser Glu Leu Thr Arg Arg Phe Leu Ala Glu
            20                  25                  30

-continued

Gly Ala Thr Val Ile Ile Ser Gly Arg Asn Arg Ala Lys Leu Thr Ala
        35                  40                  45

Leu Ala Glu Arg Met Gln Ala Glu Ala Gly Val Pro Ala Lys Arg Ile
 50                  55                  60

Asp Leu Glu Val Met Asp Gly Ser Asp Pro Val Ala Val Arg Ala Gly
 65                  70                  75                  80

Ile Glu Ala Ile Val Ala Arg His Gly Gln Ile Asp Ile Leu Val Asn
                 85                  90                  95

Asn Ala Gly Ser Ala Gly Ala Gln Arg Arg Leu Ala Glu Ile Pro Leu
                100                 105                 110

Thr Glu Ala Glu Leu Gly Pro Gly Ala Glu Thr Leu His Ala Ser
            115                 120                 125

Ile Ala Asn Leu Leu Gly Met Gly Trp His Leu Met Arg Ile Ala Ala
        130                 135                 140

Pro His Met Pro Val Gly Ser Ala Val Ile Asn Val Ser Thr Ile Phe
145                 150                 155                 160

Ser Arg Ala Glu Tyr Tyr Gly Arg Ile Pro Tyr Val Thr Pro Lys Ala
                165                 170                 175

Ala Leu Asn Ala Leu Ser Gln Leu Ala Ala Arg Glu Leu Gly Ala Arg
            180                 185                 190

Gly Ile Arg Val Asn Thr Ile Phe Pro Gly Pro Ile Glu Ser Asp Arg
        195                 200                 205

Ile Arg Thr Val Phe Gln Arg Met Asp Gln Leu Lys Gly Arg Pro Glu
210                 215                 220

Gly Asp Thr Ala His His Phe Leu Asn Thr Met Arg Leu Cys Arg Ala
225                 230                 235                 240

Asn Asp Gln Gly Ala Leu Glu Arg Arg Phe Pro Ser Val Gly Asp Val
                245                 250                 255

Ala Asp Ala Ala Val Phe Leu Ala Ser Ala Glu Ser Ala Ala Leu Ser
            260                 265                 270

Gly Glu Thr Ile Glu Val Thr His Gly Met Glu Leu Pro Ala Cys Ser
        275                 280                 285

Glu Thr Ser Leu Leu Ala Arg Thr Asp Leu Arg Thr Ile Asp Ala Ser
290                 295                 300

Gly Arg Thr Thr Leu Ile Cys Ala Gly Asp Gln Ile Glu Glu Val Met
305                 310                 315                 320

Ala Leu Thr Gly Met Leu Arg Thr Cys Gly Ser Glu Val Ile Ile Gly
                325                 330                 335

Phe Arg Ser Ala Ala Leu Ala Gln Phe Glu Gln Ala Val Asn Glu
            340                 345                 350

Ser Arg Arg Leu Ala Gly Ala Asp Phe Thr Pro Pro Ile Ala Leu Pro
        355                 360                 365

Leu Asp Pro Arg Asp Pro Ala Thr Ile Asp Ala Val Phe Asp Trp Gly
370                 375                 380

Ala Gly Glu Asn Thr Gly Gly Ile His Ala Ala Val Ile Leu Pro Ala
385                 390                 395                 400

Thr Ser His Glu Pro Ala Pro Cys Val Ile Glu Val Asp Asp Glu Arg
                405                 410                 415

Val Leu Asn Phe Leu Ala Asp Glu Ile Thr Gly Thr Ile Val Ile Ala
            420                 425                 430

Ser Arg Leu Ala Arg Tyr Trp Gln Ser Gln Arg Leu Thr Pro Gly Ala
        435                 440                 445

-continued

```
Arg Ala Arg Gly Pro Arg Val Ile Phe Leu Ser Asn Gly Ala Asp Gln
450                 455                 460
Asn Gly Asn Val Tyr Gly Arg Ile Gln Ser Ala Ala Ile Gly Gln Leu
465                 470                 475                 480
Ile Arg Val Trp Arg His Glu Ala Glu Leu Asp Tyr Gln Arg Ala Ser
                485                 490                 495
Ala Ala Gly Asp His Val Leu Pro Pro Val Trp Ala Asn Gln Ile Val
            500                 505                 510
Arg Phe Ala Asn Arg Ser Leu Glu Gly Leu Glu Phe Ala Cys Ala Trp
            515                 520                 525
Thr Ala Gln Leu Leu His Ser Gln Arg His Ile Asn Glu Ile Thr Leu
530                 535                 540
Asn Ile Pro Ala Asn Ile Ser Ala Thr Thr Gly Ala Arg Ser Ala Ser
545                 550                 555                 560
Val Gly Trp Ala Glu Ser Leu Ile Gly Leu His Leu Gly Lys Val Ala
                565                 570                 575
Leu Ile Thr Gly Gly Ser Ala Gly Ile Gly Gln Ile Gly Arg Leu
            580                 585                 590
Leu Ala Leu Ser Gly Ala Arg Val Met Leu Ala Ala Arg Asp Arg His
        595                 600                 605
Lys Leu Glu Gln Met Gln Ala Met Ile Gln Ser Glu Leu Ala Glu Val
    610                 615                 620
Gly Tyr Thr Asp Val Glu Asp Arg Val His Ile Ala Pro Gly Cys Asp
625                 630                 635                 640
Val Ser Ser Glu Ala Gln Leu Ala Asp Leu Val Glu Arg Thr Leu Ser
                645                 650                 655
Ala Phe Gly Thr Val Asp Tyr Leu Ile Asn Asn Ala Gly Ile Ala Gly
            660                 665                 670
Val Glu Glu Met Val Ile Asp Met Pro Val Glu Gly Trp Arg His Thr
            675                 680                 685
Leu Phe Ala Asn Leu Ile Ser Asn Tyr Ser Leu Met Arg Lys Leu Ala
        690                 695                 700
Pro Leu Met Lys Lys Gln Gly Ser Gly Tyr Ile Leu Asn Val Ser Ser
705                 710                 715                 720
Tyr Phe Gly Gly Glu Lys Asp Ala Ala Ile Pro Tyr Pro Asn Arg Ala
                725                 730                 735
Asp Tyr Ala Val Ser Lys Ala Gly Gln Arg Ala Met Ala Glu Val Phe
            740                 745                 750
Ala Arg Phe Leu Gly Pro Glu Ile Gln Ile Asn Ala Ile Ala Pro Gly
            755                 760                 765
Pro Val Glu Gly Asp Arg Leu Arg Gly Thr Gly Glu Arg Pro Gly Leu
        770                 775                 780
Phe Ala Arg Arg Ala Arg Leu Ile Leu Glu Asn Lys Arg Leu Asn Glu
785                 790                 795                 800
Leu His Ala Ala Leu Ile Ala Ala Arg Thr Asp Glu Arg Ser Met
                805                 810                 815
His Glu Leu Val Glu Leu Leu Pro Asn Asp Val Ala Ala Leu Glu
            820                 825                 830
Gln Asn Pro Ala Ala Pro Thr Ala Leu Arg Glu Leu Ala Arg Phe
            835                 840                 845
Arg Ser Glu Gly Asp Pro Ala Ala Ser Ser Ser Ala Leu Leu Asn
        850                 855                 860
Arg Ser Ile Ala Ala Lys Leu Leu Ala Arg Leu His Asn Gly Gly Tyr
```

```
                865                 870                 875                 880
Val Leu Pro Ala Asp Ile Phe Ala Asn Leu Pro Asn Pro Pro Asp Pro
                    885                 890                 895
Phe Phe Thr Arg Ala Gln Ile Asp Arg Glu Ala Arg Lys Val Arg Asp
                    900                 905                 910
Gly Ile Met Gly Met Leu Tyr Leu Gln Arg Met Pro Thr Glu Phe Asp
                    915                 920                 925
Val Ala Met Ala Thr Val Tyr Tyr Leu Ala Asp Arg Asn Val Ser Gly
                    930                 935                 940
Glu Thr Phe His Pro Ser Gly Gly Leu Arg Tyr Glu Arg Thr Pro Thr
945                 950                 955                 960
Gly Gly Glu Leu Phe Gly Leu Pro Ser Pro Glu Arg Leu Ala Glu Leu
                    965                 970                 975
Val Gly Ser Thr Val Tyr Leu Ile Gly Glu His Leu Thr Glu His Leu
                    980                 985                 990
Asn Leu Leu Ala Arg Ala Tyr Leu Glu Arg Tyr Gly Ala Arg Gln Val
                    995                 1000                1005
Val Met Ile Val Glu Thr Glu Thr Gly Ala Glu Thr Met Arg Arg Leu
        1010                1015                1020
Leu His Asp His Val Glu Ala Gly Arg Leu Met Thr Ile Val Ala Gly
1025                1030                1035                1040
Asp Gln Ile Glu Ala Ala Ile Asp Gln Ala Ile Thr Arg Tyr Gly Arg
                    1045                1050                1055
Pro Gly Pro Val Val Cys Thr Pro Phe Arg Pro Leu Pro Thr Val Pro
                    1060                1065                1070
Leu Val Gly Arg Lys Asp Ser Asp Trp Ser Thr Val Leu Ser Glu Ala
            1075                1080                1085
Glu Phe Ala Glu Leu Cys Glu His Gln Leu Thr His His Phe Arg Val
            1090                1095                1100
Ala Arg Lys Ile Ala Leu Ser Asp Gly Ala Ser Leu Ala Leu Val Thr
1105                1110                1115                1120
Pro Glu Thr Thr Ala Thr Ser Thr Thr Glu Gln Phe Ala Leu Ala Asn
                    1125                1130                1135
Phe Ile Lys Thr Thr Leu His Ala Phe Thr Ala Thr Ile Gly Val Glu
                    1140                1145                1150
Ser Glu Arg Thr Ala Gln Arg Ile Leu Ile Asn Gln Val Asp Leu Thr
            1155                1160                1165
Arg Arg Ala Arg Ala Glu Glu Pro Arg Asp Pro His Glu Arg Gln Gln
        1170                1175                1180
Glu Leu Glu Arg Phe Ile Glu Ala Val Leu Leu Val Thr Ala Pro Leu
1185                1190                1195                1200
Pro Pro Glu Ala Asp Thr Arg Tyr Ala Gly Arg Ile His Arg Gly Arg
                    1205                1210                1215
Ala Ile Thr Val
        1220
```